(12) United States Patent
Miyake et al.

(10) Patent No.: US 11,118,001 B2
(45) Date of Patent: *Sep. 14, 2021

(54) ISOCYANATE COMPOSITION, METHOD FOR PRODUCING ISOCYANATE COMPOSITION, AND METHOD FOR PRODUCING ISOCYANATE POLYMER

(71) Applicant: ASAHI KASEI KABUSHIKI KAISHA, Tokyo (JP)

(72) Inventors: Nobuhisa Miyake, Tokyo (JP); Masaaki Shinohata, Tokyo (JP); Atsushi Ohkubo, Tokyo (JP); Koichi Nakaoka, Tokyo (JP); Yuji Kosugi, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 109 days.

This patent is subject to a terminal disclaimer.

(21) Appl. No.: 16/340,532

(22) PCT Filed: Oct. 13, 2017

(86) PCT No.: PCT/JP2017/037276
§ 371 (c)(1),
(2) Date: Apr. 9, 2019

(87) PCT Pub. No.: WO2018/070540
PCT Pub. Date: Apr. 19, 2018

(65) Prior Publication Data
US 2020/0048403 A1 Feb. 13, 2020

(30) Foreign Application Priority Data

Oct. 14, 2016 (JP) .............................. JP2016-203101

(51) Int. Cl.
*C08G 18/72* (2006.01)
*C08G 18/77* (2006.01)
(Continued)

(52) U.S. Cl.
CPC .......... *C08G 18/725* (2013.01); *C07C 263/18* (2013.01); *C07C 265/04* (2013.01); *C07C 265/14* (2013.01); *C07C 271/52* (2013.01); *C08G 18/771* (2013.01); *C08G 18/775* (2013.01); *C08G 18/792* (2013.01); *C08G 18/798* (2013.01); *C08K 5/005* (2013.01); *C08K 5/0091* (2013.01); *C08K 5/01* (2013.01);
(Continued)

(58) Field of Classification Search
CPC .. C08G 18/725; C08G 18/771; C08G 18/775; C08G 18/792; C08G 18/798; C08K 5/005; C08K 5/0091; C08K 5/01; C08K 5/06; C08K 5/098; C08K 5/205; C08K 5/21; C08K 5/3442; C08K 5/34924; C08K 5/372; C07C 263/18; C07C 265/04; C07C 271/52; C07C 265/14
See application file for complete search history.

(56) References Cited

U.S. PATENT DOCUMENTS 3,247,236 A 4/1966 Adams
3,976,622 A 8/1976 Wagner et al.
(Continued)

FOREIGN PATENT DOCUMENTS

CA 2130685 A1 3/1995
CA 2 325 034 A1 9/1999
(Continued)

OTHER PUBLICATIONS

Written Opinion of the International Searching Authority dated Jan. 9, 2018, issued in corresponding application PCT/JP2017/037276.
European Search Report dated Oct. 2, 2019 issued in corresponding European Patent Application No. 17859611.0.
European Search Report in corresponding European Application No. 17859947.8 dated Sep. 18, 2019.
International Search Report issued in corresponding International Patent Application No. PCT/JP2017/037275 dated Jan. 16, 2018.
Written Opinion issued in corresponding International Patent Application No. PCT/JP2017/037275 dated Jan. 16, 2018.
(Continued)

*Primary Examiner* — Patrick D Niland
(74) *Attorney, Agent, or Firm* — Morgan, Lewis & Bockius LLP

(57) ABSTRACT

An isocyanate composition according to the present invention contains an isocyanate compound of formula (1) and/or (2) (wherein $R^1$ represents a hydrogen or a monovalent organic group, and $R^2$ represents a monovalent organic group), and, relative to the total mass of the isocyanate compound in the composition, 1.0 ppm by mass to 10% by mass of a compound of formula (3): $R^{13}$—(COO—$R^{14}$)a (wherein $R^{13}$ represents an organic group with a valence of a, $R^{14}$ represents a monovalent organic group, and a represents an integer of 1 or 2), which is different from the isocyanate compound, and/or, 1.0 ppm by mass to 10% by mass of a compound having an UV absorption in an area of decamer or higher isocyanates in a measurement spectrum of gel permeation chromatography.

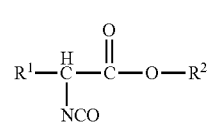

(1)

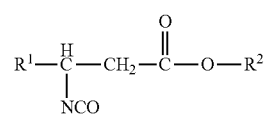

(2)

22 Claims, 1 Drawing Sheet

(51) Int. Cl.

| | | |
|---|---|---|
| *C08G 18/79* | (2006.01) | |
| *C08K 5/00* | (2006.01) | |
| *C08K 5/01* | (2006.01) | |
| *C08K 5/06* | (2006.01) | |
| *C08K 5/098* | (2006.01) | |
| *C08K 5/205* | (2006.01) | |
| *C07C 263/18* | (2006.01) | |
| *C07C 265/04* | (2006.01) | |
| *C07C 271/52* | (2006.01) | |
| *C07C 265/14* | (2006.01) | |
| *C08K 5/21* | (2006.01) | |
| *C08K 5/3442* | (2006.01) | |
| *C08K 5/3492* | (2006.01) | |
| *C08K 5/372* | (2006.01) | |

(52) U.S. Cl.
CPC ............... *C08K 5/06* (2013.01); *C08K 5/098* (2013.01); *C08K 5/205* (2013.01); *C08K 5/21* (2013.01); *C08K 5/3442* (2013.01); *C08K 5/34924* (2013.01); *C08K 5/372* (2013.01)

(56) References Cited

U.S. PATENT DOCUMENTS

| | | | |
|---|---|---|---|
| 4,064,157 | A | 12/1977 | Nafziger et al. |
| 4,176,132 | A | 11/1979 | Ide et al. |
| 4,290,969 | A | 9/1981 | Komatsu et al. |
| 4,318,861 | A | 3/1982 | Babiec, Jr. et al. |
| 4,324,879 | A | 4/1982 | Bock et al. |
| 4,412,073 | A | 10/1983 | Robin |
| 4,837,359 | A | 6/1989 | Woynar et al. |
| 4,983,762 | A | 1/1991 | Robin |
| 5,175,349 | A | 12/1992 | Gupta et al. |
| 5,641,851 | A | 6/1997 | Walff et al. |
| 5,728,317 | A | 3/1998 | Laqua et al. |
| 6,392,001 | B1 | 5/2002 | Mertes et al. |
| 2004/0049003 | A1 | 3/2004 | Asahina et al. |
| 2007/0197759 | A1 | 8/2007 | Binder et al. |
| 2013/0338330 | A1 | 12/2013 | Nakagawa et al. |
| 2015/0210631 | A1 | 7/2015 | Shinohata et al. |
| 2019/0225739 | A1* | 7/2019 | Miyake ............... C08K 5/109 |

FOREIGN PATENT DOCUMENTS

| | | |
|---|---|---|
| CN | 1478112 A | 2/2004 |
| CN | 104250363 A | 12/2014 |
| EP | 0 561 568 A1 | 9/1993 |
| EP | 0 744 422 A1 | 11/1996 |
| EP | 2 915 803 A1 | 9/2015 |
| GB | 994890 A | 6/1965 |
| GB | 2 031 914 A | 4/1980 |
| JP | 46-035246 B | 10/1971 |
| JP | 53-135931 A | 11/1978 |
| JP | 56-061341 A | 5/1981 |
| JP | 57-047319 A | 3/1982 |
| JP | 57-115416 A | 7/1982 |
| JP | 60-054349 B | 11/1985 |
| JP | 63-057577 A | 3/1988 |
| JP | 04-066863 B | 10/1992 |
| JP | 05-255469 A | 10/1993 |
| JP | 06-092925 A | 4/1994 |
| JP | 07-149705 A | 6/1995 |
| JP | H7-304724 A | 11/1995 |
| JP | 2002-003462 A | 1/2002 |
| JP | 2002-003568 A | 1/2002 |
| JP | 2002-507594 A | 3/2002 |
| JP | 2002-363151 A | 12/2002 |
| JP | 2005-047854 A | 2/2005 |
| JP | 2005-048073 A | 2/2005 |
| JP | 2007-528885 A | 10/2007 |
| JP | 2008-143872 A | 6/2008 |
| JP | 2015-010183 A | 1/2015 |
| JP | 2015-501358 A | 1/2015 |
| JP | 2015-028163 A | 2/2015 |
| JP | 5849088 B2 | 1/2016 |
| JP | 2016-069496 A | 5/2016 |
| JP | 2017-031174 A | 2/2017 |
| WO | 02/42351 A1 | 5/2002 |
| WO | 2004/078819 A1 | 9/2004 |
| WO | 2012/121291 A1 | 9/2012 |
| WO | 2013060614 A1 | 5/2013 |
| WO | 2014/069605 A1 | 5/2014 |

OTHER PUBLICATIONS

International Search Report issued in corresponding International Application No. PCT/JP2017-037276, dated Jan. 9, 2018.

Sheng Mao Gui et al., "New Polyurethane Resin Coating Production Tecnoloogy and Application," Guangddong Science and Technology Press, 1st Edition, 75-76 (Feb. 2001) (see CN OA).

Office Action issued in related Chinese Patent Application No. 201780062137.1 dated Jul. 8, 2021.

\* cited by examiner

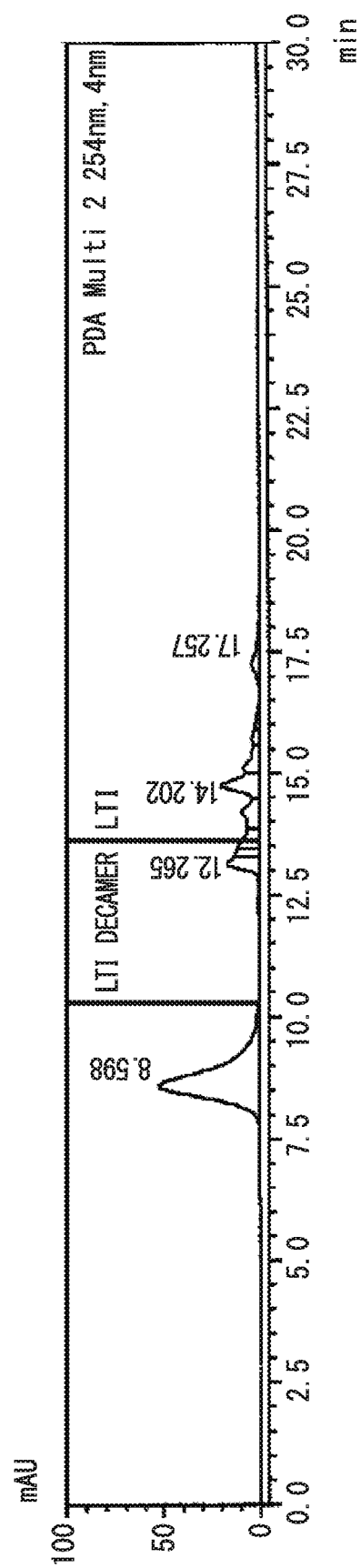

ISOCYANATE COMPOSITION, METHOD FOR PRODUCING ISOCYANATE COMPOSITION, AND METHOD FOR PRODUCING ISOCYANATE POLYMER

TECHNICAL FIELD

The present invention relates to an isocyanate composition, a method for producing the isocyanate composition, and a method for producing an isocyanate polymer.

The present invention claims priority on the basis of Japanese Patent Application No. 2016-203101 filed in Japan on Oct. 14, 2016, the contents of which are incorporated herein by reference.

BACKGROUND OF THE INVENTION

A method for producing a lysine isocyanate using, as a raw material thereof, a L-lysine, which is an α-amino acid, as an amino group of an aliphatic amine has been disclosed (Patent Document 1).

A method for purifying a lysine isocyanate-β-isocyanate ethyl ester (LDI) having an ester group in a structure thereof has been disclosed (Patent Document 2).

A problem in which an aliphatic isocyanate having an ester group in a structure thereof is easily colored has been known. Although the cause of coroling the isocyanate is not clear, it is known that a lysine ester triisocyanate or the like is sensitive to heat, and causes the generation of tar in an amount larger than that of a reaction liquid of an isocyanate in which an aliphatic group is a hydrocarbon group having a saturated hydrocarbon group and an alicyclic group, and thereby it is difficult to remove colored impurities (Patent Document 3). Although it is presumed that the cause of the coloring thereof is different from the cause of coloring the isocyanate in which an aliphatic group is a hydrocarbon group having a saturated hydrocarbon group and an alicyclic group, it is not clear.

Methods for decoloring isocyanate obtained using L-lysine, which is an α-amino acid, as a raw material have been studied (Patent Documents 3 to 5, for example).

DOCUMENTS OF RELATED ART

Patent Documents

Patent Document 1: Japanese Examined Patent Publication No. Sho 46-35246
Patent Document 2: Japanese Examined Patent Publication No. Sho 60-54349
Patent Document 3: Japanese Examined Patent Publication No. Hei 4-66863
Patent Document 4: Japanese Unexamined Patent Application Publication No. 2002-3462
Patent Document 5: Japanese Unexamined Patent Application Publication No. Hei 2002-363151

SUMMARY OF THE INVENTION

Problems to be Solved by the Invention

As mentioned above, several methods for decolorization in a synthesis step of a crude isosyante in which lysine is used as a raw material have been studied. However, there is a case where the isocyanate is colored when synthesized, and also colored or denaturated when stored for a long time. In the case when the isocyanate is used to conduct coating, coloring or stability when stored for a long time poses significant issues.

Patent Document 3 discloses a method in which the purification step includes a step for removing tar, a step for rectification and two steps for distillation, Patent Document 4 discloses in examples a method in which a mixture containing LTI is contacted with an activated carbon or a metallic halide, followed by conducting distillation using a falling thin-film-type molecular distillation apparatus made of glass, and Patent Document 5 discloses a method in which a persulfate is added to a crude LTI, the mixture is heated, and subjected to separation by filtration, followed by conducting distillation using a falling thin-film-type molecular distillation apparatus made of glass. However, there are additional problems in terms of coloring and denaturation over time. In particular, there is a case in which an isocyanate having the following specific structure is denaturated to generate a viscous gelatinous material or solid content when stored for a long time, which is a significant issue when used to conduct coating in which the transparency and the homogeneousness are seen as being important matters.

A method for preventing coloring or suppressing denaturation of an isocyanate compound having an ester bond whith is sensitive to heat in comparison with an isocyanate in which an aliphatic group is a hydrocarbon group having a saturated hydrocarbon group and an alicyclic group, when stored for a long time, has not been disclosed, and problems remain still. In addition, methods for preventing coloring or suppressing denaturation of polyisoyante obtained using the isocyanate compound, when stored for a long time, have also not been known.

In view of the above-mentioned circumstances, the present invention aims to provide a composition containing an isocyanate compound having an ester bond in which the coloring and denaturation when stored for a long time are sufficiently suppressed

Means to Solve the Problems

The present inventors have made intensive studies in order to solve the above problems, found that an isocyanate composition containing specific components sufficiently suppresses coloring while maintaining the stability when stored for a long time, and thereby completed the present invention.

The present invention encompasses the following aspects.

(1) An isocyanate composition containing an isocyanate compound of the following formula (1) and/or formula (2), further containing:

a compound of formula (3), which is different from the isocyanate compound, in an amount of 1.0 ppm by mass to 10% by mass, relative to the total mass of the isocyanate compounds in the isocyanate composition;

a compound having an UV absorption in an area of decamer or higher isocyanates in a measurement spectrum of gel permeation chromatography, in an amount of 1.0 ppm by mass to 10% by mass, relative to the total mass of the isocyanate compound in the isocyanate composition; and/or, a compound having an isocyanurate group and/or a biuret group in an amount of 1.0 ppm by mass to 10% by mass, relative to the total mass of the isocyanate compound in the isocyanate composition.

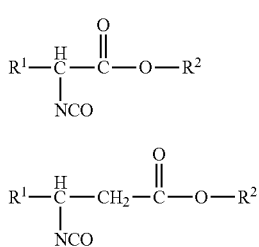

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, R1 may be —C(=O)OR$^2$ or —CH$_2$—C(=O)O—R$^2$.

$$R^{13}-(COO-R^{14})_a \quad (3)$$

In the formula, $R^{13}$ represents an organic group with a valence of a, $R^{14}$ represents a monovalent organic group, and a represents an integer of 1 or 2.

(2) The isocyanate composition according to (1), further containing, relative to the total mass of the isocyanate compound in the composition,
1.0 ppm by mass to 10% by mass of a saturated and/or unsaturated hydrocarbon compound having a linear-chain structure, a branched-chain structure, or a cyclic structure, and/or,
1.0 ppm by mass to 10% by mass of a compound having at least one bond selected from the group consisting an ether bond and a thioether bond.

(3) The isocyanate composition according to (1) or (2), further containing at least one selected from the group consisting of carbamate group-containing compounds and carbonic acid esters, in an amount of 1.0 ppm by mass to 10% by mass, relative to the total mass of the isocyanate compound in the composition.

(4) The isocyanate composition according to any one of (1) to (3), further containing at least one selected from the group consisting of basic amino compounds, halogen ions and hydrolyzable halogen compounds, in an amount of 1.0 ppm by mass to 10% by mass, relative to the total mass of the isocyanate compound in the composition.

(5) The isocyanate composition according to any one of (1) to (4), further containing, relative to the total mass of the isocyanate compound in the composition, 1.0 ppm by mass to $1.0 \times 10^3$ ppm by mass of phosphoric acid and/or phosphoric acid ester, and/or, 1.0 ppm by mass to $1.0 \times 10^3$ ppm by mass of sulfuric acid and/or sulfuric acid ester.

(6) The isocyanate composition according to any one of (1) to (5), wherein, as the isocyanate compound, a trifunctional isocyanate compound having three isocyanate groups in a molecule thereof and a difunctional isocyanate compound having two isocyanate groups in a molecule thereof are contained.

(7) An isocyanate composition comprising an isocyanate compound of formula (1) and/or formula (2), wherein, as the isocyanate compounds, a trifunctional isocyanate compound having three isocyanate groups in a molecule thereof and a difunctional isocyanate compound having two isocyanate groups in a molecule thereof are contained.

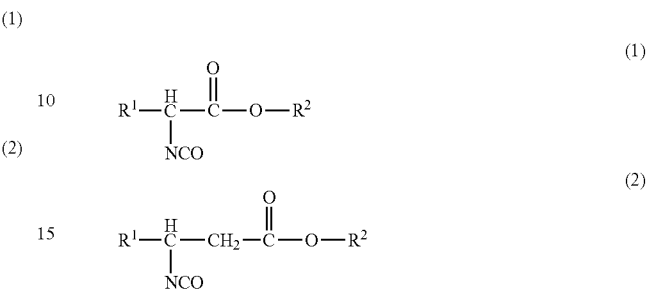

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may be —C(=O)OR$^2$ or —CH$_2$—C(=O)O—R$^2$. At leas one of $R^1$ and $R^2$ has an isocyanate group, and the total number of isocyanate groups in $R^1$ and $R^2$ is 2 or 3.

(8) An isocyanate composition containing: an isocyanate compound of the following formula (1) and/or formula (2); and a stabilizer which is different from the isocyanate compound in an amount of 0.002 ppm by mass to 10% by mass, relative to the total mass of the isocyanate compound in the isocyanate composition, wherein the stabilizer is at least one compound selected from the group consisting of: saturated and/or unsaturated hydrocarbon compounds having a linear-chain, branched-chain, or cyclic structures; compounds having at least one bond selected from the group consisting of an ether bond and a thioether bond; carbamate group-containing compounds; carbonic acid esters; basic amino compounds; halogen ions and/or hydrolyzable halogen compounds; metallic atoms; and carbon dioxide.

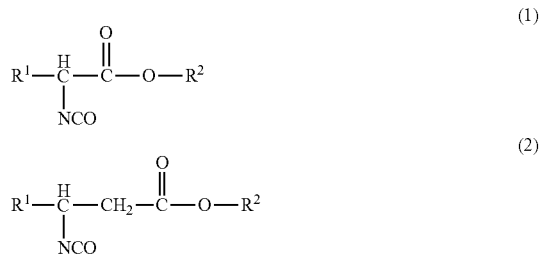

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may be —C(=O)OR$^2$ or —CH$_2$—C(=O)O—R$^2$.

(9) An isocyanate composition according to (8), further containing, relative to the total mass of the isocyanate compound in the composition, 1.0 ppm by mass to $1.0 \times 10^3$ ppm by mass of a phosphoric acid and/or a phosphoric acid ester, and/or, 1.0 ppm by mass to $1.0 \times 10^3$ ppm by mass of a sulfuric acid and/or a sulfuric acid ester.

(10) An isocyanate composition containing: an isocyanate compound of the following formula (1) and/or formula (2); and, relative to the total mass of the isocyanate compound in the composition, 1.0 ppm by mass to $1.0 \times 10^3$ ppm by mass of a phosphoric acid and/or a phosphoric acid ester, and/or, 1.0 ppm by mass to $1.0 \times 10^3$ ppm by mass of a sulfuric acid and/or a sulfuric acid ester.

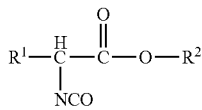

(1)

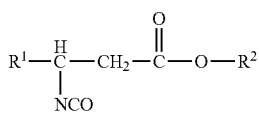

(2)

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may be —C(=O)OR$^2$ or —CH$_2$—C(=O)O—R$^2$.

(11) The isocyanate composition according to any one of (1) to (10), wherein the amount of the isocyanate compound, relative to the total mass of the isocyanate composition, is not less than 90% by mass.

(12) The isocyanate composition according to any one of (1) to (11), containing the isocyanate compound of formula (1), wherein the isocyanate compound has a structure derived from an α-amino acid.

(13) The isocyanate composition according to any one of (1) to (12), containing the isocyanate compound of formula (2), wherein the isocyanate compound has a structure derived from a β-amino acid.

(14) A method for producing an isocyanate composition of (12) or (13), containing preparing an isocyanate compound of the following formula (1) and/or formula (2) using, as a raw material, at least one of α-amino acids and β-amino acids corresponding thereto, wherein the amino acid is an amino acid having a purity of not less than 90%.

(15) The method for producing an isocyanate composition according to (14), further containing a distillation purification step of the isocyanate compound.

(16) A method for producing an isocyanate polymer, containing a reaction step of the isocyanate compound contained in the isocyanate composition of any one of (1) to (13),
wherein the isocyanate polymer contains: a unit of the following formula (4); and at least one unit selected from the group consisting of units of the following formula (5), (6), (7), (8), (9), (10), (11) or (12), and
a nitrogen atom constituting the isocyanate polymer bonds with a carbon atom.

(4)

(5)

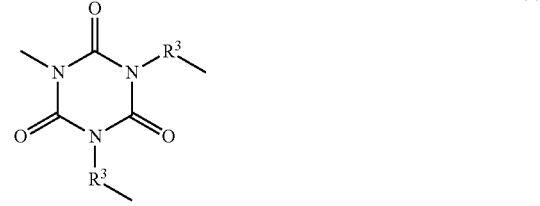

(6)

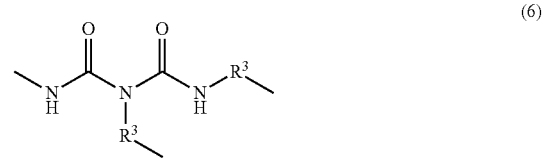

(7)

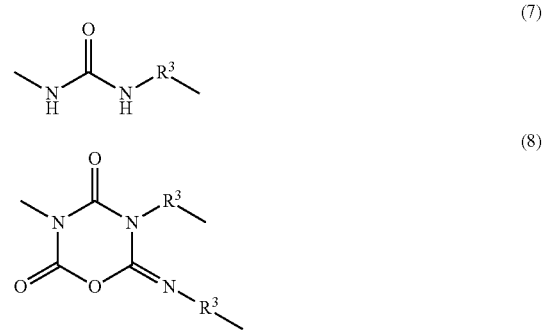

(8)

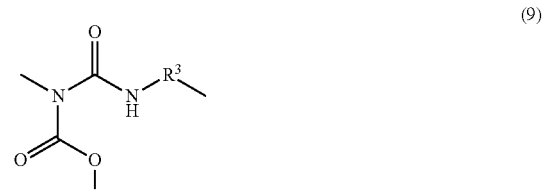

(9)

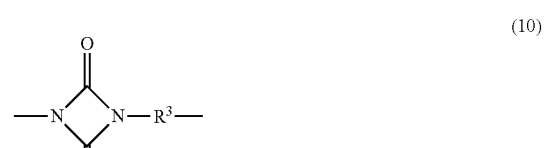

(10)

(11)

(12)

In the formulae, each $R^3$ independently represents a divalent hydrocarbon group, and each $R^4$ independently represents a monovalent organic group.

Effects of the Invention

The present invention provides an isocyanate composition containing a specific isocyanate compound, which is excellent in coloring preventability and stability when stored for a long time.

BRIEF DESCRIPTION OF DRAWINGS

FIG. 1 is a drawing showing a measurement spectrum of gel permeation chromatography obtained in Synthesis Example A1.

EMBODIMENTS FOR CARRYING OUT THE INVENTION

Preferable embodiments of the present invention will be described below. The present invention is not limited to the following embodiments, and the present invention may be modified in various ways within the summary thereof.

Although the terms "organic group", "aliphatic", and "aromatic" are used in the present specification, the terms mean those cited from "organic chemistry and biochemistry nomenclature" (published by Japanese Nankodo in 1992 as the revised second edition) containing all rules of organic chemistry and biochemistry published as a separate volume of "chemistry region" in 1980 based on Recommendations 1979, the volume encompassing the rules translated into Japanese, and all subsequent revisions and recommendations based thereon, when IUPAS Rules and Nomenclature rules stipulated by IUPAC and also described below (excepting the case where IUPAC Recommendations in other year is specially cited) is referred. The term "organic" refers to general compounds which are objects of nomenclature disclosed in the nomenclature. The objects may be objects disclosed in Recommendations issued in 1993. The "organic" compounds which are objects of the Nomenclature encompass organic metal compounds and metal complexes. In the present embodiment, the terms "organic group" and "substituent group" refer to groups constituted by atoms free from metal atoms and/or metalloids, unless otherwise indicated particularly. In addition, an "organic compound", "organic group" or "substituent group", constituted by atoms selected from the group consisting of H (hydrogen atom), C (carbon atom), N (nitrogen atom), O (oxygen atom), S (sulfur atom), Cl (chlorine atom), Br (bromine atom), and I (iodine atom) are preferably used in the present embodiment.

The terms "aliphatic" and "aromatic" are used many times in the following description. It is described in the IUPAC Rules that the organic compounds are classified into aliphatic compounds and aromatic compounds. The aliphatic compounds are aliphatic compounds based on IUPAC Recommendation in 1995. In the Recommendation, the aliphatic compounds are defined as "acyclic or cyclic, saturated or unsaturated carbon compounds, excluding aromatic compounds". The term "aliphatic compound" used in the description of the present embodiment encompasses saturated or unsaturated, and chain or cyclic aliphatic compounds, and refers to "organic compound", "organic group" or "substituent group" constituted by atoms selected from the group consisting of H (hydrogen atom); C (carbon atom); N (nitrogen atom); O (oxygen atom); S (sulfur atom); Si (silicon atom); and halogen atoms selected from the group consisting of Cl (chlorine atom), Br (bromine atom) and I (iodine atom).

In the case where an aromatic group such as an aralkyl group is bonded to an aliphatic group, it may be indicated as "an aliphatic group substituted with an aromatic group", or "a group constituted by an aliphatic group bonded with an aromatic group" depending on the reactivity in the present embodiment, because the reactivity of a group such as an aralkyl group is not similar to the reactivity of aromatic groups but extremely similar to that of aliphatic groups. In addition, a non-aromatic reactive group having an aralkyl group, an alkyl group, or the like, may be indicated as "an aliphatic group substitutable with an aromatic group", "an aliphatic group substitutable with an aromatic group", "an aliphatic group bondable with an aromatic group", or the like.

Although the general formula of a compound used in the present specification is described in accordance with Nomenclature Rule stipulated by IUPAC, names of specific groups or exemplified compounds may be indicated by common names. In addition, all of numbers of atoms or substituent groups indicated in the present specification are integers.

In the present specification, the term "active hydrogen" refers to a hydrogen atom bonded with an oxygen atom, sulfur atom, nitrogen atom, silicon atom, or the like (excepting aromatic hydroxy group), or a hydrogen atom of a terminal methine group. The "active hydrogen" is, for example, a hydrogen included in an atomic group such as C(=O)OH group, —C(=O)H group, —SH group, —SO$_3$H group, —SO$_2$H group, —SOH group, —NH$_2$ group, —NH group, —SiH group, —C≡CH group, or the like. Although a hydrogen atom included in a hydroxy group (—OH group) is encompassed in the definition of the term "active hydrogen", a hydroxy group (—OH group) is not encompassed in a group having an "active hydrogen", unless otherwise indicated. Examples of a compound having a hydroxy group include alcohols and aromatic hydroxy compounds.

The term "alcohol" used in the present specification means "compound in which a hydroxy group, —OH, is attached to a saturated carbon atom: R$_3$COH)" described in the definition (Rule C-201) of IUPAC, and aromatic hydroxy compounds in which a hydroxy group is attached to an aromatic ring are not encompassed thereby.

The term "aromatic hydroxy compound" used in the present specification means phenol described in the definition (Rule C-202) of IUPAC "compound having one or more hydroxy groups attached to a benzene or other arene ring".

The term "unsaturated bond" used in the present specification means a chemical bond between two atoms formed by two or three covalent bonds, and encompasses double bond and triple bond (chemical encyclopedia 7 scaled-down version (Kyoritsu Shuppan Co., Ltd., issued in Oct. 1, 2003)). Examples of the unsaturated bond include C=C, C≡C, C=O, C=N, C≡N, N=N, and N=O.

First, a compound included in an isocyanate composition according to the present embodiment is described.

<Isocyanate Compound>

An isocyanate composition according to the present embodiment contains an isocyanate compound having a structure (A) of the following formula (A) and/or a structure (B) of the following formula (B).

The isocyanate compound having the structure (A) is represented by the following formula (1), and the isocyanate compound having the structure (B) is represented by the following formula (2).

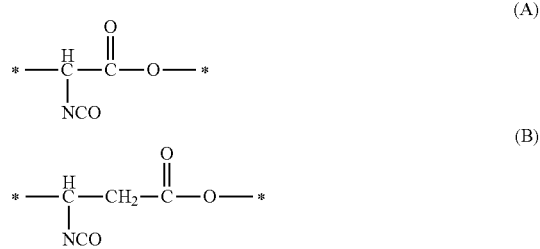

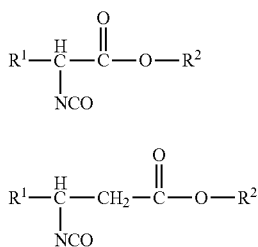

(1)

(2)

In the formulae (A) and (B), * represents a bond with $R^1$ or $R^2$ in the formula (1) or (2).

In the formulae (1) and (2), $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may be —C(=O)O$R^2$ or —CH$_2$—C(=O)O—$R^2$.

For example, compounds of the following formula (1-1), (1-2) or (1-3) are isocyanate compounds of formula (1) having only the structure (A), compounds of the following formula (2-1), (2-2) or (2-3) are isocyanate compounds of formula (2) having only the structure (B), and compounds of the following formula (1-2-1), (1-2-2), (1-2-3) or (1-2-4) are isocyanate compounds of formulae (1) and (2) having both the structure (A) and the structure (B).

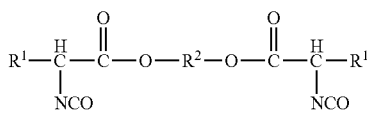

(1-1)

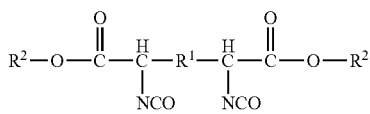

(1-2)

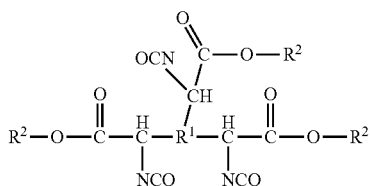

(1-3)

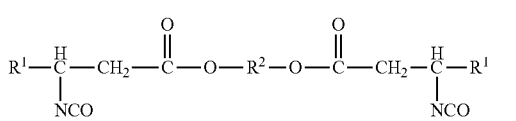

(2-1)

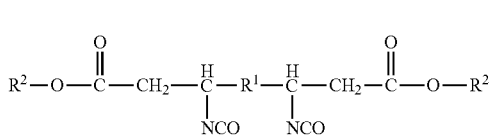

(2-2)

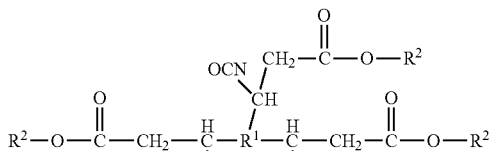

(2-3)

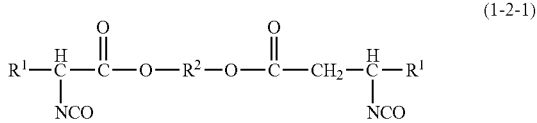

(1-2-1)

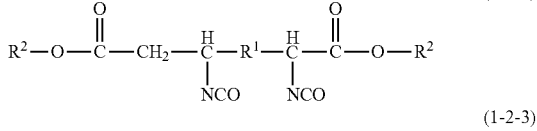

(1-2-2)

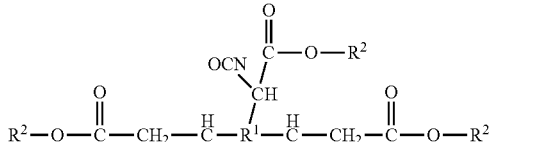

(1-2-3)

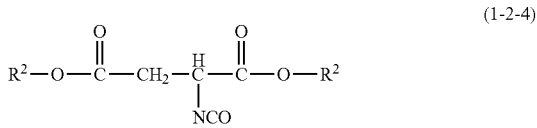

(1-2-4)

The structure of the formula (1-2-4) is considered as one of the compounds of formula (1) in which $R^1$ is represented by $R^2$—O—C(=O)—CH$_2$—, and also as one of the compounds of formula (2) in which $R^1$ is represented by $R^2$—O—C(=O)—.

The isocyanate compound according to the present embodiment is an isocyanate compound having the structure (A) and/or the structure (B). Even if an isocyanate group (NCO group) included in the structure (A) and/or the structure (B) constitutes a portion of a dimeric structure (such as uretdione) or a trimeric structure (such as isocyanurate), the structure is deemed as an isocyanate compound according to the present invention. In the case where the isocyanate compound of formula (1) and/or formula (2) has a dimeric structure or a trimeric structure, there is a case where the amount of isocyanate decreases, and therefore it is preferable that $R^1$ and/or $R^2$ have at least one isocyanate group.

The isocyanate compounds of the formula (1) and/or the formula (2) contain the structure (A) and/or the structure (B) having a bond of —C(=O)O— neighboring an isocyanate group. It is known that when a functional group having a hetero atom (such as nitrogen, oxygen, sulfur, phosphorus, chlorine, bromine, or iodine) neighbors to a carbon chain or a carbon ring, the resultant exhibits properties or behaviors different from the carbon chain or the carbon ring, and there is a case where the neighboring hetero atom exhibits chelate effects or causes phenomena that are not expected from the corresponding carbon chain skeleton.

The isocyanate compound according to the present embodiment has the structure (A) and/or the structure (B). The isocyanate compounds may have a plurality of the structure (A) or the structure (B) in a molecule thereof, and may have both the structure (A) and the structure (B) in a molecule thereof.

$R^1$ represents a hydrogen or an organic group. The organic group is a C1-85 monovalent organic group, and may have a bond having a hetero atom, or may be substituted with a functional group having a hetero atom. $R^1$ may represent a residual group obtained by removing a hydrogen atom from the group $R^1$ or the group $R^2$ of the compound of the formula (1) or the formula (2), or a residual group obtained by removing the group $R^1$ or the group $R^2$ from the compound of the formula (1) or the formula (2). $R^1$ may represent a group represented by —C(=O)OR$^2$ or —CH$_2$—C(=O)O—R$^2$.

Examples of the organic group include aliphatic hydrocarbon groups, alicyclic hydrocarbon groups (hydrocarbon groups having alicyclic groups), aromatic hydrocarbon group (hydrocarbon groups having aromatic rings), and groups in which aliphatic groups and aromatic groups are bonded. Specific examples of the organic group include: cyclic groups such as cyclic hydrocarbon groups (monocyclic hydrocarbon groups, condensed polycyclic hydrocarbon groups, crosslinked cyclic hydrocarbon groups, spiro hydrocarbon groups, ring-assembly hydrocarbon groups, side chain-containing cyclic hydrocarbon groups), heterocyclic groups, heterocyclic spiro groups, and hetero crosslinked cyclic groups; acyclic hydrocarbon groups, groups bonded with at least one selected from the group consisting of acyclic hydrocarbon groups and cyclic groups, and groups in which acyclic hydrocarbon groups are bonded with cyclic groups. Atoms or groups constituting the above-mentioned groups may be substituted with functional groups having hetero atoms (such as nitrogen, oxygen, sulfur, phosphorus, chlorine, bromine, or iodine), and the groups may be groups bonded with specific nonmetallic atoms (such as carbon, oxygen, nitrogen, sulfur, or silicon) via covalent bonds. The atoms or groups constituting the above-mentioned groups are preferably substituted with isocyanate groups.

The covalent bond with the specific nonmetallic atom may generate the state, for example, in which the above-mentioned group is bonded with at least one selected from groups of the following formula (13) to (30) via a covalent bond.

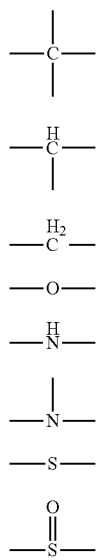

(13)
(14)
(15)
(16)
(17)
(18)
(19)
(20)

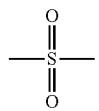

(21)

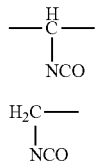

(22)

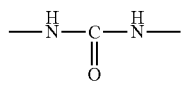

(23)

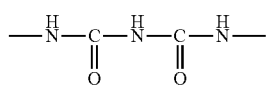

(24)

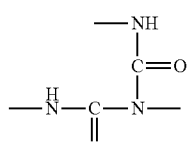

(25)

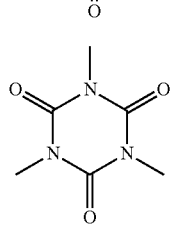

(26)

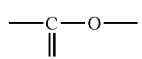

(27)

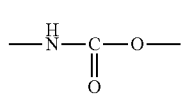

(28)
(29)

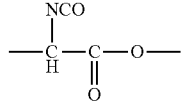

(30)

Examples of the aliphatic hydrocarbon group include groups having 1-40 carbon atoms (preferably 2-20 carbon atoms, and more preferably 2-10 carbon atoms). Specific examples of the aliphatic hydrocarbon group include groups obtained by removing a hydrogen atom from aliphatic hydrocarbons, such as butane (including isomers), pentane (including isomers), hexane (including isomers), heptane (including isomers), octane (including isomers), decane (including isomers), dodecane (including isomers), and octadecane (including isomers).

Examples of the alicyclic hydrocarbon group include groups having 6-40 carbon atoms (preferably 6-20 carbon atoms, and more preferably 6-10 carbon atoms). Specific examples of the alicyclic hydrocarbon group include groups obtained by removing a hydrogen atom from alicyclic hydrocarbons, such as cyclohexane, dimethylcyclohexane (including isomers), tetramethylcyclohexane (including isomers), dicyclohexylmethane, cyclopentane, and cyclooctane.

Examples of the aromatic hydrocarbon groups include groups having 6-40 carbon atoms (preferably 6-30 carbon atoms). Specific examples of the aromatic hydrocarbon group include groups obtained by removing a hydrogen atom from aromatic hydrocarbons, such as benzene, toluene, xylene (including isomers), naphthalene, diphenylmethane, and biphenyl (preferably benzene).

$R^1$ may be a group in which the above-exemplified organic group is substituted with a substituent group, such as a halogen group, alkoxy (preferably having 1-6 carbon atoms), alkoxycarbonyl group (preferably having 1-6 carbon atoms), aromatic hydroxy group, or aromatic hydroxy carbonyl group. However, it is preferable from the viewpoint of stability that $R^1$ be free from groups having an active hydrogen, such as a terminal methine group, an alcoholic OH group, a carboxyl group, a $NH_2$ group, a NOH group, a SH group, a $SO_3H$ group, or a SOH group.

The isocyanate compound according to the present embodiment is an isocyanate compound having the structure (A) and/or the structure (B). The structure (A) and/or structure (B) in which an amino group of an amino acid is substituted with an isocyanate group is preferably derived from an amino acid, and a portion or the whole of $R^1$ may be derived from an amino acid. The amino acid may be an amino acid obtained by fermentation or chemical synthesis. The structure (A) is preferably derived from an α-amino acid, and the structure (B) is preferably derived from a I3-amino acid.

Preferable examples of the amino acid include glycine, alanine (including isomers), valine (including isomers), leucine (including isomers), aspartic acid (including isomers), glutamic acid (including isomers), lysine (including isomers), phenylalanine (including isomers), cystine (including isomers), methionine (including isomers), serine (including isomers), threonine (including isomers), and 2,6-diamino heptanedionate. Isomers may include any of optical isomers and positional isomers (α-amino acid and/or β-amino acid). Among the isomers, at least one of the α-amino acid structures capable of forming the structure (A) that can enhance the activity of an isocyanate group is preferably contained. An α-amino acid having L-configuration is more preferable.

Among the above-mentioned amino acids, it is preferable that the isocyanate compound according to the present embodiment have a structure in which amino groups of an amino acid having a plurality of amino groups are replaced with isocyanate groups, and a structure in which a carboxyl group of an amino acid is replaced with an ester group free from active hydrogens is preferable.

$R^2$ represents an organic group. The organic group is preferably an organic group having 1-85 carbon atoms, and more preferably 1-8 carbon atoms. The organic group may have a bond having a hetero atom, or may be substituted with a functional group having a hetero atom, as mentioned below. $R^2$ may represent a residual group obtained by removing a hydrogen atom from the group $R^1$ or the group $R^2$ of the formula (1) or formula (2), or a residual group obtained by removing the group $R^1$ or the group $R^2$ from the compound of the formula (1) or the formula (2).

Examples of the organic group include aliphatic hydrocarbon groups, alicyclic hydrocarbon groups (hydrocarbon groups having alicyclic groups), aromatic hydrocarbon groups (hydrocarbon groups having aromatic rings), and groups in which aliphatic groups and aromatic groups are bonded. Specific examples of the organic group include: cyclic hydrocarbon groups (monocyclic hydrocarbon groups, condensed polycyclic hydrocarbon groups, crosslinked cyclic hydrocarbon groups, spiro hydrocarbon groups, ring-assembly hydrocarbon groups, and side chain-containing cyclic hydrocarbon groups): cyclic groups such as heterocyclic groups, heterocyclic spiro groups, and hetero crosslinked cyclic groups; acyclic hydrocarbon group, groups bonded with at least one selected from the group consisting of acyclic hydrocarbon groups and cyclic groups, and groups in which acyclic hydrocarbon groups and cyclic groups are bonded. Atoms or groups constituting the above-mentioned groups may be substituted with a functional group having a hetero atom (such as nitrogen, oxygen, sulfur, phosphorus, chlorine, bromine, or iodine), and the group may be a group in which a specific nonmetallic atom (such as carbon, oxygen, nitrogen, sulfur or silicon) is bonded via a covalent bond. The atoms or groups constituting the group are preferably substituted with isocyanate groups.

The covalent bond with the specific nonmetallic atom may generate the state, for example, in which the above-mentioned group is bonded with at least one selected from the groups of the following formula (13) to (30), mentioned in the description regarding $R^1$ above, via a covalent bond.

Examples of the hydrocarbon groups include groups having 1-40 carbon atoms (preferably 1-20 carbon atoms, and more preferably 2-8 carbon atoms). Specific examples of the aliphatic hydrocarbon group include groups obtained by removing a hydrogen atom from aliphatic hydrocarbons, such as butane (including isomers), pentane (including isomers), hexane (including isomers), heptane (including isomers), octane (including isomers), decane (including isomers), dodecane (including isomers), and octadecane (including isomers).

Examples of the alicyclic hydrocarbon group include groups having 6-40 carbon atoms (preferably 6-15 carbon atoms, and more preferably 6-8 carbon atoms). Specific examples of the alicyclic hydrocarbon group include groups obtained by removing a hydrogen atom from alicyclic hydrocarbons, such as cyclohexane, dimethylcyclohexane (including isomers), tetramethylcyclohexane (including isomers), dicyclohexylmethane, cyclopentane, and cyclooctane.

Examples of the aromatic hydrocarbon group include groups having 6-40 carbon atoms (preferably 6-15 carbon atoms, and more preferably 6-8 carbon atoms). Specific examples of the aromatic hydrocarbon group include groups obtained by removing a hydrogen atom from aromatic hydrocarbons, such as benzene, toluene, xylene (including isomers), naphthalene, diphenylmethane, and biphenyl.

In addition, $R^2$ may be a group in which the above-exemplified organic group is substituted with a substituent group, such as a halogen group, an alkoxy group, an alkoxycarbonyl group, an aromatic hydroxy group, or an aromatic hydroxy carbonyl group.

Among these, $R^2$ preferably has an isocyanate group, and a group having 1-8 carbon atoms, which may have a hetero atom. $R^2$ is more preferably an organic group having a methyl group, an ethyl group, a propyl group (including isomers), a butyl group (including isomers), a pentyl group (including isomers), a hexyl group (including isomers), a heptyl group (including isomers), or an octyl group (including isomers), and more preferably an isocyanate group, and examples thereof include an isocyanate methyl group, an isocyanate ethyl group (including isomers), an isocyanate propyl group (including isomers), an isocyanate butyl group (including isomers), and an isocyanate pentyl group (including isomers).

Preferable examples of the combination of $R^1$ and $R^2$, as the isocyanate compounds according to the present embodiment, include isocyanate compounds having the following structures (including isomers).

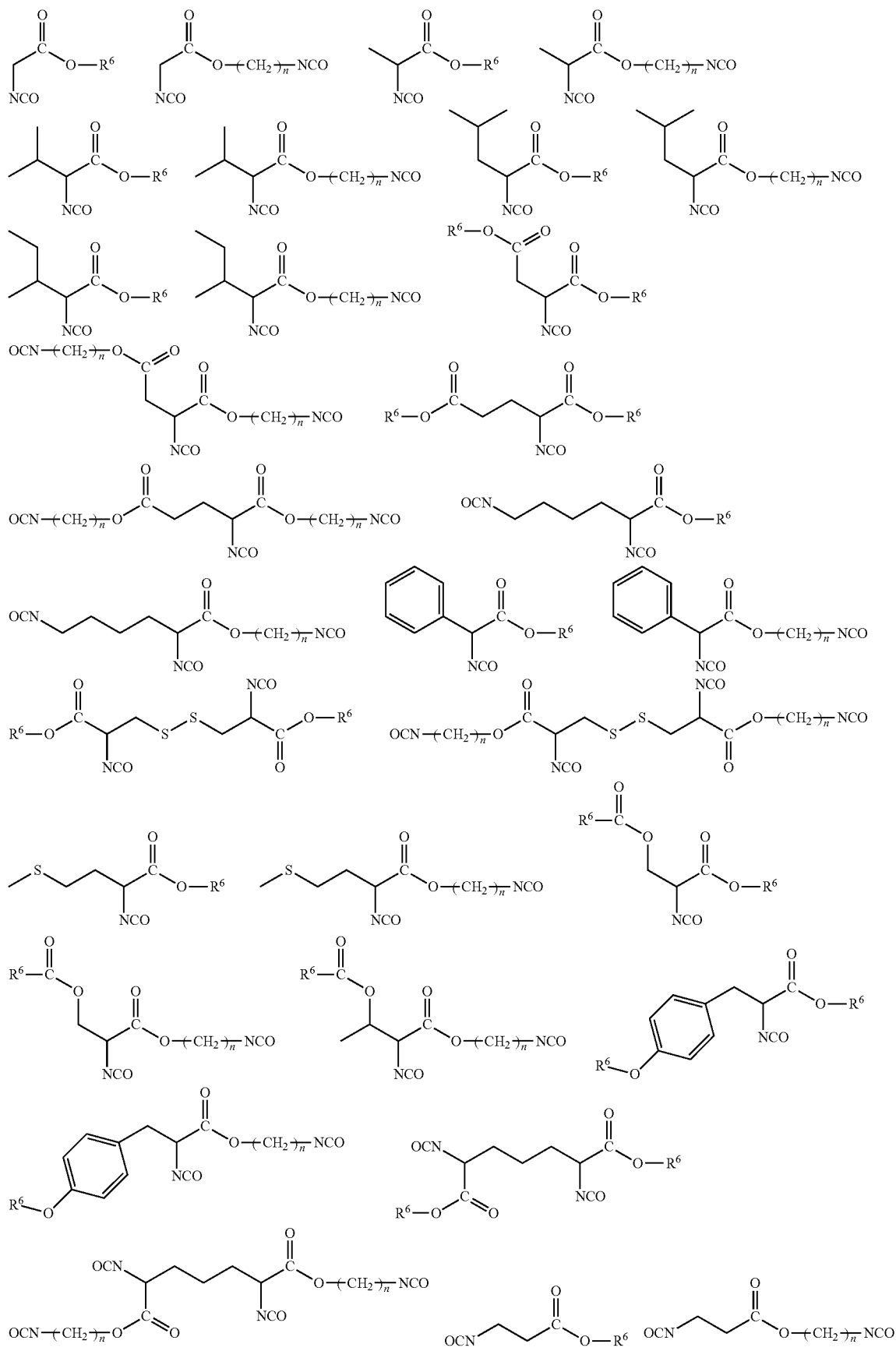

-continued

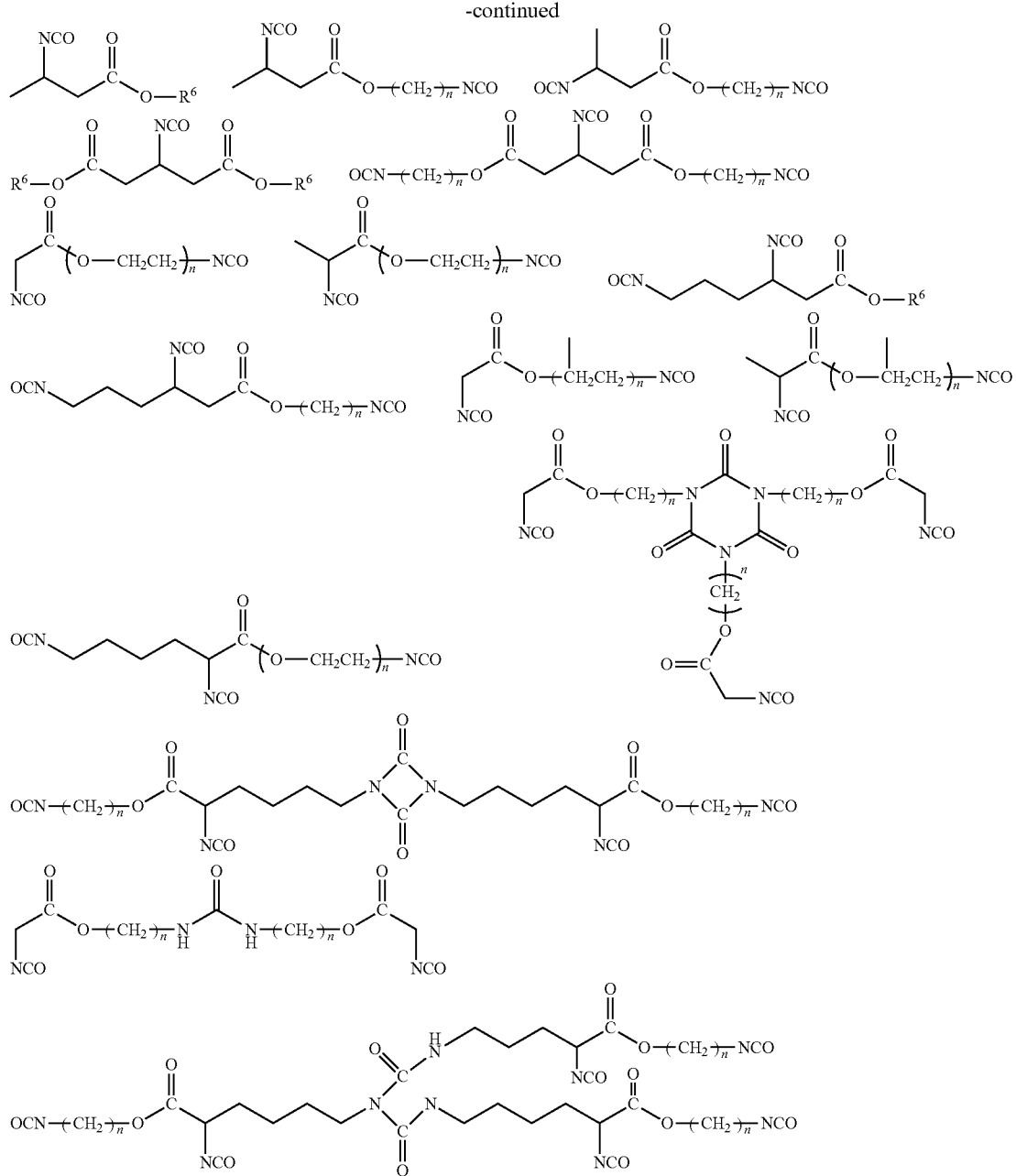

In the formulae, each R⁶ independently represents the same meaning as R², and n represents an integer of 1-4.

Among these, isocyanate compounds in which $R^2$ represents a methyl group, an ethyl group, a propyl group (including isomers), a butyl group (including isomers), a pentyl group (including isomers), a hexyl group (including isomers), or a 2-isocyanate ethyl group are preferable, from the viewpoint of the preferability in the application in which the weather resistance and the thermal yellowing resistance are required and industrially easy availability.

Among them, isocyanates derived from lysine skeleton, such as lysine diisocyanate methyl ester (LDI methyl ester), lysine diisocyanate ethyl ester (LDI ethyl ester), lysine diisocyanate phenyl ester (LDI phenyl ester), or lysine triisocyanate (LTI), isocyanates derived from glutamic acid skeleton, such as glutamic acid methyl ester isocyanate, or bis(2-isocyanatoethyl)2-isocyanato glutarate (GTI), or the like, are particularly preferable from the viewpoint of the high isocyanate reactivity, low volatility, and low viscosity.

The isocyanate compounds having the structure (A) and/or the structure (B) may be used alone or in combination of a plurality thereof, respectively.

The isocyanate according to the present embodiment may be a monofunctional isocyanate having an isocyanate group in a molecule thereof, a difunctional isocyanate having two isocyanate groups in a molecule thereof, or a trifunctional isocyanate having three isocyanate groups in a molecule thereof, and the number of isocyanate groups in a molecule thereof is not particularly limited. In a preferable embodiment of the isocyanate composition according to the present embodiment, the isocyanate composition containing at least one of the isocyanate compounds of the formula (1) and/or formula (2) contains a trifunctional isocyanate compound having three isocyanate groups in a molecule thereof, and, a difunctional isocyanate compound having two isocyanate groups in a molecule thereof, as the isocyanate compounds. In a more preferable embodiment of the isocyanate composition, the isocyanate composition contains a trifunctional isocyanate compound of formula (1) having three isocyanate groups in a molecule thereof, and, a difunctional isocyanate compound of formula (1) having two isocyanate groups in a molecule thereof. In another more preferable embodiment of the isocyanate composition, the isocyanate composition contains a trifunctional isocyanate compound of formula (2) having three isocyanate groups in a molecule thereof, and, a difunctional isocyanate compound of formula (2) having two isocyanate groups in a molecule thereof. In another more preferable embodiment of the isocyanate composition, the isocyanate composition contains a difunctional isocyanate compound of formula (1) having two isocyanate groups in a molecule thereof, and, a trifunctional isocyanate compound of formula (2) having three isocyanate groups in a molecule thereof.

An isocyanate with no less than trifunctionality reaches a crosslinking point generally easily in the reaction, and therefore exhibits strong advantages in terms of favorable drying properties and high coating strength when used as a coating material. However, when a bond is formed between molecules by reaction of isocyanate groups or reaction of isocyanate groups with a tiny amount of blend such as water during storing, the easy reachability to a crosslinking point thereof may bring disadvantages to cause an increase in the viscosity thereof. In the case of the composition containing a trifunctional isocyanate compound and a difunctional isocyanate compound, the difunctional isocyanate does not reach a crosslinking point even when isocyanate groups are reacted, and therefore exhibits advantageous in terms of suppression of an increase in the viscosity during storage. The combination of a trifunctional isocyanate in which $R^1$ and $R^2$ in the formula (1) and/or formula (2) have 1 or more isocyanate groups, respectively, and the total number of isocyanate groups in a molecule thereof is three, with a difunctional isocyanate in which $R^1$ has an isocyanate group and the total number of isocyanate groups in a molecule thereof is two is particularly preferable. In the case, $R^2$ in the difunctional isocyanate is preferably a group substituted with a substituent group such as an alkoxy, alkoxycarbonyl group, aromatic hydroxy group, or aromatic hydroxy carbonyl group. Specific examples thereof include: a combination of lysine triisocyanate (LTI) with lysine diisocyanate methyl ester (LDI methyl ester), a combination of lysine triisocyanate (LTI) with lysine diisocyanate ethyl ester (LDI ethyl ester), and a combination of lysine triisocyanate (LTI) with lysine diisocyanate phenyl ester (LDI phenyl ester).

In the composition containing the trifunctional isocyanate compound and the difunctional isocyanate compound, the amount of the difunctional isocyanate compound, relative to the total mass of the trifunctional isocyanate, is preferably $1.0 \times 10^2$ ppm by mass to 30% by mass, more preferably $5.0 \times 10^2$ ppm by mass to 10% by mass, and even more preferably $1.0 \times 10^3$ ppm by mass to 5% by mass.

It is preferable that the isocyanate compounds having the structure (A) and/or the structure (B) be prepared using the corresponding α-amino acid or β-amino acid as a raw material, from the viewpoint of decreased amount of impurities.

An amino acid prepared by a conventionally known method is preferably used as the amino acid. The amino acid may be prepared by fermentation or a chemical method (such as a method utilizing Strecker reaction). Although the amino acid obtained by fermentation is often L-form as a main component and the amino acid obtained by the chemical method is often DL-form, any thereof may be used. The amino acid may be purified into a form of a hydrochloride (—NH$_2$.HCl) at a moiety of an amino group, may be a commercially available product, or may have an amino group (—NH$_2$) free from hydrochloric acid, and any thereof may be used preferably. The amino acid is preferably prepared by fermentation, and has a purity of 90% or more. The purity is the ratio of the mass of the amino acid, relative to the total mass. The amino acid has more preferably a purity of 97% or more. It is preferable that the amino acid be further purified depending of the coloring properties of the product. The purity of the amino acid may be 99.5% or less, or 98% or less.

The isocyanate composition according to the present invention will be further explained precisely. The amount of the isocyanate compounds having the structure (A) and/or the structure (B) in the isocyanate composition, relative to the total mass of the isocyanate composition, is preferably 90% by mass or more. The amount is more preferably 97% by mass or more in view of the concentration of isocyanate groups. The amount of the isocyanate may be 99.5% by mass or less, and more preferably 98% by mass or less. The isocyanate composition may be diluted with a solvent or the like when used, and a diluted solution after storage is an embodiment according to the present invention. The composition may contain impurities derived from raw materials and/or impurities produced at the preparation process as by-products, the structure of which cannot be specified.

In the case where the isocyanate compound contains a specific stabilizer, preferably in an amount of 0.002 ppm by mass to 10% by mass, relative to the total mass of the isocyanates in the composition, the coloring-suppressibility and the stability when stored for a long time are improved.

The denaturation causing coloring or generation of gelatinous materials or solid contents when stored for a long time may be suppressed by formulating a specific amount of a specific stabilizer together with the isocyanate compound having the structure (A) and/or the structure (B) according to the present embodiment.

Preferable compounds to be contained as a stabilizer according to the present embodiment are described below.
<Compound of Formula (3)>

The isocyanate composition according to the present embodiment preferably contains a compound of formula (3) different from the isocyanate compound of the formula (1) and/or (2).

In the formula, $R^{13}$ represents an organic group with a valence of a, $R^{14}$ represents a monovalent organic group, and a represents an integer of 1 or 2.

In the formula (3), $R^{13}$ preferably represents a C1-10 aliphatic group, a C6-10 aromatic group, or a group of the following formula (3a), (3b), (3c) or (3d).

Specific examples of the aliphatic group include residual groups obtained by removing the number a of hydrogen atoms from C1-10 alkanes, such as methane, ethane, propane, butane, heptane, hexane, octane, nonane, or decane. Examples of the aromatic group include residual groups obtained by removing the number a of hydrogen atoms from compounds, such as benzene, methylbenzene, ethylbenzene, butylbenzene, octylbenzene, nonylbenzene, diphenyl, terphenyl, phenylpropyl benzene, di(phenylpropyl)benzene, or diphenylether. Among these, $R^{13}$ is preferably a residual group obtained by removing the number a of hydrogen atoms from a C1-10 alkane or benzene.

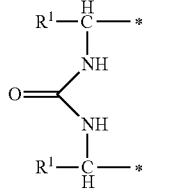
(3a)

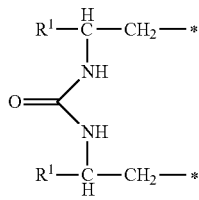
(3b)

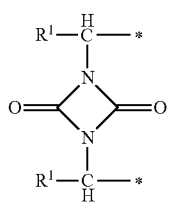
(3c)

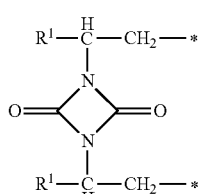
(3d)

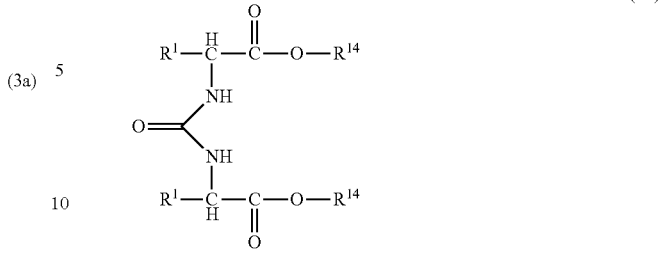
(32)

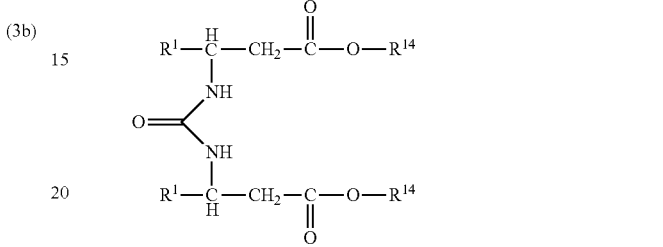
(33)

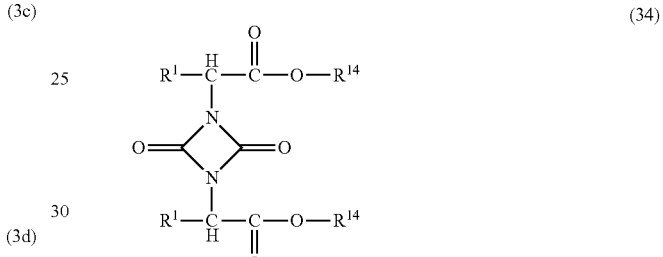
(34)

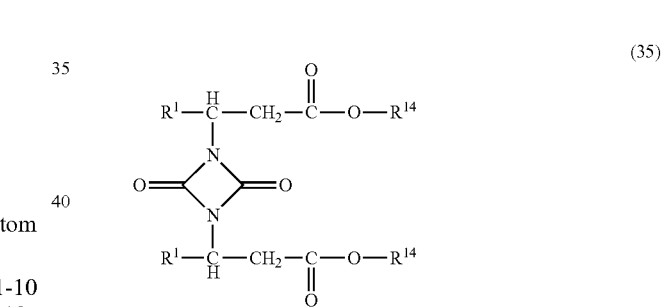
(35)

In the formulae, * represents a bond to a carbon atom constituting an ester bond in the formula (3).

In the formula (3), $R^{14}$ preferably represents a C1-10 aliphatic group or a C6-25 aromatic group. Specific examples of the aliphatic group include C1-10 alkyl groups, such as methyl, ethyl, propyl, butyl, heptyl, hexyl, octyl, nonyl, and decanyl. Examples of the aromatic group include compounds such as phenyl, methylphenyl, ethylphenyl, butylphenyl, octylphenyl, nonylphenyl, diphenyl, terphenyl, phenylpropyl benzene, di(phenylpropyl)benzene, and diphenylether. Among these, a C2-6 alkyl group or a phenyl group is preferable.

In view of the above-mentioned preferable $R^{13}$ and $R^{14}$, specific examples of the compound of formula (3) include ethyl acetate, butyl acetate, hexyl acetate, methyl propionate, ethyl butyrate, butyl butyrate, ethyl valerate, butyl valerate, ethyl hexanoate, ethyl octanoate, butyl caprate, phenyl acetate, benzyl acetate, methyl benzoate, ethyl benzoate, phenyl benzoate, benzyl benzoate, diethyl phthalate, dibutyl phthalate, and benzyl butyl phthalate.

As the compound of the formula (3), compounds having bonds of the following formula (32) to formula (35) derived from isocyanate groups included in the structure (A) of the formula (1) or the structure (B) of the formula (2) are preferably used.

In the formulae, $R^1$ and $R^{14}$ represent groups of the formula (1), formula (2), or formula (3).

In the case where the compound of formula (3) has the same structure as that of the isocyanate compound (compound of the formula (1) and/or the formula (2)), the compound is defined as the isocyanate compound of the formula (1) and/or the formula (2).

In the isocyanate composition according to the present embodiment, the amount of the compound of the formula (3), relative to the total mass of the compounds of the formula (1) and/or the formula (2), is 1.0 ppm by mass to 10% by mass, preferably 3.0 ppm by mass to $1.0 \times 10^3$ ppm by mass, more preferably 5.0 ppm by mass to $3.0 \times 10^3$ ppm by mass, and even more preferably 10 ppm by mass to $5.0 \times 10^3$ ppm by mass.

<Compound having an UV Absorption in an Area of Decamer or Higher Isocyanates in a Measurement Spectrum of Gel Permeation Chromatography>

A compound having an UV absorption in an area of decamer or higher isocyanates in a measurement spectrum of gel permeation chromatography (GPC) is preferably a compound having a 1-nylon body structure of the following formula (36) as the main skeleton thereof.

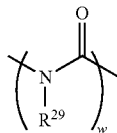
(36)

In the formula, $R^{29}$ represents a residual group obtained by removing an isocyanate group from a difunctional or more functional isocyanate compound, and w represents an integer of 1 or more. The terminal group thereof is not described.

An isocyanate constituting the compound having an UV absorption in an area of decamer or higher isocyanates in a measurement spectrum of gel permeation chromatography (GPC) may be an isocyanate of the formula (1) and/or the formula (2), or another isocyanate.

Preferable examples of isocyanates other than the isocyanates of the formula (1) and/or the formula (2) include: difunctional diisocyanate compounds such as C4-30 aliphatic diisocyanates, C8-30 alicyclic diisocyanates, and C8-30 aromatic group-containing diisocyanates, and specific examples thereof include: C4-30 aliphatic diisocyanates, such as 1,4-tetramethylene diisocyanate, 1,5-pentamethylene diisocyanate, 1,4-diisocyanato-2-methylbutane, 1,6-hexamethylene diisocyanate, 1,6-diisocyanato-2,5-dimethylhexane, 2,2,4-trimethyl-1,6-hexamethylene diisocyanate, lysine methyl ester diisocyanate, and lysine ethyl ester diisocyanate; C8-30 alicyclic diisocyanates, such as isophorone diisocyanate, 1,3-bis(isocyanate methyl)-cyclohexane, 4,4'-dicyclohexylmethane diisocyanate, hydrogenated tetramethylxylylene diisocyanate, and norbornene diisocyanate; and C8-30 aromatic group-containing diisocyanates, such as 4,4'-diphenylmethane diisocyanate, 2,6-tolylene diisocyanate, xylylene diisocyanate, tetramethylxylylene diisocyanate, and naphthalene diisocyanate. In the case where the compound has structural isomers, the structural isomers are encompassed in the above-mentioned examples.

Additional preferable examples of the isocyanate other than the isocyanates of the formula (1) and/or the formula (2) include: trifunctional diisocyanate compounds, such as 1,8-diisocyanate-4-isocyanate methyloctane, 1,3,6-triisocyanate hexane, 1,8-diisocyanato-4-(isocyanatomethyl)-2,4,7-trimethyloctane, 1,5-diisocyanato-3-(isocyanatomethyp-pentane, 1,6,11-triisocyanatoundecane, 1,4,7-triisocyanatoheptane, 1,2,2-triisocyanatobutane, 1,2,6-triisocyanatohexane, 1-isocyanato-2,2-bis(isocyanatomethyl)butane, 1,3,5-triisocyanatocyclohexane, 1,7-diisocyanato-4-(3-isocyanatopropyl)heptane, 1,3-diisocyanato-2-(isocyanatomethyl)-2-methylpropane, 1,3,5-triisocyanatobenzene, 1,3,5-triisocyanato-2-methylbenzene, 1,3,5-tris(1-isocyanatopropane-2-yl)benzene, 1,3,5-tris(1-isocyanatopropane-2-yl)-2-methylbenzene, 1,3,5-tris(1-isocyanatomethyl)-2-methylbenzene, and 2,2'-((2-isocyanato-1,3-phenylene)bis(methylene))bis(isocyanatebenzene).

The compound having an UV absorption in the area of decamer or higher isocyanates in a measurement spectrum of gel permeation chromatography (GPC) exhibits a peak of UV absorption at the wavelength of 254 nm in the area of decamer or higher isocyanates when GPC is conducted using tetrahydrofuran as a developing solvent and polystyrene as a molecular weight analytical standard substance. In the case where the isocyanate composition does not contain any monofunctional isocyanate compounds, the amount of the compound having an UV absorption in the area of decamer or higher isocyanates in the measurement spectrum of gel permeation chromatography (GPC), relative to the total mass of difunctional or more functional isocyanate compounds in the isocyanate composition, is measured. Specifically, the GPC is equipped with a UV detector and a differential refractometer (the UV detector and the differential refractometer may be connected in parallel or in series), and the amount is calculated by (B)/(A) using the peak area (A) corresponding to difunctional or more functional isocyanate compounds in the differential refractive index, and the peak area (B) corresponding to a compound having a UV absorption (at the wavelength of 254 nm) in the area of decamer or higher isocyanates in the measurement spectrum of the gel permeation chromatography.

In the case where a monofunctional isocyanate compound is contained in the isocyanate composition, the amount of the compound having an UV absorption in an area of decamer or higher isocyanates in the measurement spectrum of gel permeation chromatography (GPC), relative to the total mass of isocyanate compounds, is calculated by (B)/(A) from the peak area (A) corresponding to monofunctional or more functional isocyanate compounds in the differential refractive index, and the peak area (B) corresponding to a compound having a UV absorption (at the wavelength of 254 nm) in the area of decamer or higher isocyanates in the measurement spectrum of the gel permeation chromatography, the GPC being equipped with a UV detector and a differential refractometer (the UV detector and the differential refractometer may be connected in parallel or in series).

The amount of the compound having an UV absorption in an area of decamer or higher isocyanates in a measurement spectrum of gel permeation chromatography (GPC), relative to the total mass of isocyanate compounds in the isocyanate composition, is 1.0 ppm by mass to 10% by mass, more preferably 3.0 ppm by mass to $3.0 \times 10^3$ ppm by mass, and even more preferably 10 ppm by mass to $1.0 \times 10^3$ ppm by mass.

<Compound Containing Isocyanurate Group and/or Biuret Group>

A compound containing an isocyanurate group and/or a biuret group is a compound having a group of the following formula (6') or formula (7').

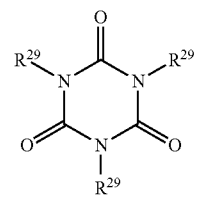
(6')

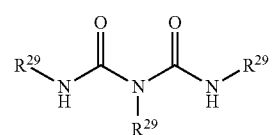
(7')

In the formulae, $R^{29}$ represents a residual group obtained by removing an isocyanate group from a difunctional or more functional isocyanate compound.

Although an isocyanate constituting the compound having an isocyanurate group and/or a biuret group may be an isocyanate of the formula (1) and/or the formula (2), or another isocyanate, the isocyanate is preferably an isocyanate other than the isocyanate of the formula (1) and/or the formula (2). As the isocyanate other than the isocyanate of the formula (1) and/or the formula (2), the isocyanates exemplified in the description of the <compound having an UV absorption in an area of decamer or higher isocyanates in a measurement spectrum of gel permeation chromatography> are preferably used.

The amount of the compound containing an isocyanurate group and/or a biuret group in the isocyanate composition may be the additive amount of a compound containing an isocyanurate group and/or a biuret group, or the amount obtained by quantitative analysis by GPC using tetrahydrofuran as a developing solvent. Specific examples of the method of the quantitative analysis by GPC include the method in which the GPC is equipped with a differential refractometer, and the ratio (B)/(A) is calculated from the peak area (A) corresponding to the isocyanate compound of the formula (1) and/or the formula (2) in the differential refractive index, and the peak area (B) corresponding to the compound containing an isocyanurate group and/or a biuret group.

The amount of the compound containing an isocyanurate group and/or a biuret group, relative to the total mass of isocyanate compounds in the isocyanate composition, is preferably 1.0 ppm by mass to 10% by mass, more preferably 3.0 ppm by mass to $3.0 \times 10^3$ ppm by mass, and even more preferably 10 ppm by mass to $1.0 \times 10^3$ ppm by mass.

<Saturated and/or Unsaturated Hydrocarbon Compound having a Linear-Chain, Branched-Chain, or Cyclic Structure (may be referred to as Compound A)>

As compounds having unsaturated bond between carbon atoms, aliphatic hydrocarbon compounds having a linear-chain, branched-chain, or cyclic structure, and aromatic hydrocarbon compounds which may have a substituent group constituted by hydrocarbon groups, compounds of the following formula (37) or C5-20 hydrocarbon compounds are preferable.

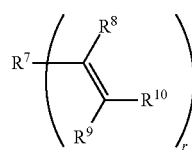

(37)

In the formula (37), $R^7$, $R^8$, $R^9$ and $R^{10}$ each independently represent a hydrogen atom, a halogen atom or a C1-10 organic group, provided that all of $R^7$ to $R^{10}$ do not simultaneously represent hydrogen atoms, r represents 1 when $R^7$ represents a hydrogen atom or a halogen atom, and r represents an integer of 1 to 3 when $R^7$ represents a C1-10 organic group.

$R^8$ to $R^{10}$ preferably represent a hydrogen atom or a C1-10 organic group, respectively. In the case where $R^8$ to $R^{10}$ represent organic groups, C1-10 aliphatic groups or C6-10 aromatic groups are preferable. As such $R^8$ to $R^{10}$, alkyl groups, such as a methyl group, an ethyl group, a propyl group, a butyl group, a pentyl group, a hexyl group, a heptyl group, an octyl group, a nonyl group, a decyl group, and structural isomers thereof; chain alkyloxy groups, such as a methyloxy group, an ethyloxy group, a propyloxy group, a butyloxy group, a pentyloxy group, a hexyloxy group, a heptyloxy group, an octyloxy group, a nonyloxy group, a decyloxy group, and structural isomers thereof; cycloalkyl groups, such as a cyclopentyl group, a cyclohexyl group, a cycloheptyl group, a cyclooctyl group, a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; groups constituted by chain alkyl groups and cycloalkyl groups; groups faulted by removing a hydrogen atom from aromatic compounds such as benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof, are mentioned. Among these, it is preferable that $R^8$ to $R^{10}$ each independently represent a hydrogen atom or a C1-10 alkyl group.

$R^7$ preferably represents a hydrogen atom or a C1-10 organic group. In the case where $R^7$ represents an organic group, $R^7$ preferably represents a C1-10 aliphatic group or C6-10 aromatic group. As such $R^7$, groups obtained by removing the number r of hydrogen atoms from alkanes, such as methane, ethane, propane, butane, pentane, hexane, heptane, octane, nonane, decane, and structural isomers thereof; groups obtained by removing the number r of hydrogen atoms from cycloalkanes, such as cyclopentane, cyclohexane, cyclopentane, and cyclooctane; groups obtained by removing the number r of hydrogen atoms from chain alkyl group-substituted cycloalkanes, such as methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, dibutylcyclohexane, and structural isomers thereof; groups obtained by removing the number r of hydrogen atoms from aromatic compounds, such as benzene, toluene, ethylbenzene, propylbenzene, butylbenzene, hexylbenzene, octylbenzene, naphthalene, dimethylbenzene, diethylbenzene, dipropylbenzene, dibutylbenzene, dihexylbenzene, dioctylbenzene, methylnaphthalene, ethylnaphthalene, butylnaphthalene, and structural isomers thereof, are mentioned. Among these, $R^7$ preferably represents a group obtained by removing the number r of hydrogen atoms from a C1-10 alkane or a benzene.

Examples of the compound of formula (37) include: propene, butene, pentene, 2-methylbutene, 2,4,4-trimethylpentene-1, hexene, octene, nonene, decene, hexadecene, octadecene, butadiene, pentadiene, hexadiene, chloroethylene, chloropropene, chlorobutene, chloropentene, chlorohexene, chlorooctene, chlorononene, chlorodecene, chlorohexadecene, chlorooctadecene, chlorobutadiene, chloropentadiene, chlorohexadiene, dichloroethylene, dichloropropene, dichlorobutene, dichloropentene, dichlorohexene, dichlorooctene, dichlorononene, dichlorodeeene, dichlorohexadecene, dichlorooctadecene, dichlorobutadiene, dichloropentadiene, dichlorohexadiene, bromoethylene, bromopropene, bromobutene, bromopentene, bromohexene, bromooctene, bromononene, bromodecene, bromohexadecene, bromooctadecene, bromobutadiene, bromopentadiene, bromohexadiene, dibromoethylene, dibromopropene, dibromobutene, dibromopentene, dibromohexene, dibromooctene, dibromononene, dibromodecene, dibromohexadecene, dibromooctadecene, dibromobutadiene, dibromopentadiene, dibromohexadiene, fluoroethylene, fluoropropene, fluorobutene, fluoropentene, fluorohexene, fluorooctene, fluorononene, fluorodecene, fluorohexadecene, fluorooctadecene, fluorobutadiene, fluoropentadiene, fluorohexadiene, difluoro ethylene, difluoropropene, difluorobutene, difluoropentene, difluorohexene, difluorooctene, difluorononene, difluorodecene, difluorohexadecene, difluorooctadecene, difluorobutadiene, difluoropentadiene, difluorohexadiene, styrene, propenylbenzene, isopropenylbenzene (also referred to as "α-methylstyrene"), allylbenzene, phenylbutadiene, divinylbenzene, stilbene, vinylanisole, propenylanisole, anilanisole, isoanethole, elemicin, asarone, chlorostyrene, chloropropenylbenzene, chloroisopropenylbenzene, chloroallylbenzene, chlorophenylbutadiene, chlorodivinylbenzene, chlorostilbene, chlorovinylanisole, chloropropenylanisole, chloroanilanisole, chloroisoanethole, chloroelemicin, chloroasarone, bromo styrene, bromopropenylbenzene, bromoisopropenylbenzene, bromoallylbenzene, bromophenylbutadiene, bromodivinylbenzene, bromostilbene, bromovinylanisole, bromopropenylani sole, bromoanilanisole, bromoisoanethole, bromoelemicin, bromoasarone, fluoro styrene, fluoropropenylbenzene, fluoroisopropenylbenzene, fluoroallylbenzene, fluorophenylbutadiene, fluorodivinylbenzene, fluorostilbene, fluorovinylanisole, fluoropropenylanisole, fluoroanilanisole, fluoroisoanethole, fluoroelemicin, fluoroasarone, dichlorostyrene, dichloropropenylbenzene, dichloroisopropenylbenzene, dichloroallylbenzene, dichlorophenylbutadiene, dichlorodivinylbenzene, dichlorostilbene, dichlorovinylanisole, dichloropropenylanisole, dichloroanilanisole, dichloroisoanethole, dichloroelemicin, dichloroasarone, dibromostyrene, dibromopropenylbenzene, dibromoisopropenylbenzene, dibromoallylbenzene, dibromophenylbutadiene, dibromodivinylbenzene, dibromostilbene, dibromovinylanisole, dibromopropenylanisole, dibromoanilanisole, dibromoisoanethole, dibromoelemicin, dibromoasarone, difluoro styrene, difluoropropenylbenzene, difluoroisopropenylbenzene, difluoroallylbenzene, difluorophenylbutadiene, difluorodivinylbenzene, difluorostilbene, difluorovinylanisole, difluoropropenylanisole, difluoroanilanisole, difluoroisoanethole, difluoroelemicin, difluoroasarone, and structural isomers thereof. Among these, from the viewpoint of thermal stability, a compound free from a halogen atom is preferably used, and α-methylstyrene is more preferably used.

Specific examples of the C5-20 hydrocarbon compound include pentane, hexane, heptane, octane, nonane, decane, dodecane, tetradecane, pentadecane, hexadecane, octadecane, nonadecane, cyclopentane, cyclohexane, cycloheptane, cyclooctane, methylcyclopentane, ethylcyclopentane, methylcyclohexane, ethylcyclohexane, propylcyclohexane, butylcyclohexane, pentylcyclohexane, hexylcyclohexane, dimethylcyclohexane, diethylcyclohexane, dibutylcyclohexane, and structural isomers thereof, and benzene, toluene, ethylbenzene, butylbenzene, pentylbenzene, hexylbenzene, octylbenzene, biphenyl, terphenyl, diphenylethane, (methylphenyl)phenylethane, dimethylbiphenyl, benzyltoluene, naphthalene, methylnaphthalene, ethylnaphthalene, butylnaphthalene, and structural isomers thereof. Among these, C5-15 alkanes and benzyltoluene are preferable.

The amount of the compound, relative to the total mass of the isocyanate compound in the composition, is preferably 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Compound having at Least One Bond Selected from the Group Consisting of an Ether Bond and a Thioether Bond (may be Referred to as Compound B)>

The compound having at least one bond selected from the group consisting of an ether bond and a thioether bond may be a compound having: either an ether bond or a thioether bond; and aliphatic hydrocarbon groups, wherein the same kind or different kinds of aliphatic hydrocarbon compounds are bonded via an ether bond or a thioether bond, a compound having: either an ether bond or a thioether bond; and aromatic hydrocarbon groups, wherein the same kind or different kinds of aromatic hydrocarbon compounds are bonded via an ether bond or a thioether bond, or a compound having: either an ether bond or a thioether bond; an aliphatic hydrocarbon group; and an aromatic hydrocarbon group. The compound having at least one bond selected from the group consisting of an ether bond and a thioether bond (compound B) is preferably a compound having 2-20 carbon atoms. Specific examples thereof include: ethers in which hydrocarbon compounds are bonded via an ether bond, such as ethyl ether, butyl ether, octyl ether, nonyl ether, decyl ether, methyl ethyl ether, methyl butyl ether, methyl octyl ether, methyl nonyl ether, methyl decyl ether, ethyl butyl ether, ethyl octyl ether, ethyl nonyl ether, ethyl decyl ether, butyl octyl ether, butyl nonyl ether, butyl decyl ether, octyl nonyl ether, octyl decyl ether, dicyclopentyl ether, dicyclohexyl ether, dicyclooctyl ether, cyclohexyl ethyl ether, cyclohexyl butyl ether, cyclohexyl octyl ether, cyclohexyl nonyl ether, cyclohexyl decyl ether, tetraethylene glycol dimethyl ether, and structural isomers thereof; thioethers in which hydrocarbon compounds are bonded via a thioether (sulfide) bond, such as ethyl sulfide, butyl sulfide, octyl sulfide, nonyl sulfide, decyl sulfide, methyl ethyl sulfide, methyl butyl sulfide, methyl octyl sulfide, methyl nonyl sulfide, methyl decyl sulfide, ethyl butyl sulfide, ethyl octyl sulfide, ethyl nonyl sulfide, ethyl decyl sulfide, butyl octyl sulfide, butyl nonyl sulfide, butyl decyl sulfide, octyl nonyl sulfide, octyl decyl sulfide, dicyclopentyl sulfide, dicyclohexyl sulfide, dicyclooctyl sulfide, cyclohexyl ethyl sulfide, cyclohexyl butyl sulfide, cyclohexyl octyl sulfide, cyclohexyl nonyl sulfide, cyclohexyl decyl sulfide, and structural isomers thereof; aromatic ethers in which aromatic hydrocarbon compounds are bonded via an ether bond, such as diphenyl ether, (methylphenyl)-phenyl ether, (ethylphenyl)-phenyl ether, (butyl phenyl)-phenyl ether, (hexylphenyl)-phenyl ether, (methylphenyl)ether, (ethylphenyl)ether, (butylphenyl)ether, (hexylphenyl)ether, dibenzyl ether, di(methylbenzyl)ether, di(ethylbenzyl)ether, di(butylbenzyl)ether, di(pentylbenzyl)ether, di(hexylbenzyl)ether, di(octylbenzyl)ether, diphenyl ether, and structural isomers thereof; aromatic thioethers in which aromatic hydrocarbon compounds are bonded via a thioether bond, such as diphenyl sulfide, (methylphenyl)-phenyl sulfide, (ethylphenyl)-phenyl sulfide, (butylphenyl)-phenyl sulfide, (hexylphenyl)-phenyl sulfide, (methylphenyl)sulfide, (ethylphenyl)sulfide, (butylphenyl)sulfide, (hexylphenyl)sulfide, di(methylbenzyl)sulfide, di(ethylbenzyl)sulfide, di(butylbenzyl)sulfide, di(pentylbenzyl)sulfide, di(hexylbenzyl)sulfide, di(octylbenzyl)sulfide, diphenyl sulfide, dibenzyl sulfide, and structural isomers thereof; phenylmethyl ether, phenylethyl ether, phenylbutyl ether, phenyloctyl ether, phenylnonyl ether, phenyldecyl ether, benzylethyl ether, benzylbutyl ether, benzyloctyl ether, benzylnonyl ether, benzyldecyl ether, (methylphenyl)ethyl ether, (methylphenyl)butyl ether, (methylphenyl)octyl ether, (methylphenyl)nonyl ether, (methylphenyl)decyl ether, (ethylphenyl)ethyl ether, (ethylphenyl)butyl ether, (ethylphenyl)octyl ether, (ethylphenyl)

nonyl ether, (ethylphenyl)decyl ether, (butylphenypethyl ether, (butylphenyl)butyl ether, (butylphenyl)octyl ether, (butylphenyl)nonyl ether, (butylphenyl)decyl ether, and structural isomers thereof. Among these, diphenyl ether or dibenzyl ether is preferable.

The amount of the compound having at least one bond selected from the group consisting of an ether bond and a thioether bond, relative to the total mass of the isocyanate compound in the composition, is preferably 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Carbamate Group-Containing Compound (which may be Referred to as Compound C)>

A carbamate group-containing compound (compound C) is preferably a carbamate compound in which a hydroxy compound is added to at least one isocyanate group in the isocyanate compound having the structure (A) and/or the structure (B). The hydroxy compound may be an alcohol or an aromatic hydroxy compound. As the alcohol, an alcohol having one or two alcoholic hydroxy groups (hydroxy groups directly added to carbon atoms other than an aromatic ring constituting the hydroxy compound) is preferable due to the low viscosity, and a monoalcohol having an alcoholic hydroxy group is more preferable. In addition, from the viewpoint of easy availability or the solubility of raw materials or resultant products, C1-20 alkyl alcohols are preferable. The aromatic hydroxy compound may be used industrially, and, form the viewpoint of general low viscosity, monovalent to trivalent aromatic hydroxy compounds (that is, the number of hydroxy groups bonded to an aromatic ring is an integral number of 1 to 3) are preferable, and monovalent aromatic hydroxy compounds are more preferable. A substituent group which substitutes an aromatic hydrocarbon ring of the aromatic hydroxy compound is preferably a group selected from the group consisting of acyclic hydrocarbon groups and cyclic hydrocarbon groups (monocyclic hydrocarbon groups, condensed polycyclic hydrocarbon groups, cross-linked cyclic hydrocarbon groups, Spiro hydrocarbon groups, ring-assembly hydrocarbon groups, and side chain-containing cyclic hydrocarbon groups), or a group in which at least one group selected from the above-mentioned group is bonded (mutually-substituted group), in view of the difficulty in occurrence of side reactions.

Specifically, a carbamate compound in which a hydroxy compound mentioned as $R^2OH$ in paragraphs [0064] to [0081] of International Patent Application Publication No. WO 2014/069605 pamphlet is added to at least one isocyanate group in the isocyanate compound having the structure (A) and/or the structure (B) is preferably used as the carbamate group-containing compound (compound C) according to the present embodiment.

Specifically, in the case where a group obtained by removing a hydroxy group form a hydroxy compound (R" group when the hydroxy compound is represented by R"OH) is an aliphatic hydrocarbon group, the group is an aliphatic hydrocarbon group in which atoms other than hydrogen atoms constituting the group are specific nonmetallic atoms (such as carbon, oxygen, nitrogen, sulfur, silicon, or halogen atoms). Preferable examples of the aliphatic group include chain hydrocarbon groups, cyclic hydrocarbon groups, and groups bonded with at least one group selected from the group consisting of chain hydrocarbon groups and cyclic hydrocarbon groups (such as cyclic hydrocarbon groups substituted with chain hydrocarbon groups, or chain hydrocarbon group substituted with cyclic hydrocarbon groups). Examples of an aliphatic group substituted with an aromatic group include: chain alkyl groups, cycloalkyl groups substituted with aromatic groups, and C1-44 alkyl groups substituted with C6-49 aromatic groups. The aromatic group is preferably an aromatic group in which atoms other than hydrogen atoms constituting the aromatic group are specific nonmetallic atoms (such as carbon, oxygen, nitrogen, sulfur, silicon, or halogen atom), and examples thereof include monocyclic aromatic group, condensed polycyclic aromatic group, cross-linked cyclic aromatic group, ring-assembly aromatic group, and heterocyclic aromatic group, and more preferable examples thereof include substituted or unsubstituted phenyl groups, substituted or unsubstituted naphthyl groups, and substituted or unsubstituted anthryl groups. Specific examples thereof include: chain alkyl groups such as a methyl group, an ethyl group, a propyl group, a butyl group, a pentyl group, a hexyl group, a heptyl group, an octyl group, a nonyl group, a decyl group, a dodecyl group, an octadecyl group, and structural isomers thereof; cycloalkyl groups such as a cyclopentyl group, a cyclohexyl group, a cycloheptyl group, a cyclooctyl group, and structural isomers thereof; groups constituted by chain alkyl groups and cycloalkyl groups, such as a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; and aralkyl groups such as a phenylmethyl group, a phenylethyl group, a phenylpropyl group, a phenylbutyl group, a phenylpentyl group, a phenylhexyl group, a phenylheptyl group, a phenyloctyl group, a phenylnonyl group, and structural isomers thereof.

Specific examples of a hydroxy compound (R"OH) include: unsubstituted alkyl alcohols such as methyl alcohol, ethyl alcohol, propyl alcohol, butyl alcohol, pentyl alcohol, hexyl alcohol, heptyl alcohol, octyl alcohol, nonyl alcohol, decyl alcohol, dodecyl alcohol, octadecyl alcohol and structural isomers thereof; unsubstituted cycloalkyl alcohols such as cyclopentyl alcohol, cyclohexyl alcohol, cycloheptyl alcohol, cyclooctyl alcohol and structural isomers thereof; alcohols constituted by chain alkyl groups and cycloalkyl alcohols, such as methylcyclopentyl alcohol, ethylcyclopentyl alcohol, methylcyclohexyl alcohol, ethylcyclohexyl alcohol, propylcyclohexyl alcohol, butylcyclohexyl alcohol, pentylcyclohexyl alcohol, hexylcyclohexyl alcohol, dimethylcyclohexyl alcohol, diethylcyclohexyl alcohol, dibutylcyclohexyl alcohol and structural isomers thereof; alkyl alcohols substituted with aromatic groups, such as phenylmethyl alcohol, phenylethyl alcohol, phenylpropyl alcohol, phenylbutyl alcohol, phenylpentyl alcohol, phenylhexyl alcohol, phenylheptyl alcohol, phenyloctyl alcohol, phenylnonyl alcohol and structural isomers thereof. Among these, C1-20 alkyl alcohols are preferably used from the viewpoint of easy availability, solubility of raw materials or resultant products, or the like.

In the case where a group obtained by removing a hydroxy group from the hydroxy compound (group R" when the hydroxy compound is represented by R"OH) is an aromatic group, that is, the hydroxy compound (R"OH) is an aromatic hydroxy compound, monovalent to trivalent aromatic hydroxy compounds (that is, the number of hydroxy groups bonded to an aromatic ring is an integral number of 1 to 3) are preferable in terms of industrial availability and generally low viscosity. Examples of the aromatic hydroxy compound include compounds of the following formula (X).

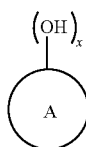

(X)

In the formula (X), the ring A represents an aromatic hydrocarbon ring which may have substituent groups, the ring A may be monocyclic or polycyclic, and x represents an integer of 1 to 3.

Among the aromatic hydroxy compounds of the formula (X), a monovalent aromatic hydroxy compound wherein x represents 1 is more preferable.

The substituent groups on the aromatic hydrocarbon ring are selected from the group consisting of halogen atoms, aliphatic groups and aromatic groups, and examples thereof include cyclic groups such as cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, and side chain-containing cyclic hydrocarbon group), heterocyclic groups, heterocyclic spiro groups, and hetero cross-linked cyclic groups, acyclic hydrocarbon groups, and groups bonded with at least one group selected from the group consisting of acyclic hydrocarbon groups and cyclic groups.

Among these substituent groups, the substituent groups preferably used according to the present embodiment in view of the difficulty in occurrence of side reactions are groups selected from the group consisting of acyclic hydrocarbon groups, cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, and side chain-containing cyclic hydrocarbon group) or groups bonded with at least one group selected from the above-mentioned group (groups mutually substituted).

Substituent groups that substitute the ring A are groups selected from the group consisting of alkyl groups, cycloalkyl groups, aryl groups, aralkyl groups, and ether groups (substituted or unsubstituted, alkyl ethers, aryl ethers or aralkyl ethers); groups bonded with groups selected from the above-mentioned group; groups selected from groups constituted by groups in which the at least a group selected from the above-mentioned group is bonded with a saturated hydrocarbon bond or an ether bond; or halogen atoms, provided that the sum of the number of carbon atoms constituting the ring A and the number of carbon atoms constituting all substituent groups that substitute the ring A is an integer of 6 to 50.

Examples of the ring A include a benzene ring, a naphthalene ring, an anthracene ring, a phenanthrene ring, a naphthacene ring, a chrysene ring, a pyrene ring, a triphenylene ring, a pentalene ring, an azulene ring, a heptalene ring, an indacene ring, a biphenylene ring, an acenaphthylene ring, an aceanthrylene ring, and an acephenanthrylene ring, and preferable examples thereof include a structure containing at least one structure selected from a benzene ring and a naphthalene ring.

From the viewpoint of industrial use, an aromatic hydroxy compound having an easily-available benzene ring as a skeleton is preferable. Examples of the aromatic hydroxy compound include an aromatic hydroxy compound of the following formula (X-1).

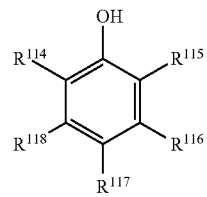

(X-1)

In the formula, $R^{114}$, $R^{115}$, $R^{116}$, $R^{117}$ and $R^{118}$ each independently represent a group selected from the group consisting of a chain alkyl group, a cycloalkyl group, an aryl group, an aralkyl group, and an ether group (substituted or unsubstituted alkyl ether, aryl ether, or aralkyl ether); a group bonded with at least one group selected from the above-mentioned group; a group selected from the group consisting of groups in which at least one group selected from the above-mentioned group is bonded with a saturated aliphatic bond or an ether bond; a halogen atom; or a hydrogen atom, and the sum of the number of carbon atoms constituting $R^{114}$ to $R^{118}$ is an integer of 0 to 44.

In the formula (X-1), preferred $R^{114}$ to $R^{118}$ are groups independently selected from groups shown in the following (i) to (v):

(i) hydrogen atom;
(ii) halogen atoms;
(iii) C1-44 carbon functional groups in which a carbon atom at the position a bonds with a group selected from the group consisting of C1-43 chain alkyl groups, C1-43 cycloalkyl groups, C1-43 alkoxy groups, C2-43 polyoxyalkylene alkyl ether groups free from a hydroxy group at the terminal end thereof, C6-43 aryl groups, C7-43 aralkyl groups, and C7-43 aralkyloxy groups;
(iv) C1-44 aromatic groups, bonded with at least one group selected from the group consisting of a hydrogen atom, C1-38 chain alkyl groups, C4-38 cycloalkyl groups, C1-38 alkoxy groups, C2-38 polyoxyalkylene alkyl ether groups free from a hydroxy group at the terminal thereof, C6-38 aromatic groups, C7-38 aralkyl groups, C7-38 aralkyloxy groups, and groups bonded with at least one of the above-mentioned groups;
(v) C1-44 oxygen functional groups, bonded with C1-44 alkyl groups, C1-44 cycloalkyl groups, C1-44 alkoxy groups, C2-44 polyoxyalkylene alkyl ether groups free from a hydroxy group at the terminal thereof, C6-44 aromatic groups, C7-44 aralkyl groups, C7-44 aralkyloxy groups, or groups bonded with at least one of the above-mentioned groups.

Here, the term "aralkyloxy group" means a group in which an oxygen atom is bonded to the aralkyl group defined above.

Examples of $R^{114}$ to $R^{118}$ include: chain alkyl groups, such as a methyl group, an ethyl group, a propyl group, a butyl group, a pentyl group, a hexyl group, a heptyl group, an octyl group, a nonyl group, a decyl group, a dodecyl group, an octadecyl group, and structural isomers thereof; cycloalkyl groups, such as a cyclopentyl group, a cyclohexyl group, a cycloheptyl group, and a cyclooctyl group; groups constituted by chain alkyl groups and cycloalkyl groups, such as a methylcyclopentyl group, an ethylcyclopentyl group, a methylcyclohexyl group, an ethylcyclohexyl group, a propylcyclohexyl group, a butylcyclohexyl group, a pentylcyclohexyl group, a hexylcyclohexyl group, a dimethylcyclohexyl group, a diethylcyclohexyl group, a dibutylcyclohexyl group, and structural isomers thereof; chain alkyloxy groups, such as a methoxy group, an ethoxy group, a propoxy group, a butyloxy group, a pentyloxy group, a hexyloxy group, a heptyloxy group, an octyloxy group, a nonyloxy group, a decyloxy group, a dodecyloxy group, an octadecyloxy group, and structural isomers thereof; cycloalkyloxy groups, such as a cyclopentyloxy group, a cyclohexyloxy group, a cycloheptyloxy group, and a cyclooctyloxy group; alkyloxy groups corresponding to groups constituted by chain alkyl groups and cycloalkyl groups, such as a methylcyclopentyloxy group, an ethylcyclopentyloxy group, a methylcyclohexyloxy group, an ethycyclohexyloxy group, a propyl cyclohexyloxy group, a butylcyclohexyloxy group, a pentylcyclohexyloxy group, a hexylcyclohexyloxy group, a dimethylcyclohexyloxy group, a diethylcyclohexyloxy group, a dibutylcyclohexyloxy group, and structural isomers thereof; aromatic groups, such as a phenyl group, a methylphenyl group, an ethylphenyl group, a propylphenyl group, a butylphenyl group, a pentylphenyl group, a hexylphenyl group, a heptylphenyl group, an octylphenyl group, a nonylphenyl group, a decylphenyl group, a biphenyl group, a dimethylphenyl group, a diethylphenyl group, a dipropylphenyl group, a dibutylphenyl group, a dipentylphenyl group, a dihexylphenyl group, a diheptylphenyl group, a terphenyl group, a trimethylphenyl group, a triethylphenyl group, a tripropylphenyl group, a tributylphenyl group, and structural isomers thereof; groups constituted by aromatic groups and alkyl groups, such as a 1-methyl-1-phenylethyl group, and a 1-phenylethyl group; aromatic-oxy groups, such as a phenoxy group, a methylphenoxy group, an ethylphenoxy group, a propylphenoxy group, a butylphenoxy group, an octylphenoxy group, a nonylphenoxy group, a decylphenoxy group, a phenylphenoxy group, a dimethylphenoxy group, a diethylphenoxy group, a dipropylphenoxy group, a dibutylphenoxy group, a dipentylphenoxy group, a dihexylphenoxy group, a diheptylphenoxy group, a diphenylphenoxy group, a trimethylphenoxy group, a triethylphenoxy group, a tripropylphenoxy group, a tributylphenoxy group, and structural isomers thereof; aralkyl groups, such as a phenylmethyl group, a phenylethyl group, a phenylpropyl group, a phenylbutyl group, a phenylpentyl group, a phenylhexyl group, a phenylheptyl group, a phenyloctyl group, and a phenylnonyl group; and aralkyloxy groups, such as a phenylmethoxy group, a phenylethoxy group, a phenylpropyloxy group, a phenylbutyloxy group, a phenylpentyloxy group, a phenylhexyloxy group, a phenylheptyloxy group, a phenyloctyloxy group, a phenylnonyloxy group, and structural isomers thereof. Among these, it is preferable that $R^{114}$ to $R^{118}$ represent a hydrogen atom, a C1-10 alkyl group such as a methyl group, a butyl group, or an octyl group, a phenoxy group, a cumyl group, or structural isomers thereof.

It is preferable that the amount of the carbamate group-containing compound, relative to the total mass of the isocyanate compound in the composition, be 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Carbonic Acid Ester (which may be Referred to as Compound D)>

A carbonic acid ester is a compound of the following formula (38).

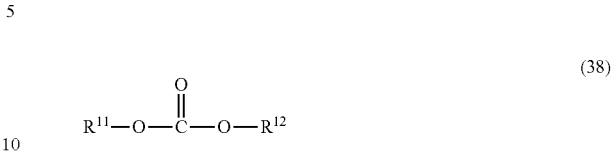

In the formula (38), $R^{11}$ and $R^{12}$ each independently represent an alkyl group, an aralkyl group, or an aryl group, preferably a C1-6 alkyl group or a C6-15 aryl group (more preferably a phenyl group).

Examples of the carbonic acid ester preferably available in the present invention include carbonic acid esters in which the $R^{11}$—O group and the $R^{12}$—O group in the formula (38) form alcohols or aromatic hydroxy compounds when hydrogen atoms are added to the groups. As the alcohol, an alcohol having one or two alcoholic hydroxy group (hydroxy group to be directly bonded to a carbon atom constituting the hydroxy compound other than an aromatic ring) exhibits generally a low viscosity, and thus is preferable, and a monoalcohol having one alcoholic hydroxy group is more preferable. From the viewpoint of easy availability, solubility of raw materials or resultant products, or the like, a C1-20 alkyl alcohol is preferable. As the aromatic hydroxy compound, from the viewpoint of industrial availability and generally low viscosity, monovalent to trivalent aromatic hydroxy compounds (that is, the number of hydroxy groups bonded to an aromatic ring is an integral number of 1 to 3) is preferable, and a monovalent aromatic hydroxy compound is more preferable. Substituent groups that substitute an aromatic hydrocarbon ring of the aromatic hydroxy compound are preferably groups selected from the group consisting of acyclic hydrocarbon groups and cyclic hydrocarbon groups (monocyclic hydrocarbon groups, condensed polycyclic hydrocarbon groups, cross-linked cyclic hydrocarbon groups, spiro hydrocarbon groups, ring-assembly hydrocarbon groups, and side chain-containing cyclic hydrocarbon group) or groups in which at least one group selected from the above-mentioned group are bonded (mutually-substituted groups) are preferable, in view of the difficulty in occurrence of side reactions.

Specifically, carbonic acid esters in which the $R^{11}$—O group and the $R^{12}$—O group in the formula (38) form hydroxy compounds, such as hydroxy compounds disclosed in paragraphs [0064] to [0081] of International Patent Application Publication No. WO 2014/069605 pamphlet, when hydrogen atoms are added to the groups, are preferably used as the compound D according to the present invention.

Specifically, a residual group obtained by removing a hydrogen atom bonded to an oxygen atom constituting the hydroxy compound indicated in the description regarding the <carbamate group-containing compound (which may be referred to as compound C)> from the hydroxy compound corresponds to the $R^{11}$—O group or the $R^{12}$—O group in the formula (38).

More preferably, dialkyl carbonates, such as dimethyl carbonate, diethyl carbonate, dipropyl carbonate (including isomers), or dibutyl carbonate (including isomers); aryl alkyl carbonates such as benzyl methyl carbonate or benzyl ethyl carbonate; alkyl aryl carbonates such as methyl phenyl carbonate, or ethyl phenyl carbonate; diaralkyl carbonates such as dibenzyl carbonate; or diaryl carbonates such as diphenyl carbonate, dicresyl carbonate or dicumyl carbonate can be mentioned, and even more preferably, dimethyl carbonate or diphenyl carbonate can be mentioned.

The amount of the carbonic acid ester, relative to the total mass of the isocyanate compound in the composition, is preferably 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Basic Amino Compound (which May be Referred to as Compound E)>

An amino compound is a derivative of ammonia, and examples thereof include: compounds (primary) in which one hydrogen atom is substituted with an alkyl group or an aryl group; compound (secondary) in which two hydrogen atoms are substituted therewith: and compounds (tertiary) in which all three hydrogen atoms are substituted therewith. The secondary or tertiary amino compounds are preferably available as the basic amino compound and an aliphatic amine, aromatic amine, heterocyclic amine, or basic amino acid is preferably available.

Examples thereof include: diethylamine, triethylamine, N,N'-diisopropyl ethylamine, tetramethylethylene diamine, aniline, ethylphenylamine, diethylphenylamine, 1,8-bis(dimethylamino)naphthalene, pyrrolidine, piperidine, piperazine, morpholine, 1,4-diazabicyclo[2,2,2]octane (DABCO), imidazole, pyridine, 4-dimethylamino pyridine, diazabicycloundecene (DBU), and 7-methyl-1,5,7-triazabicyclo[4,4,0]decene (MTBD) Among these, imidazole, diazabicycloundecene (DBU), or 1,4-diazabicyclo[2,2,2]octane (DABCO) is preferable.

The amount of the basic amino compound, relative to the total mass of the isocyanate compound in the composition, is preferably 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Halogen ion and/or Hydrolyzable Halogen Compound (which may be Referred to as Compound F)>

Examples of halogen ion include chlorine ion, bromine ion, and iodine ion. Examples of hydrolyzable halogen compound include: carbamoyl chloride compound in which a hydrochloric acid is added to an isocyanate group of an isocyanate compound and carbamoyl bromide compounds in which a hydrogen bromide is added to an isocyanate group. Preferable examples of isocyanate compound include isocyanate compounds having the structure (A) and/or the structure (B) according to the present embodiment.

The amount of the halogen ion and/or the hydrolyzable halogen compound, relative to the total mass of the isocyanate compound in the composition, is preferably 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Carbon Dioxide>

Carbon dioxide may be dissolved in isocyanate under an ordinary pressure or under pressure in a pressure vessel. The moisture amount contained in the carbon dioxide is controlled, as needed, because there is a case where the use of carbon dioxide containing moisture causes hydrolysis of an isocyanate compound.

The amount of carbon dioxide, relative to the total mass of the isocyanate compound in the composition, is preferably 1.0 ppm by mass to $1.0 \times 10^5$ ppm by mass (0.0001% by mass to 10% by mass), and, from the viewpoint of further coloring suppressibility, more preferably $1.0 \times 10^4$ ppm by mass or less, even more preferably $3.0 \times 10^3$ ppm by mass or less, and particularly preferably $1.0 \times 10^3$ ppm by mass or less.

<Metal Atom (which May be Referred to as Compound G)>

The isocyanate composition according to the present embodiment may contain a metal atom in addition to the above-mentioned compounds. The metal atom may be present as a metal ion, or as a metal atom alone. The metal atom may be one kind of metal atom or in combination of a plurality of kinds of metal atoms. Preferable examples of the metal atom include divalent to tetravalent metal atoms, and, among these, one kind or a plurality of kinds of metal selected from the group consisting of iron, cobalt, nickel, zinc, tin, copper, and titanium is more preferable. The amount of the compound relative to the total mass of the isocyanate compound in the composition, may be 0.002 ppm by mass to 10% by mass. Although the metal atom exhibits effects in suppression of coloring and denaturation when stored for a long time, there is a case where an excess amount of the metal atom promotes another reaction, and therefore the amount thereof is preferably 0.002 ppm by mass to 100 ppm by mass, more preferably 0.002 ppm by mass to 10 ppm by mass, and the most preferably 0.002 ppm by mass to 3 ppm by mass.

It is presumed that the metal atom coordinates with the structure (A) and/or the structure (B) to stabilize the structure, and thereby suppressing and inhibiting the initial reaction of coloring and suppressing the side reaction.

There is a case where a tiny amount of metal atom is contained in a raw material (amino acid), the vapor pressure of metal atom is extremely low, and thereby the metal atom is removed at a distillation (purification) step for preparing an isocyanate. On the other hand, even in the case where metal is gradually eluted from a material of a storage container when stored for a long time, the metal atom is not present in the above-mentioned amount in at least an initial stage of the storage for a long time, and thereby it is difficult to exhibit effects in coloring-suppressibility, denaturation-suppressibility, or the like.

The metal atom may be formulated as an organic acid salt such as acetate or naphthenate, chloride, or acetylacetone complex, or may be supplied from a composite metal in a reaction container by selecting conditions. In the case where the amount of the metal atom is larger than the above-mentioned range, the amount of the metal atom may be reduced to the above-mentioned range by conducting solvent-washing, distillation purification, crystallization, removal using an ion-exchange resin, removal using a chelate resin, or the like.

The amount of the metal component contained in the isocyanate composition may be determined by a conventionally-known method. For example, the determination method may be selected, in view of the sample form and the amount of contained metal component, from various methods such as atomic absorption spectrometry, inductively coupled plasma optical emission spectrometry, inductively coupled plasma mass spectrometry, x-ray fluorescence analysis, x-ray photoelectron spectroscopy, electron probe micro analyzer, or secondary ion mass spectrometry.

<Sulfuric Acid and/or Sulfuric Acid Ester>

The isocyanate composition according to the present embodiment may contain a sulfuric acid and/or a sulfuric acid ester. The term "sulfuric acid ester" refers to a compound formed by an ester bond of an alcohol and a sulfuric acid, and specific examples thereof include; benzenesulfonic acid, vinylsulfonic acid, methanesulfonic acid, p-toluenesulfonic acid, monomethylsulfuric acid, monoethylsulfuric acid, and mono n-propylsulfuric acid In addition, a sulfuric acid may be contained.

When the isocyanate composition further contains the sulfuric acid and/or sulfuric acid ester, the stability when the isocyanate composition is stored is further improved. It is presumed that the effect is exhibited due the presence of the sulfuric acid and/or sulfuric acid ester which moderately suppresses the formation of 1-nylon body structure, which results in suppression of the gelation of the whole of the isocyanate composition caused by the increase in the 1-nylon body structure. Accordingly, it is preferable that the sulfuric acid and/or sulfuric acid ester be contained in an appropriate amount so as to further improve the stability of the isocyanate composition, and the amount thereof, relative to the isocyanate compound, is preferably 1.0 ppm by mass to $1.0 \times 10^3$ ppm by mass. The lower limit of the amount is more preferably 3.0 ppm by mass or more, and even more preferably 5.0 ppm by mass or more. The upper limit of the amount is more preferably $1.0 \times 10^2$ ppm by mass or less, and even more preferably $5.0 \times 10^1$ ppm by mass or less.

<Phosphoric Acid and/or Phosphoric Acid Ester>

The isocyanate composition according to the present embodiment may contain a phosphoric acid and/or phosphoric acid ester. The term "phosphoric acid ester" refers to an ester formed by dehydration condensation of phosphoric acid and alcohol, and may be a phosphoric acid monoester, a phosphoric acid diester, or a phosphoric acid triester. Specific examples thereof include methyl phosphate, dimethyl phosphate, butyl phosphate, dibutyl phosphate, isodecyl phosphate, diisodecyl phosphate, 2-ethylhexyl phosphate, di-2-ethylhexyl phosphate, lauryl phosphate, dilauryl phosphate, stearyl phosphate, distearyl phosphate, dioleyl phosphate, and phenylphosphonic acid. In addition, a phosphoric acid may be contained.

When the isocyanate composition further contains the phosphoric acid and/or phosphoric acid ester, the stability when the isocyanate composition is stored is further improved. It is presumed that the effect is exhibited due the presence of the phosphoric acid and phosphoric acid ester which moderately suppresses the formation of 1-nylon body structure, which results in suppression of the gelation of the whole of the isocyanate composition caused by the increase in the 1-nylon body structure. Accordingly, it is preferable that the phosphoric acid and/or phosphoric acid ester be contained in an appropriate amount so as to further improve the stability of the isocyanate composition, and the amount thereof, relative to the isocyanate compound, is preferably 1.0 ppm by mass to $1.0 \times 10^3$ ppm by mass. The lower limit of the amount is more preferably 3.0 ppm by mass or more, and even more preferably 5.0 ppm by mass or more. The upper limit of the amount is more preferably $1.0 \times 10^2$ ppm by mass or less, and even more preferably $5.0 \times 10^1$ ppm by mass or less.

<Other Components>

Additional components other than the above-mentioned compounds may be contained within a range in which the coloring and the stability are not impaired. Preferable examples thereof include antioxidants, preferably selected from conventionally-known antioxidants such as phenol-based antioxidants, amine-based antioxidants, phosphorus-based antioxidants, sulfur-based antioxidants, hydrazine-based antioxidants, or amide-based antioxidants. The addition amount thereof, relative to the total amount of the isocyanate in the composition, may be 1 ppm by mass to 5000 ppm by mass.

<Isocyanate Composition According to the Present Embodiment>

First Embodiment

The isocyanate composition according to the present embodiment is an isocyanate composition containing an isocyanate compound of the following formula (1) and/or formula (2), and further contain: a compound of formula (3), which is different from the isocyanate compound, in an amount of 1.0 ppm by mass to 10% by mass, relative to the total mass of the isocyanate compound in the composition; a compound having an UV absorption in an area of decamer or higher isocyanates in a measurement spectrum of gel permeation chromatography in an amount of 1.0 ppm by mass to 10% by mass, relative to the total mass of the isocyanate compound in the composition; and/or, a compound containing an isocyanurate group and/or a biuret group.

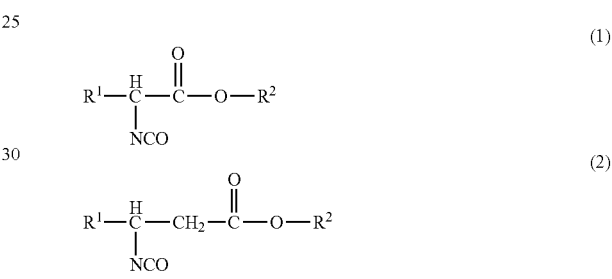

In the formulae, $R^1$ represents a hydrogen atom or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may represent —C(═O)OR² or —CH₂—C(═O)O—R².

In the formula, $R^{13}$ represents an organic group with a valence of a, $R^{14}$ represents a monovalent organic group, and a represents an integer of 1 or 2.

The compound of the formula (3), the compound having an UV absorption in an area of decamer or higher isocyanates in a measurement spectrum of gel permeation chromatography, and the compound containing an isocyanurate group and/or a biuret group may be formulated alone, or in combination of a plurality of kinds thereof.

An unsaturated bond-having compound as a contaminant tends to cause coloring, because an unsaturated bond of the unsaturated bond-having compound generally tends to be easily oxidized. However, the compound of the formula (3) acts effectively on the isocyanate composition, when stored, to improve the stability of the isocyanate compound without coloring the isocyanate composition. It is presumed that the effect is exhibited by suppressing the denaturation reaction of the isocyanate compound caused by water or oxygen due to the reactivity of an ester group of the compound of the formula (3) against water or oxygen. In addition, the compound of the formula (3) tends to exhibit the effect easily due to the unsaturated bond between carbon and oxygen.

Although the amount of the compound of the formula (3) is preferably increased so as to suppress the denaturation reaction of the isocyanate compound, an excess amount thereof may cause coloring due to unsaturated bonds as mentioned above, which may result in deterioration of appearance when used. Accordingly, the amount of the unsaturated bond-having compound, relative to the total mass of the isocyanate compound, is 1.0 ppm by mass to $1.0 \times 10^5$ ppm by mass, the lower limit thereof is preferably 3.0 ppm by mass or more, more preferably 5.0 ppm by mass or more, and even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less.

The compound having an UV absorption in an area of decamer or higher isocyanates in a measurement spectrum of gel permeation chromatography also exhibits the same effect as that of the compound of the formula (3). It is presumed that the compound exhibits the effect due to the presence of 1-nylon skeleton having a high reactivity against water, oxygen, or the like.

The compound having an isocyanurate group and/or a biuret group also exhibits the same effect. Although the amount of the compound in the isocyanate composition is preferably increased so as to suppress the denaturation reaction of the isocyanate compound, it is preferable that the amount is not excessively increased in view of the coloring-suppressibility or appearance when used. Thus, the amount of the unsaturated bond-having compound according to the present embodiment, relative to the total mass of the isocyanate compound, is 1.0 ppm by mass to $1.0 \times 10^5$ ppm by mass, the lower limit thereof is preferably 3.0 ppm by mass or more, more preferably 5.0 ppm by mass or more, and even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less.

In the case where a plurality of kinds of compound of the formula (3), the compound having an UV absorption in an area of decamer or higher isocyanates in a measurement spectrum of gel permeation chromatography, and/or, the compound containing an isocyanurate group and/or a biuret group is used, the total amount thereof, relative to the total mass of the isocyanate compound, is 1.0 ppm by mass to $1.0 \times 10^5$ ppm by mass, the lower limit thereof is preferably 3.0 ppm by mass or more, more preferably 5.0 ppm by mass or more, and even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less.

In addition to the above-mentioned compounds, the isocyanate composition according to the present embodiment may further contain 1.0 ppm by mass to $1.0 \times 10^5$ ppm by mass, relative to the isocyanate compound, of saturated and/or unsaturated hydrocarbon compounds having a linear-chain, branched-chain, or cyclic structure, and/or, ether compounds and/or thioether compounds. The saturated and/or unsaturated hydrocarbon compounds having a linear-chain, branched-chain, or cyclic structure are preferable from the viewpoint of thermal stability without generating oxidized materials or peroxidized material. The saturated and/or unsaturated hydrocarbon compounds having a linear-chain, branched-chain, or cyclic structure, ether compounds, and/or thioether compounds may be used alone, or in combination of a plurality of kinds thereof.

Although the saturated and/or unsaturated hydrocarbon compounds having a linear-chain, branched-chain, or cyclic structure, an ether compounds and/or a thioether compounds generally do not have reactivity with water, oxygen, or the like, the stability of isocyanate is further improved due to the presence of the saturated and/or unsaturated hydrocarbon compounds having a linear-chain, branched-chain, or cyclic structure, the ether compounds and/or the thioether compounds. More specifically, it is presumed that the saturated and/or unsaturated hydrocarbon compounds having a linear-chain, branched-chain, or cyclic structure, the ether compounds and/or the thioether compounds, infinitesimally coexistent, are partially vaporized in a storage container to exist in a vapor phase in a storage container, and thereby contributing to the suppression of increase in the viscosity of the isocyanate composition or generation of gel components caused by action of infinitesimally coexistent water or oxygen, and thus further favorable effects are exhibited in combination with the compound of formula (3).

Although the amount of the saturated and/or unsaturated hydrocarbon compounds having a linear-chain, branched-chain, or cyclic structure, the ether compounds and/or the thioether compounds is preferably increased in view of the above-mentioned circumstances, there is a case where an excess amount thereof significantly changes properties originally expected to be provided to the isocyanate composition, such as viscosity. Thus, the amount of the saturated and/or unsaturated hydrocarbon compounds having a linear-chain, branched-chain, or cyclic structure, the ether compounds, and/or the thioether compounds, relative to the total mass of the isocyanate compound in the isocyanate composition, is 1.0 ppm by mass to $1.0 \times 10^5$ ppm by mass, the lower limit thereof is preferably 3.0 ppm by mass or more, more preferably 5.0 ppm by mass or more, and even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less.

In the case where a plurality of kinds of the saturated and/or unsaturated hydrocarbon compounds having a linear-chain, branched-chain, or cyclic structure, the ether compounds, and/or the thioether compounds are used, the total amount thereof is preferably 1.0 ppm by mass to $1.0 \times 10^5$ ppm by mass, the lower limit thereof is preferably 3.0 ppm by mass or more, more preferably 5.0 ppm by mass or more, and even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less.

The isocyanate composition according to the present embodiment may further contain 1.0 ppm by mass to 10% by mass, relative to the total mass of the isocyanate compound, of a carbamate group-containing compound and/or a carbonic acid ester. The carbamate group-containing compound and/or the carbonic acid ester are preferable from the viewpoint of thermal stability.

In the isocyanate composition according to the present embodiment, the carbamate group-containing compound and the carbonic acid ester compound exhibit effects of improving the stability of the isocyanate compound without coloring the isocyanate composition when the isocyanate composition is stored. It is presumed that the effect is exhibited by suppressing the denaturation reaction of the isocyanate compound caused by water or oxygen due to the reactivity of an ester portion of the carbamate group-containing compound or the carbonic acid ester compound against water or oxygen.

In the case where a plurality of kinds of carbamate group-containing compounds and/or the carbonic acid esters are used, the total amount thereof is preferably 1.0 ppm by mass to 10% by mass, relative to the total mass of the isocyanate compound.

In addition, the isocyanate composition according to the present embodiment may further contain a basic amino compound, a halogen ion, and/or a hydrolyzable halogen compound in an amount of 1.0 ppm by mass to 10% by mass, relative to the total mass of the isocyanate compound.

The presence of the basic amino compound, the halogen ion, and/or the hydrolyzable halogen compound improves the stability when the isocyanate composition is stored. It is presumed that the effect is exhibited by trapping oxygen or water by the halogen atom or the basic amino group, the oxygen and water deteriorating the stability of the isocyanate compound.

The isocyanate composition according to the present embodiment may contain a metal atom (compound G).

In addition, the isocyanate composition according to the present embodiment may contain a sulfuric acid and/or a sulfuric acid ester.

The stability when the isocyanate composition is stored is further improved by further containing the sulfuric acid and/or the sulfuric acid ester. It is presumed that the effect is exhibited by moderately suppressing the formation of 1-nylon body structure due to the presence of the sulfuric acid and/or the sulfuric acid ester, and thereby suppressing gelation of the whole isocyanate composition caused by increase in the 1-nylon body structure. Thus, it is preferable that the sulfuric acid and/or the sulfuric acid ester be contained in an appropriate amount, and preferably contained, for example, in an amount of 1.0 ppm by mass to $1.0 \times 10^3$ ppm by mass, relative to the isocyanate compound, so as to further improve the stability of the isocyanate composition. The lower limit of the amount thereof is preferably 3.0 ppm by mass or more, and more preferably 5.0 ppm by mass or more, and the upper limit thereof is preferably $1.0 \times 10^2$ ppm by mass or less and more preferably $5.0 \times 10^1$ ppm by mass or less.

In addition, the isocyanate composition according to the present embodiment may contain a phosphoric acid and/or a phosphoric acid ester.

The stability of the isocyanate composition when stored is further improved by further containing the phosphoric acid and/or the phosphoric acid ester. It is presumed that the effect is exhibited by moderately suppressing the formation of 1-nylon body structure due to the presence of the phosphoric acid or the phosphoric acid ester, and thereby suppressing the gelation of the whole isocyanate composition caused by the increase in the 1-nylon body structure. Thus, it is preferable the phosphoric acid and/or the phosphoric acid ester be contained in an appropriate amount so as to further improve the stability of the isocyanate composition, and, for example, in an amount of 1.0 ppm by mass to $1.0 \times 10^3$ ppm by mass, relative to the isocyanate compound. The lower limit of the amount is preferably 3.0 ppm by mass or more, and more preferably 5.0 ppm by mass or more, and the upper limit thereof is preferably $1.0 \times 10^2$ ppm by mass or less, and more preferably $5.0 \times 10^1$ ppm by mass or less.

In the case where a plurality of kinds of sulfuric acid, sulfuric acid ester, phosphoric acid, and/or phosphoric acid ester is used, the total amount thereof in combination, relative to the isocyanate compound, is preferably 1.0 ppm by mass to $1.0 \times 10^3$ ppm by mass. The lower limit of the amount is 3.0 ppm by mass or more, and more preferably 5.0 ppm by mass or more, and the upper limit thereof is $1.0 \times 10^2$ ppm by mass or less, and more preferably $5.0 \times 10^1$ ppm by mass or less.

Second Embodiment

Although an isocyanate composition according to the second embodiment will be explained below, a detailed description of the same components as those of the first embodiment may be omitted.

The isocyanate composition according to the present embodiment contains: an isocyanate compound of the following formula (1) and/or formula (2); and a specific stabilizer, which is different from the isocyanate compound, in an amount of 0.002 ppm by mass to 10% by mass, relative to the total mass of the isocyanate compound in the isocyanate composition.

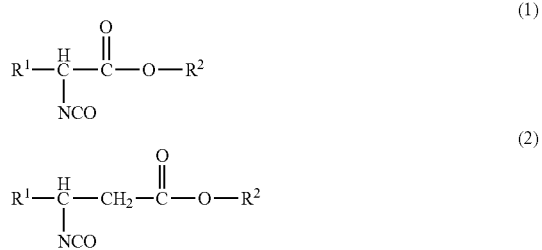

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may represent a group represented by —C(=O)OR² or —CH₂—C(=O)O—R².

The specific stabilizer is at least one compound selected from the group consisting of the following compound A to compound G and carbon dioxide.

Compound A: saturated and/or unsaturated hydrocarbon compounds having a linear-chain, branched-chain, or cyclic structure.

Compound B: compounds having at least one bond selected from the group consisting of an ether bond and a thioether bond.

Compound C: carbamate group-containing compounds

Compound D: carbonic acid esters

Compound E: basic amino compounds

Compound F: halogen ion, and/or hydrolyzable halogen compound

Compound G: metal atom

The stability of the isocyanate composition according to the present embodiment when stored is improved by the presence of the stabilizer.

Although the compounds A and B do not have reactivity against water, oxygen, or the like, the stability of the isocyanate compound of the isocyanate composition according to the present embodiment is improved by the presence of the compounds A and B. It is presumed that the effect is exhibited by partially vaporizing the compounds A and B, infinitesimally coexistent, in a storage container to make the compounds A and B exist as a vapor phase component in the vapor phase in the storage container to suppress the increase in the viscosity or generation of gel components, which are undesirably caused by the action of water or oxygen, infinitesimally exist in a storage container of the isocyanate composition.

Although the amount of the compounds A and B is preferably increased in view of the above-mentioned circumstances, there is a case where an excess amount thereof significantly changes properties originally expected to be provided to the isocyanate composition, such as viscosity. Thus, the amount of the compounds A and B according to the present embodiment is 1.0 ppm by mass to $1.0 \times 10^5$ ppm by mass, the lower limit thereof is preferably 3.0 ppm by mass or more, more preferably 5.0 ppm by mass or more, and even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less. The compounds A and B may be used alone or in combination of a plurality of kinds thereof.

Although an unsaturated bond-having compound as a contaminant tends to cause coloring, because an unsaturated bond generally tends to be oxidized, the compounds C and D exhibits effects of improving the stability of the isocyanate compound without coloring the isocyanate composition when the isocyanate composition is stored. It is presumed that the effect is exhibited by suppressing the denaturation reaction of the isocyanate compound caused by water or oxygen due to the reactivity of ester portions of the compounds C and D against water or oxygen.

Although the amount of the compounds C and D is preferably increased in view of the above-mentioned circumstances, there is a case where an excess amount thereof deteriorates the stability of the isocyanate composition. Thus, the amount of the compounds C and D according to the present embodiment is 1.0 ppm by mass to $1.0 \times 10^5$ ppm by mass, the lower limit thereof is preferably 3.0 ppm by mass or more, more preferably 5.0 ppm by mass or more, even more preferably 10 ppm by mass or more, and the upper limit thereof is preferably $1.0 \times 10^4$ ppm by mass or less, more preferably $3.0 \times 10^3$ ppm by mass or less, and even more preferably $1.0 \times 10^3$ ppm by mass or less. The compounds C and D may be used alone or in combination of a plurality of kinds thereof.

The stability of the isocyanate composition when stored is also improved by the presence of the compounds E and F. It is presumed that the effect is exhibited by trapping oxygen or water by a halogen atom or a basic amino group, the oxygen and the water causing deterioration of the stability of the isocyanate compound.

Although the amount of the compounds E and F is preferably increased in view of the above-mentioned circumstances, there is a case where an excess amount of the compounds E and F deteriorates the stability of the isocyanate composition. Thus, the amount of the compounds E and F in the present embodiment is 1.0 ppm by mass to $1.0 \times 10^5$ ppm by mass, the lower limit of the amount is preferably 3.0 ppm by mass or more, more preferably 5.0 ppm by mass or more, and even more preferably 10 ppm by mass or more, and the upper limit of the amount is preferably $1.0 \times 10^4$ ppm by mass or less, more preferably $3.0 \times 10^3$ ppm by mass or less, and even more preferably $1.0 \times 10^3$ ppm by mass or less. The compounds E and F may be used alone or in combination of a plurality of kinds thereof.

It is preferable that the isocyanate composition according to the present embodiment be stable at 25° C. under atmospheric pressure for at least 30 days, at least 60 days, at least 90 days, at least 120 days, at least 150 days, 150 days to 300 days, or 300 days to 600 days. More specifically, it is preferable that the hue (Hazen color) of the isocyanate composition after stored for a period, such as a long-term period, be 120 APHA or less, preferably 60 APHA or less, more preferably 30 APHA or less, and even more preferably 25 APHA or less. It is preferable that filtration residue components obtained by filtrating the isocyanate composition through a filter having a pore size of 1 µm (such as viscous gelatinous material or solid content) be suppressed. Although the material of the filter may be appropriately selected, the filter is preferably made of PTFE. The amount of the filtration residue components is determined from filter weight values before and after filtration as the denaturation amount (indicated by "% by mass", relative to 100 g of a liquid to be filtrated). The denaturation amount is 10% by mass or less, preferably 2% by mass or less, and more preferably 1% by mass or less, in view of the uniformity when used as a coating raw material.

The isocyanate composition according to the present embodiment may contain 1.0 ppm by mass to $1.0 \times 10^3$ ppm by mass, relative to the isocyanate compound, of a sulfuric acid, a sulfuric acid ester, a phosphoric acid, and/or a phosphoric acid ester, in a similar manner to that of the isocyanate composition according to the first embodiment.

Third Embodiment

Although an isocyanate composition according to the third embodiment will be explained below, a detailed description of the same components as those of the first or second embodiment may be omitted.

The isocyanate composition according to the present embodiment contains: an isocyanate compound of the following formula (1) and/or formula (2); and 1.0 ppm by mass to $1.0 \times 10^3$ ppm by mass of a phosphoric acid and/or a phosphoric acid ester, and/or, 1.0 ppm by mass to $1.0 \times 10^3$ ppm by mass of a sulfuric acid and/or a sulfuric acid ester, relative to the total mass of the isocyanate compound in the isocyanate composition.

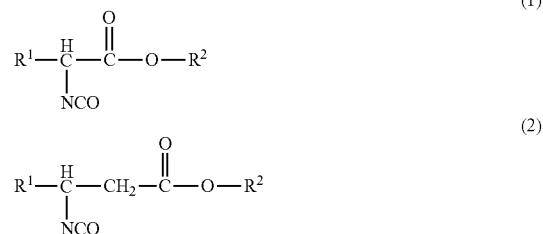

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group R2 from the compound of the formula (1) or the formula (2), or a residual group obtained by removing the group $R^1$ or the group $R^2$ from the compound of the formula (1) or the formula (2). In addition, $R^1$ may represent a group represented by $-C(=O)OR^2$ or $-CH_2-C(=O)O-R^2$.

Fourth Embodiment

Although an isocyanate composition according to the fourth embodiment will be explained below, a detailed description of the same components as those of the first, second, or third embodiment may be omitted.

The isocyanate composition according to the present embodiment contains, as isocyanate compounds, a trifunctional isocyanate compound of the following formula (1) and/or (2), having three isocyanate groups in a molecule thereof, and a difunctional isocyanate compound of the following formula (1) and/or (2), having two isocyanate groups in a molecule thereof.

In a more preferable embodiment, both the trifunctional isocyanate compound and the difunctional isocyanate compound are represented by the following formula (1). Alternatively or, both the trifunctional isocyanate compound and the difunctional isocyanate compound are represented by the following formula (2). Alternatively or, the difunctional isocyanate compound is represented by the formula (1), and the trifunctional isocyanate compound is represented by the formula (2).

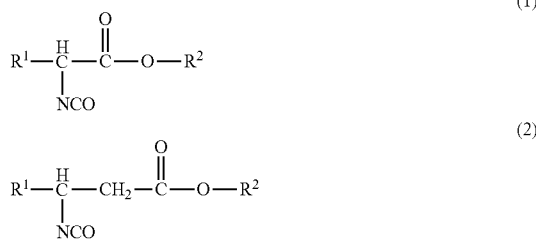

In the formulae, $R^1$ represents a hydrogen or a monovalent organic group, and $R^2$ represents a monovalent organic group. $R^1$ and $R^2$ may each independently represent a residual group obtained by removing one hydrogen atom of the group $R^1$ or the group $R^2$ from the compound of the formula (1) or the formula (2), or a residual group obtained by removing the group $R^1$ or the group $R^2$ from the compound of the formula (1) or the formula (2). In addition, $R^1$ may represent a group represented by $—C(=O)OR^2$ or $—CH_2—C(=O)O—R^2$. Isocyanate groups are present in at least one of $R^1$ and $R^2$, and the number of isocyanate groups present in $R^1$ and $R^2$ is 2 or 3.

The isocyanate composition according to the present embodiment may contain 1.0 ppm by mass to $1.0 \times 10^3$ ppm by mass, relative to the isocyanate compound, of a sulfuric acid, a sulfuric acid ester, a phosphoric acid, and/or a phosphoric acid ester, in a similar manner to that of the isocyanate composition according to the first, second, or third embodiment.

In addition, the isocyanate composition according to the present embodiment may contain: a compound having an UV absorption in an area of decamer or higher isocyanates in a measurement spectrum of gel permeation chromatography in an amount of 1.0 ppm by mass to 10% by mass, relative to the total mass of the isocyanate compound in the composition; and/or the compound having an isocyanurate group and/or a biuret group in an amount of 1.0 ppm by mass to 10% by mass, relative to the total mass of the isocyanate compound in the composition, in a similar manner to that of the isocyanate composition according to the first, second, or third embodiment.

In addition, the isocyanate composition according to the present embodiment may contain: the saturated and/or unsaturated hydrocarbon compounds having a linear-chain, branched-chain, or cyclic structure in an amount of 1.0 ppm by mass to 10% by mass, relative to the total mass of the isocyanate compound in the composition; and/or, the compound having at least one bond selected from the group consisting of an ether bond and a thioether bond, in an amount of 1.0 ppm by mass to 10% by mass, relative to the total mass of the isocyanate compound in the composition, in a similar manner to that of the isocyanate composition according to the first, second, or third embodiment.

In addition, the isocyanate composition according to the present embodiment may contain a carbamate group-containing compound and/or a carbonic acid ester in an amount of 1.0 ppm by mass to 10% by mass, relative to the total mass of the isocyanate compound in the composition, in a similar manner to that of the isocyanate composition according to the first, second, or third embodiment.

In addition, the isocyanate composition according to the present embodiment may contain 1.0 ppm by mass to 10% by mass, relative to the total mass of the isocyanate compound, of the basic amino compound, the halogen ion, and/or, the hydrolyzable halogen compound, in a similar manner to that of the isocyanate composition according to the first, second, or third embodiment.

<Method for Producing an Isocyanate Compound having the Structure (A) and/or the Structure (B)>

As a method for producing an isocyanate compound having the structure (A) and/or the structure (B) according to the present embodiment, a conventionally-known method for producing an isocyanate may be used. Examples of the method for producing an isocyanate compound include a phosgene method, as disclosed in Patent Documents 1-5, in which a corresponding amino group-containing compound or a salt of an inorganic acid (such as hydrochloric acid or sulfuric acid) of the amino group-containing compound with phosgene.

<Method for Producing an Isocyanate Composition According to the First Embodiment>

The isocyanate composition according to the first embodiment is produced by appropriately mixing the isocyanate compound produced by the above-mentioned method with the compound of the formula (3) and/or the compound having an UV absorption in an area of decamer or higher isocyanates in a measurement spectrum of gel permeation chromatography. The isocyanate composition is preferably produced at 0° C. to 40° C. The isocyanate composition is produced under an atmosphere of an inert gas such as nitrogen, argon, or neon.

A method for producing a compound having an UV absorption at an area of decamer of isocyanate in a measurement spectrum of gel permeation chromatography will be explained below.

As mentioned above, the compound preferably has a 1-nylon structure, and is produced, for example, by reacting an isocyanate compound having at least one isocyanate group in a molecule thereof in the presence of a catalyst, followed by adding a terminating agent thereto to stop the polymerization reaction. As the catalyst, the same catalyst as that used in the isocyanurate-forming reaction described below may be used. Although the amount of the catalyst to be used depends on the kind of the used compound, the amount may be $1.0 \times 10^{-4}$ parts by mass to 1.0 part by mass, relative to 100 parts by mass of the isocyanate compound. The upper limit of the amount of the catalyst to be used is preferably $5.0 \times 10^{-1}$ parts by mass or less, more preferably $1.0 \times 10^{-1}$ parts by mass or less, and even more preferably $2.0 \times 10^{-2}$ parts by mass or less, from the viewpoint of the suppressibility of coloration or discoloration of the resultant products and reaction control. The lower limit of the amount of the catalyst to be used is preferably $1.0 \times 10^{-3}$ parts by mass or more, and more preferably $2.0 \times 10^{-3}$ parts by mass or more, from the viewpoint of reactivity.

As the terminating agent, the same terminating agent as that used in the isocyanurate-forming reaction described below may be used. Although the amount of the terminating agent to be used may be appropriately selected depending on the amount of the used catalyst or the kind of the used compound, the amount is preferably at least 1 equivalent, relative to the amount of the used catalyst.

The temperature at which the polymerization reaction of the isocyanate compound is conducted in the presence of a catalyst is preferably −20° C. to 60° C. There is a tendency that the isocyanurate-forming reaction easily proceeds in association with the increase in the reaction temperature, and therefore the reaction temperature is preferably low so as to obtain a 1-nylon body structure. On the other hand, the polymerization reaction of the isocyanate compound proceeds excessively slowly at an excessively low reaction temperature, and therefore the reaction temperature is more preferably −10° C. to 50° C., and even more preferably 0° C. to 40° C.

The polymerization of the isocyanate compound is conducted in the presence or absence of a solvent, the polymerization is preferably conducted in the presence of a solvent from the viewpoint of easiness in reaction control and operation. As the solvent, a solvent which is inert to the isocyanate compound to be used, and can dissolve both a raw isocyanate compound and a resultant polymer. Specifically, as the solvent, acetate esters, such as ethyl acetate, butyl acetate, or amyl acetate; aromatic hydrocarbons such as benzene, toluene, xylene, or monochlorobenzene, or the like may be used alone or in combination.

The progress of polymerization may be tracked by appropriately sampling the reaction liquid and then conducting gel permeation chromatography measurement, and the reaction may be stopped by adding a terminating agent to the reaction liquid when a peak is confirmed at an area of desired molecular weight. In the case where the isocyanurate-forming reaction is conducted in the absence of the solvent, an unreacted isocyanate compound serves as a solvent by making the conversion rate be 50% or less to dissolve the resultant polymer therein.

The thus produced compound having an UV absorption at an area of decamer of isocyanate in a measurement spectrum of gel permeation chromatography may be collected by removing the unreacted isocyanate compound and the solvent from the reaction system after the end of the reaction, or a reaction liquid may be used directly to produce an isocyanate composition according to the present embodiment. In the case where the isocyanurate compound is collected, the collection method is not particularly limited, and examples thereof include a method in which an unreacted polyisocyanate and a solvent is removed by conducting distillation purification. The removal of the solvent is preferably conducted at a low temperature, and using, for example, an apparatus which has a large evaporation area for liquid and exhibits a favorable evaporation efficiency, such as falling thin-film evaporator, thin-film evaporation apparatus, or molecular distillation apparatus.

Regarding the compound containing an isocyanurate group and/or a biuret group, a compound containing an isocyanurate group may be produced by the same method as described in <method for producing an isocyanate polymer by reacting an isocyanate compound having the structure (A) and/or the structure (B)> described below.

The compound having a biuret group may be produced by allowing the reaction to proceed using, for example, water, monovalent tertiary alcohol, formic acid, hydrogen sulfide, organic primary monoamine, organic primary diamine, as a biuret-forming agent, at a reaction temperature of 70° C. to 200° C., for 10 minutes to 24 hours, followed by, after the end of the reaction, separating unreacted polyisocyanates and a solvent from a composition containing an isocyanate polymer by conducting treatment such as a thin film distillation method or a solvent extraction method. The same solvent as that of the <method for producing an isocyanate polymer by reacting an isocyanate compound having the structure (A) and/or the structure (B)> described below may be used in the biuret reaction.

<Method for Producing an Isocyanate Composition According to the Second Embodiment>

The isocyanate composition according to the second embodiment is produced, for example, by appropriately mixing the isocyanate compound produced by the above-mentioned method with the compounds A to G The isocyanate composition is produced preferably at 0° C. to 40° C. The isocyanate composition is produced under an atmosphere of an inert gas such as nitrogen, argon, or neon.

<Method for Producing an Isocyanate Composition According to the Third Embodiment>

The isocyanate composition according to the third embodiment is produced, for example, by appropriately mixing the isocyanate compound produced by the above-mentioned method with a phosphoric acid, a phosphoric acid ester, a sulfuric acid, and/or a sulfuric acid ester. The isocyanate composition is produced preferably at 0° C. to 40° C. The isocyanate composition is produced under an atmosphere of an inert gas such as nitrogen, argon, or neon.

<Method for Producing an Isocyanate Composition According to the Fourth Embodiment>

The isocyanate composition according to the fourth embodiment is produced, for example, by appropriately mixing the trifunctional isocyanate compound and the difunctional isocyanate compound, produced by the above-mentioned method. The isocyanate composition is produced preferably at 0° C. to 40° C. The isocyanate composition is produced under an atmosphere of an inert gas such as nitrogen, argon, or neon.

<Method for Purifying an Isocyanate Compound having the Structure (A) and/or the Structure (B)>

Purification may be conducted, as needed, so as to prevent coloration at an initial stage of production, because the aim of the present embodiment is to realize coloring-suppressibility in a long time storage and improvement in the stability in a long time storage.

The purification may be conducted by a conventionally-known method such as distillation, adsorption, or extraction. The purification is preferably conducted by a conventionally-known LTI decolorization and purification method. It is preferable according to the present invention that a crude isocyanate compound be purified by distillation, and the isocyanate compound is retrieved as a vapor phase component to conduct purification. At this time, it is preferable that replacement with an inert gas be conducted, and more preferably distillation be conducted while conducting supply of an inert gas. Preferable examples of inert gas include nitrogen, argon, helium, and low-boiling organic compounds free from active hydrogens that serve as vapor phase components at a distillation temperature and pressure. Preferable examples of the low-boiling organic compound include hydrocarbon compounds and ether compounds constituted by hydrocarbon groups, the boiling point of which is 100° C. or less, preferably 80° C. or less at 25° C. under an atmospheric pressure.

As a purification method, a purification method containing a distillation purification step is preferable from the viewpoint of preventability of contamination of unintentional low-boiling impurities and coloration at an initial stage. There is a possibility that purification methods such as crystallization or adsorption removal does not achieve the object.

<Purification Method (1) Distillation Purification>

Materials of an apparatus and lines in which distillation separation of the isocyanate compound is conducted may be conventionally-known materials, unless starting materials or reaction materials are adversely affected. As the material, for example, glass, glass lining, SUS 304, SUS 316, SUS 316L, or the like, is inexpensive and preferably used.

The type of a distillation apparatus is not particularly limited, and a conventionally-known distillation apparatus may be used. As the distillation apparatus, for example, various known distillation apparatuses, such as distillation apparatuses including any of multi-stage distillation column, continuous multi-stage distillation column, packed column, thin film distillation apparatus, and falling film distillation apparatus, or distillation apparatuses combining them may be used.

The term "multistage distillation column" refers to a distillation column having multiple plates in which the number of theoretical plates in distillation is three or more. As the multistage distillation column, for example, one that can perform continuous distillation may be appropriately used. In addition, in the case where the number of theoretical plates is excessively large, the multistage distillation column becomes huge and industrial practice may be difficult, and therefore, the number of theoretical plates is preferably 500 or less.

As the multistage distillation column, for example, any one that is generally used as a multi-stage distillation column, such as a plate column system using trays such as bubble cap trays, porous plate trays, valve trays, or countercurrent trays, or a packed column system filled with various types of packing materials such as Raschig ring, Lessing ring, Pall ring, Berl saddle, Intalox saddle, Dixon packing, McMahon packing, HELI PACK, Sulzer packing or Mellapak, may be used. Furthermore, one having a plate-packed mixed column system including both of plate parts and parts filled with packing materials is also preferably used.

Although the pressure at which the distillation separation is performed may be appropriately varied depending on a composition of the isocyanate composition to be supplied to the distillation apparatus in which the distillation separation is performed, a temperature, a type of the distillation apparatus, or the like, and the distillation separation is performed under reduced pressure, under atmospheric pressure, or under increased pressure, the distillation separation is preferably performed under reduced pressure to reduce the contact time at a high temperature, because the isocyanate having the structure according to the present invention has a high boiling point and there is a case where the isocyanate causes the thermal denaturation. The distillation separation is generally performed at a pressure of within a range of 0.1 Pa to 100 KPa (absolute pressure), and, considering easiness of industrial practice, more preferably within a range of 0.1 Pa to 50 kPa (absolute pressure), and more preferably within a range of 0.5 Pa to 50 kPa (absolute pressure). In addition, the interior of the distillation apparatus is preferably replaced with an inert gas before distillation, and distillation is more preferably performed while supplying the inert gas thereto.

The temperature at which the distillation separation is performed may be appropriately varied depending on a composition of the isocyanate composition to be supplied to the distillation apparatus in which the distillation separation is performed, a temperature, a type of the distillation apparatus, or the like, but there is a case where the isocyanate compound is thermally denaturated when the temperature is excessively high, whereas industrial practice is not easy because of requiring new equipment configured to conduct cooling or the like when the temperature is excessively low, and thus, the distillation separation is performed preferably at a temperature of within a range of 50° C. to 350° C., more preferably within a range of 80° C. to 300° C., and even more preferably within a range of 100° C. to 250° C.

In the method according to the present embodiment, at least one compound selected from the group consisting of compounds A to G and carbon dioxide may be formulated in the isocyanate composition liquid before or after the distillation purification step or during the distillation step.

<Purification Method (2) Method in which a Solvent that does not Exhibit Compatibility and has a High Boiling Point is Added and then Purification is Conducted Using a Thin Film Distillation Apparatus>

According to the present embodiment, a solvent does not exhibit compatibility with an isocyanate compound having the structure (A) and/or the structure (B) (which causes two-phase separation at normal temperature) and a boiling point, and the temperature and the pressured are set in a similar way to that of the purification method (1), in accordance with Japanese Unexamined Patent Application Publication No. Sho 60-54349. In addition, the interior of the distillation apparatus is preferably replaced with an inert gas before distillation, and distillation is more preferably performed while supplying the inert gas thereto.

In the method according to the present embodiment, the metal atom may be formulated in the isocyanate composition liquid before or after the distillation purification step or during the distillation step. In addition, at least one compound selected from the group consisting of compounds A to G and carbon dioxide may be formulated in the isocyanate composition liquid before or after the distillation purification step or during the distillation step.

<Purification Method (3) Adsorption and Distillation>

The method may be conducted in accordance with the method disclosed in Japanese Unexamined Patent Application Publication No. 2002-3462 or International Patent Application Publication No. WO 2004-022527, in which distillation is conducted after bringing into contact with an activated carbon or a metallic halide.

Specifically, a mixture containing an isocyanate compound is brought into contact with an activated carbon or a metallic halide. The activated carbon or the metallic halide may be added before removing the solvent from the resultant reaction liquid. The method for bringing into contact therewith is preferably conducted in a batch-wise manner, or using a packed column or the like. As the activated carbon, any activated carbon may be used unless water is contained, and a commercially-available product is generally used. Examples of the commercially-available product include purified SHIRASAGI and SHIRASAGI P, manufactured by Takeda Pharmaceutical Company Limited, and TAIKO SA 1000 manufactured by FUTAMURA CHEMICAL CO., LTD.

The metallic halide may be a metallic halide having a high purity or an industrial grade metallic halide, and a commercially-available product is generally available. Preferable examples of a metal of the metallic halide include copper, zinc, aluminum, tin, and lead, and examples of a halogen thereof include fluorine, chlorine, bromine, and iodine. Preferable examples of the metallic halide include metallic chlorides such as zinc chloride, aluminum chloride, and tin chloride, and, among these, zinc chloride is more preferably used.

The activated carbon and the metallic halide may be used together, and the combinational use thereof is more effective. The used amount of the activated carbon or the metallic halide, relative to the lysine ester triisocyanate, is preferably 1.0% by mass to 10% by mass, and more preferably 0.5% by mass to 7% by mass. In the case where the activated carbon and the metallic halide are used together, the used amounts thereof are preferably 0.1% by mass to 0.8% by mass, and more preferably 0.3% by mass to 0.6% by mass, respectively.

A solvent may be used when the mixture containing an isocyanate and the activated carbon are contacted, and examples of the solvent include: aromatic-based solvents such as toluene and xylene; ketone-based solvents such as acetone, methyl ethyl ketone, methyl isobutyl ketone, and cyclohexanone; ester-based solvents such as ethyl acetate, butyl acetate, and isobutyl acetate; glycol ether ester-based solvents such as ethylene glycol ethyl ether acetate, propylene glycol methyl ether acetate, 3-methyl-3-methoxy butyl acetate, and ethyl-3-ethoxy propionate; and ether-based solvents such as tetrahydrofuran and dioxane. The used amount of the solvent, relative to the mixture containing the isocyanate, is preferably 0.1 to 20 times (weight ratio), and more preferably 0.1 to 10 times (weight ratio).

The temperature at which the mixture is contacted with the activated carbon or the metallic halide is preferably 10° C. to 150° C., more preferably 10° C. to 140° C., and even more preferably 10° C. to 40° C. The contact is generally conducted under nitrogen atmosphere for 30 minutes to 3 hours. Although the contact may be conducted at normal pressure, the contact may also be conducted under increased pressure of reduced pressure.

Although the mixture containing the isocyanate obtained by the contact is further subjected to distillation, the activated carbon or the metallic halide is preferably removed by filtration before distillation. Although the distillation may be conducted by a conventional procedure, the distillation is preferably conducted by thin film distillation using a molecular distillation device. In the case where the thin film distillation is conducted, decompression treatment may be conducted before thin film distillation, as needed. The interior of the distillation apparatus is preferably replaced with an inert gas before distillation, and distillation is more preferably performed while supplying the inert gas thereto.

In the method according to the present embodiment, the metal atom may be formulated in the isocyanate composition liquid before or after the distillation purification step or during the distillation step. In addition, at least one compound selected from the group consisting of compounds A to G and carbon dioxide may be formulated in the isocyanate composition liquid before or after the distillation purification step or during the distillation step.

<Purification Method (4) in which Persulfate is Contacted after Distillation>

In the present embodiment, a resultant of the purification method (1) is brought into contact with persulfate. The method for bringing into contact with persulfate is as disclosed in Japanese Unexamined Patent Application Publication No. 2002-363151.

Although the persulfate is not particularly provided that the persulfate includes $HSO_5$ or $SO_5^{2-}$ as anion, examples thereof include persulfates of alkali metals such as Li, Na, K, Rb, and Cs, alkali earth metals such as Mg, Ca, Sr, and Ba, III and IV group metals such as Al, Ga, and Sn, transition metals such as Ti, Zr, V, Cr, Mn, Co, Ni, Cu, and Zn, and rare-earth metals such as Sm, Eu, Tm, and Yb. Preferable examples thereof include $LiHSO_5$, $Li_2SO_5$, $NaHSO_5$, $Na_2SO_5$, $KHSO_5$, $S_2SO_5$, $LiHSO_5$, $Mg(HSO_5)_2$, $MgSO_5$, $Ca(HSO_5)_2$, and $CaSO_5$. These persulfates may be used alone or in combination of at least two kinds thereof. In addition, the persulfate may be used together with another inorganic salt, and may be used in the form of a double salt. Preferable examples of the double salt include $2KHSO_5 \cdot KHSO_4 \cdot K_2SO_4$. The used amount of the persulfate, relative to the isocyanate, is preferably 0.001% by mass to 50% by mass, more preferably 0.05% by mass to 30% by mass, and even more preferably 0.1% by mass to 20% by mass.

As the persulfate, a persulfate supported on a carrier is preferably used. Although the carrier is not particularly limited provided that the carrier can support the persulfate, examples thereof include clay minerals and porous materials. Examples of the clay mineral include compounds containing phyllosilicates of aluminium, iron, magnesium, or alkali metal, such as clay minerals belonging to kaolinite group, montmorillonite-saponite group, mica group, or vermiculite group. Preferable examples thereof include acid earth, activated earth, montmorillonite, and RADIOLITE.

Examples of the porous material include activated carbons and zeolites. The used amount of the carrier, relative to the organic isocyanate, is preferably 0.01% by mass to 100% by mass, more preferably 0.05% by mass to 50% by mass, and even more preferably 0.1% by mass to 20% by mass. Although the method for making the persulfate to be supported on a carrier is not particularly limited, examples thereof include a method in which a persulfate is dissolved in 1 to 100 times its volume of water, followed by gradually adding a carrier thereto at 0° C. to 100° C., drying the resultant material, and then removing water by vacuum distillation while stirring the resultant material until powders obtained, to obtain a supported material in which the persulfate is supported on the carrier. Although the supported material may be used directly as a treatment agent, the supported material may be further burned at 200° C. to 700° C. to be used. In addition, the supported material may be washed with a solvent such as water, methanol, ethanol, acetonitrile, tetrahydrofuran, diethyl ether, or ethyl acetate, before conducting drying. In the preparation method, the weight ratio of persulfate:carrier is preferably 1:1 to 50, and more preferably 1:1 to 20.

Although the solvent is not particularly limited provided that the solvent is inert to an isocyanate group, the solvent may be one or a mixture of at least two kinds of: aromatic-based solvents such as toluene, xylene, monochlorobenzene, and 1,3-dichlorobenzene; ketone-based solvents such as methyl ethyl ketone, methyl isobutyl ketone, and cyclohexanone; ester-based solvents such as ethyl acetate, butyl acetate, isobutyl acetate, and ethyl-3-ethoxy propionate; glycol ether ester-based solvents such as ethylene glycol ethyl ether acetate, propylene glycol methyl ether acetate, 3-methyl-3-methoxy butyl acetate; and ether-based solvents such as tetrahydrofuran and dioxane.

Although the temperature at which a mixture containing the isocyanate and the persulfate are contacted (hereinafter, may be referred to simply as contact) is not particularly limited, the temperature is preferably 50° C. to 150° C., more preferably 70° C. to 140° C., and even more preferably 80° C. to 120° C. Although the time for contact is not particularly limited, the time is generally 30 minutes to 5 hours under nitrogen atmosphere. The method for contact may be a batch-wise treatment or a continuous treatment. Although the contact may be conducted at normal pressure, the contact may be conducted under increase pressure of reduced pressure.

The organic isocyanate obtained by conducting the contact is preferably subjected to additional procedure such as distillation. In the case where distillation or the like is conducted, the persulfate, the carrier, and the like are preferably removed by filtration or the like before distillation. Although the distillation may be conducted by the conventional procedure, the distillation is preferably conducted by thin film distillation using a molecular distillation device. In the case where the thin film distillation is conducted, a component having a low boiling point may be removed by decompression treatment, as needed, before thin film distillation. The thin film distillation is preferably conducted at a pressure of 13.3 Pa or less and a temperature of 80° C. to 250° C., and more preferably at a pressure of 0.000001 to 13.3 Pa and a temperature of 100 to 280° C. The interior of the distillation apparatus is preferably replaced with an inert gas before distillation, and distillation is more preferably performed while supplying the inert gas thereto.

In the method according to the present embodiment, the metal atom may be formulated in the isocyanate composition liquid before or after the distillation purification step or during the distillation step. In addition, at least one compound selected from the group consisting of compounds A to G and carbon dioxide may be formulated in the isocyanate composition liquid before or after the distillation purification step or during the distillation step.

Any one of the methods makes it possible to obtain the composition having a hue of 120 APHA or less, preferably 60 APHA or less, more preferably 30 APHA or less, and even more preferably 25 APHA or less. In the case where the hue value is high, the purification method may be repeatedly conducted.

The isocyanate composition according to the present embodiment has a high purity and shows almost no coloration, and the coloring is suppressed and inhibited when stored for a long time. In addition, the isocyanate composition is excellent in stability (suppressibility of gel generation) even when stored for a long time. Since the isocyanate compound according to the present embodiment has a higher reactivity and a superior weather resistance in comparison with an aliphatic isocyanate due to the presence of the structure (A) and/or the structure (B), the isocyanate composition according to the present embodiment is very useful as a coating raw material, urethane raw material, adhesive agent, or the like.

<Method for Producing an Isocyanate Polymer by Reacting an Isocyanate Compound Having the Structure (A) and/or the Structure (B)>

In the method for producing an isocyanate polymer according to the present embodiment, an isocyanate polymer is obtained using the isocyanate composition. The obtained isocyanate polymer has a unit of the following formula (4) and at least one unit selected from the group consisting of groups represented by the following formulae (5), (6), (7), (8), (9), (10), (11), and (12), and a nitrogen atom constituting the isocyanate polymer bonds to a carbon atom.

 (4)

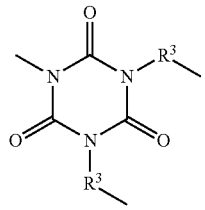 (5)

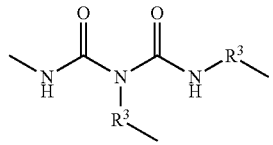 (6)

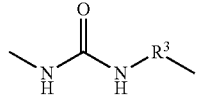 (7)

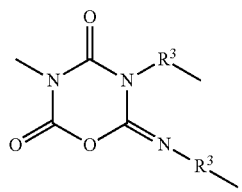 (8)

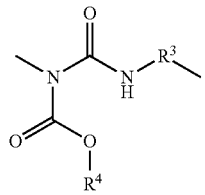 (9)

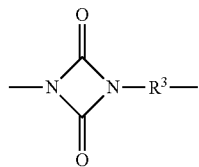 (10)

—N═C═O (11)

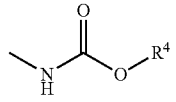 (12)

In the formulae, $R^3$ each independently represents a divalent hydrocarbon group, and $R^4$ each independently represents a monovalent organic group.

As the method for producing an isocyanate polymer according to the present embodiment, a method disclosed in paragraphs [0345] to [0365] of International Patent Application Publication No. WO 2014/069605 is preferably used.

For example, the isocyanurate-forming reaction is preferably conducted in the presence of an isocyanurate-forming catalyst. As the isocyanurate-forming catalyst, basic catalysts are generally preferable, and specific examples thereof include the following compounds.

(i) Hydroxides or organic acid salts (such as acetic acid salts, butyric acid salts, or decanoic acid salts) of tetraalkyl ammonium (such as tetramethylammonium or tetraethylammonium).

(ii) Hydroxide or organic acid salts (such as acetic acid salts, butyric acid salts, or decanoic acid salts) of trialkyl hydroxy alkyl ammonium (such as trimethyl hydroxypropyl ammonium, trimethyl hydroxyethyl ammonium, triethyl hydroxypropyl ammonium, or triethyl hydroxyethyl ammonium).

(iii) Metal salts (such as tin salts, zinc salts, lead salts, sodium salts, or potassium salts) of alkylcarboxylic acids such as acetic acid, capric acid, octylic acid, or myristic acid.

(iv) Alkoxides of metals such as sodium or potassium.

(v) Aminosilyl group-containing compounds (such as hexamethyldisilazane)

(vi) Phosphorus-based compounds such as tributylphosphine.

(vii) Fluorine compounds or hydrogen polyfluoride compounds (such as tetraalkyl ammonium fluorides such as tetramethyl ammonium fluoride hydrate, or tetraethyl ammonium fluoride).

(viii) Compounds constituted by compounds having a structure of the following formula (Y-1) or formula (Y-2) (such as 3,3,3-trifluoropropionic acid; 3,3,4,4,4-pentafluorobutanoic acid; 3,3,4,4,5,5,5-heptafluoropentanoic acid; or 3,3-difluoropropa-2-enoic acid) and either quaternary ammonium ions or quaternary phosphonium ions.

$$R^{119}=CR'-C(=O)O- \quad (Y\text{-}1)$$

$$R^{120}CR'_2-C(=O)O- \quad (Y\text{-}2)$$

(In the formulae, $R^{119}$ and $R^{120}$ each independently represent a C1-30 perfluoroalkyl group, R' each independently represents one selected from the group consisting of a hydrogen atom, a C1-20 alkyl group, and an aromatic group, and these may contain a hetero atom.)

$R^{119}$ and $R^{120}$ may each independently represent a linear, branched, or cyclic saturated perfluoroalkyl group or unsaturated perfluoroalkyl group.

Among these, the catalyst (i) or (ii) is preferable from the viewpoint of catalyst efficiency and selectivity of isocyanurate-forming reaction. The catalyst (vi) is preferably used to form an uretdione structure (the structure of formula (10)) at a high ratio. The catalyst (vii) or the catalyst (viii) is preferably used to form an iminooxadiazinedione structure (the structure of formula (8)) at a high ratio.

Although the amount of the isocyanurate-forming catalyst to be added to the reaction system of the isocyanurate-forming reaction may be appropriately adjusted depending on the kind of the used catalyst or the concentration of other components in the reaction system, the amount, relative to 100 parts by mass of the isocyanate, may be $1.0 \times 10^{-4}$ parts by mass to 1.0 parts by mass, for example. The upper limit of the used amount of the isocyanurate-forming catalyst is preferably $5.0 \times 10^{-1}$ parts by mass or less, more preferably, $1.0 \times 10^{-1}$ parts by mass or less, and even more preferably $2.0 \times 10^{-2}$ parts by mass or less, from the viewpoint of suppressibility of coloring or discoloration or the resultant product and the reaction control. The lower limit of the used amount of the isocyanurate-forming catalyst is more preferably $1.0 \times 10^{-3}$ parts by mass or more, and even more preferably $2.0 \times 10^{-3}$ parts by mass or more, from the viewpoint of reactivity.

The above-mentioned isocyanurate-forming catalyst simultaneously serves as an allophanate-forming catalyst. Thus, it is possible to allow the isocyanurate-forming reaction and the allophanate-forming reaction to proceed simultaneously by adding a hydroxy group-containing compound before or during the isocyanurate-forming reaction.

The hydroxy group-containing compound is preferably a compound having one or two hydroxy groups in a molecule constituted only by carbon, hydrogen and oxygen, and even more preferably a compound having only one hydroxy group. Specific examples of the compound having one hydroxy group include methyl alcohol, ethyl alcohol, propyl alcohol, butyl alcohol, pentyl alcohol, hexyl alcohol, heptyl alcohol, octyl alcohol, and nonyl alcohol, examples of the compound having two hydroxy groups include ethylene glycol, 1,3-butanediol, 1,4-butanediol, neopentyl glycol, and 2-ethyl hexanediol, and two kinds or more may be used together.

Although the reaction temperature of the isocyanurate-forming reaction is not particularly limited, the reaction temperature is preferably 0° C. to 200° C. In the case where the reaction temperature is less than 0° C., the reaction rate is small, which is not practical. In the case where the reaction temperature exceeds 200° C., the side reaction or excessive coloration of the resultant product tends to easily occur. Among the range, the lower limit of the reaction temperature is more preferably 40° C., even more preferably 50° C., and the most preferably 60° C., from the viewpoint of the reaction rate. The upper limit of the reaction temperature is preferably 150° C. from the view point of the coloration of the resultant produce or polyisocyanate, and the reaction temperature is preferably 40° C. to 150° C. The upper limit of the polymerization reaction temperature is more preferably 150° C. or less, even more preferably 120° C., and the most preferably 110° C., from the viewpoint of the coloration of the resultant product.

The reaction time of the isocyanurate-forming reaction is not particularly limited, and the reaction time may be within a range of 10 seconds to 24 hours.

Examples of a confirmation method of the terminal point of the isocyanurate-forming reaction include: a method for measuring the content rate of the isocyanate group (NCO %) in the reaction mixture; a method for measuring a refractive index; and a method by gel permeation chromatography measurement of the reaction mixture.

In the case where the isocyanurate-forming reaction excessively proceeds, the viscosity of the resultant product is increased, the amount proportion of the isocyanurate compound is increased, and a manufactured article having intended physical properties may not be obtained, and therefore, the conversion rate of the reaction (proportion of reacted polyisocyanate, relative to initial amount of polyisocyanate) is preferably limited to 50% or less (more preferably 40% or less, and even more preferably 25% or less). Moreover, from the viewpoint of sufficiently obtaining the yield of the isocyanurate compound, the conversion rate of the reaction is preferably 5% or more, more preferably 10% or more, and more preferably 15% or more.

In the present embodiment, when the isocyanurate-forming reaction reaches the intended conversion rate, a catalyst-terminating agent is added to deactivate the isocyanurate-forming catalyst so that the isocyanurate-forming reaction is terminated. If the catalyst-terminating agent is not added, the isocyanurate-forming reaction further proceeds in the distillation purification of the isocyanate polymer, and the viscosity of the manufactured article may increase and a gel component may be generated. In order to prevent the isocyanurate-forming reaction from proceeding in the distillation purification, it is preferable that the isocyanurate-forming catalyst be deactivated by adding the catalyst-terminating agent. In the present embodiment, since the used amount of the catalyst can be sufficiently suppressed by the addition of the inactive compound (at least one compound selected from the group consisting of compound A to compound G), thermal yellowing and weather resistance can be sufficiently improved even when the catalyst-terminating agent is added. As the catalyst-terminating agent, for example, sulfuric acid, phosphoric acid, acidic phosphate esters, hydrochloric acid, sulfonic acid compounds and the like can be used. In the case where a reaction product of the catalyst-terminating agent and the catalyst is precipitated as a solid, the reaction product is preferably separated by a method such as filtration using a filter or Celite.

Although the isocyanurate-forming reaction may be conducted in the presence or absence of a solvent, the isocyanurate-forming reaction is preferably performed in the presence of a solvent from the viewpoint of easiness in reaction control and operation.

As a solvent available in the isocyanurate-forming reaction, a solvent that is inactive with respect to a polyisocyanate to be used and can dissolve an isocyanate used as a raw material and a resultant isocyanurate compound is selected. Specifically, as the solvent, acetate esters such as ethyl acetate, butyl acetate, and amyl acetate; and aromatic hydrocarbons such as benzene, toluene, xylene, and monochlorobenzene may be used alone or in combination.

Moreover, in the case where the isocyanurate-forming reaction is performed in the absence of a solvent, the unreacted polyisocyanate functions as a solvent and can dissolve the resultant isocyanurate compound when the conversion rate is limited to 50% or less. Thus, the conversion rate of the isocyanurate-forming reaction in the absence of a solvent is preferably 5% to 50%, and more preferably 10% to 40%.

After the completion of the isocyanurate-forming reaction, the isocyanurate compound can be collected by removing the unreacted polyisocyanate and the solvent from the reaction system, for example. A removal method is not particularly limited, and the unreacted polyisocyanate and the solvent can be removed by distillation purification, for example. In addition, the removal is desirably performed at a low temperature, and is preferably performed using a device that has a large evaporation surface with respect to liquid and good evaporation efficiency, such as a falling thin-film evaporator, a thin-film evaporation apparatus, or a molecular distillation apparatus.

The concentration of the polyisocyanate contained in the composition containing the isocyanate polymer is preferably controlled to be 1% by mass or less by performing the removal. The upper limit of the diisocyanate concentration is more preferably 0.7% by mass or less, even more preferably 0.5% by mass or less, and even more further preferably 0.3% by mass or less. In the case where the concentration of the polyisocyanate is the above-described upper limit or less, the toxicity of the composition containing the isocyanate polymer can be further reduced, and the safety can be improved.

In the composition containing the isocyanate polymer including the isocyanurate structure obtained by the method according the present embodiment, the average value of the number of isocyanate groups is preferably 2.3 or more, more preferably 2.5 or more, even more preferably 2.7 or more, further preferably 3.0 or more, and more further preferably 3.2 or more.

In the case where the average value of the number of isocyanate groups is 2.3 or more, a cross-linkage property when used as a curing agent of a coating material can be exhibited.

When performing the isocyanurate-forming reaction, the polyisocyanate, and, as a solvent, a C5-20 hydrocarbon compound, the compound having at least one bond selected from the group consisting of an ether bond and a thioether bond, the halide obtained by substituting at least one hydrogen atom constituting the above-mentioned hydrocarbon compound with a halogen atom, or a compound formed by substituting a portion or a whole of carbon atoms of the hydrocarbon compound or the compound having at least one bond selected from the group consisting of ether and thioether bonds with silicon atoms may each independently be added to the reaction system, or a polyisocyanate composition containing the polyisocyanate and at least one solvent may be prepared in advance and then added to the reaction system.

In addition, a polyisocyanate and a polyol compound may be subjected to urethan-forming reaction (condensation polymerization reaction) to obtain a urethane compound, and then the polyisocyanate and the urethane compound may be subjected to allophanate-forming reaction (reaction in which an isocyanate is added to a urethane bond) to obtain an allophanate compound.

The urethan-forming reaction and the allophanate-forming reaction may be simultaneously performed, or, after the urethan-forming reaction, an allophanate-forming catalyst may be added to the reaction system to conduct allophanate-forming reaction.

Regarding the ratio of the polyisocyanate and to the polyol compound to be subjected to reaction, the mole number of isocyanate groups in the polyisocyanate is preferably 3 to 100, when the mole number of hydroxy groups of the polyol compound is 1. The lower limit of the mole number of isocyanate groups in the polyisocyanate is more preferably 6, even more preferably 8, and the most preferably 10. The upper limit thereof is more preferably 80, even more preferably 60, and the most preferably 30. In the case where the mole number of isocyanate groups is 3 or more, an isocyanate polymer having a low viscosity can be prepared. In the case where the mole number of isocyanate groups of the polyisocyanate is 100 or less, the sufficient production efficiency can be maintained.

The urethan-forming reaction temperature is preferably 20° C. to 200° C. The lower limit of the urethan-forming reaction temperature is more preferably 40° C., even more preferably 50° C., and the most preferably 60° C. The upper limit of the urethan-forming reaction temperature is preferably 160° C., more preferably 140° C., and particularly preferably 120° C. The reaction time is preferably 10 minutes to 24 hours, more preferably 15 minutes to 15 hours, and even more preferably 20 minutes to 10 hours. In the case where the reaction temperature is 20° C. or more, the sufficient reaction rate is obtained, and in the case where the reaction temperature is 200° C. or less, the coloration can be suppressed. The urethane-forming reaction may be performed without a catalyst, or in the presence of a catalyst such as a tin-based catalyst or an amine-based catalyst.

The allophanate-forming reaction may be performed using a known allophanate-forming catalyst. Preferable examples of the catalyst include: a compound containing lead; a compound containing zinc; a compound containing tin; a compound containing zirconium; a compound containing bismuth; and a compound containing lithium. One kind of these catalysts may be used alone, or two or more kinds thereof may be used in combination. The compound containing zinc, the compound containing lead, the compound containing tin, or the compound containing zirconium is preferable, and the compound containing zirconium is more preferable. Examples of the compound containing zirconium include zirconyl naphthenate and zirconyl 2-ethylhexanoate. These are particularly preferable because of being relatively inexpensive and industrially easily-available, and having high selectivity of the allophanate-forming reaction, and furthermore, high safety.

An adding method of the allophanate-forming catalyst is not particularly limited. For example, the allophanate-forming catalyst may be added before manufacturing the urethane compound, that is, before the start of the urethane-forming reaction of a polyisocyanate and a polyol compound, may be added in the middle of the urethane-forming reaction, or may be added after manufacturing the urethane compound by the urethane-forming reaction.

Moreover, as the adding method, a requisite amount of the allophanate-forming catalyst may be added at one time or may be added by dividing into several times. Furthermore, a method in which addition is conducted continuously at a constant addition rate may be adopted.

Generally, the allophanate-forming reaction is performed at 20° C. to 200° C. The lower limit of the reaction temperature at which the allophanate-forming reaction is performed is more preferably 30° C., even more preferably 60° C., and the most preferably 80° C. Moreover, the upper limit of the reaction temperature at which the allophanate-forming reaction is performed is more preferably 180° C., and further preferably 160° C. In the case where the reaction temperature is 20° C. or more, the allophanate-forming reaction can be made to proceed at an appropriate reaction rate without causing side reactions. Furthermore, in the case where the reaction temperature is 200° C. or less, side reactions and coloration tend to be difficult to occur.

In the allophanate-forming reaction to prepare the isocyanate polymer, it is preferable that the conversion rate of a urethane group to an allophanate group be increased as high as possible. The conversion rate is preferably 80% or more, more preferably 90% or more, and even more preferably 92% or more. By sufficiently increasing the conversion rate of a urethane group to an allophanate group, the average value of the number of isocyanate groups (fn) in the isocyanate polymer can be increased while keeping the viscosity relatively low. The average value of the number of isocyanate groups (fn) means a statistical average value of the number of isocyanate groups contained in one molecule of the isocyanate polymer, and is calculated by the following equation.

The average value of the number of isocyanate groups (fn)=(Number average molecular weight of isocyanate polymer×Mass % of isocyanate groups×0.01)/42

The average value of the number of isocyanate groups in the isocyanate polymer containing allophanate groups obtained by such a method is preferably 2.5 or more, more preferably 2.8 or more, even more preferably 3.0 or more, and the most preferably 3.2 or more.

In the case where the average value of the number of isocyanate groups is 2.5 or more, a cross-linkage property when being used as a curing agent for a coating material can be exhibited. Although the urethane-forming reaction and the allophanate-forming reaction can be performed in the absence of a solvent, an organic solvent which does not have the reactivity with the isocyanate groups, such as butyl acetate, methyl ethyl ketone, toluene, xylene, hydrocarbon-based solvents, or aromatic-based solvents, may be used as a solvent as necessary.

Progression of the reaction of a polyisocyanate and a polyol compound can be traced by measuring a concentration of the isocyanate groups of the reaction mixture or measuring a refractive index.

The allophanate-forming reaction can be terminated by being cooled to room temperature or by adding a reaction-terminating agent. In the case of using the allophanate-forming catalyst, it is preferable that the allophanate-forming reaction be terminated by adding the reaction-terminating agent because the stability of the isocyanate polymer is improved.

The additive amount of the reaction-terminating agent is 0.2 to 100 times of molar quantity, preferably 0.5 to 50 times of molar quantity, and more preferably 1.0 to 20 times of molar quantity with respect to the allophanate-forming catalyst. In the case of 0.2 times or more, the allophanate-forming catalyst can be sufficiently deactivated. Moreover, in the case of 100 times or less, occurrence of turbidity or the like of the composition containing the isocyanate polymer due to a residue of the reaction-terminating agent can be sufficiently suppressed.

The reaction-terminating agent is not particularly limited as long as it deactivates the allophanate-forming catalyst. Examples of the reaction-terminating agent include: compounds showing phosphoric acid acidity, such as phosphoric acid, pyrophosphoric acid, metaphosphoric acid, and polyphosphoric acid; monoalkyl esters or dialkyl esters of phosphoric acid, pyrophosphoric acid, metaphosphoric acid, and polyphosphoric acid; halogenated acetic acids such as monochloroacetic acid; benzoyl chloride; sulfonic acid ester; sulfuric acid; sulfate ester; ion-exchange resins; and chelating agents.

Moreover, industrially, as the reaction-terminating agent, phosphoric acid, pyrophosphoric acid, metaphosphoric acid, polyphosphoric acid, phosphoric acid monoalkyl esters, or phosphoric acid dialkyl esters are preferable in terms that they are difficult to corrode stainless steel. Examples of phosphoric acid monoesters and phosphoric acid diesters include phosphoric acid monoethyl ester, phosphoric acid diethyl ester, phosphoric acid monobutyl ester, phosphoric acid dibutyl ester, phosphoric acid mono(2-ethylhexyl)ester, and phosphoric acid di(2-ethylhexyl)ester.

Furthermore, phosphoric acid, pyrophosphoric acid, metaphosphoric acid, and polyphosphoric acid, which are substantially free from water, are more preferable as the reaction-terminating agent. When the reaction-terminating agent substantially free from water is used, a reaction product of the reaction-terminating agent and the catalyst becomes easy to be precipitated, and thus, there is an effect that the reaction product of the reaction-terminating agent and the catalyst becomes difficult to remain in the composition containing the isocyanate polymer.

Furthermore, when the reaction-terminating agent substantially free from water is used, generation of a reaction product of water and an isocyanate can be suppressed, and there are effects that viscosity increase of the composition containing the isocyanate polymer is difficult to occur, and reducibility with respect to an organic solvent is difficult to be decreased. In addition, the term "substantially free from water" means that water may be contained as long as the above-described effects are exhibited, and specifically, less than 5.0% by mass, preferably less than 2.0% by mass, and more preferably less than 0.50% by mass of water may be contained with respect to the reaction-terminating agent.

In addition, as another preferred reaction-termination method when using the allophanate-forming catalyst, there is a method in which a catalyst is adsorbed with an adsorbent. Furthermore, the reaction may be terminated by combining the adsorbent and the above-described reaction-terminating agent. Examples of the adsorbent include silica gel, activated carbon, and activated alumina. The additive amount of the adsorbent is preferably 0.05 to 10% by mass, relative to the mass of the polyisocyanate used in the reaction.

After the completion of the reaction, the unreacted polyisocyanate and the solvent may be separated from the composition containing the isocyanate polymer by treatment such as a thin-film distillation method or a solvent extraction method.

The concentration of the polyisocyanate contained in the composition containing the isocyanate polymer is preferably controlled to be 1% by mass or less by performing the above-described treatment. The upper limit of the polyisocyanate concentration in the composition containing the isocyanate polymer is more preferably 0.7% by mass or less, even more preferably 0.5% by mass or less, and particularly preferably 0.3% by mass or less. By making the polyisocyanate concentration be the above-described upper limit or less, toxicity of the composition containing the isocyanate polymer can be further reduced, and safety can be increased.

These reactions may be performed in one reactor, or in two reactors connected with each other to perform a step of the urethane-forming reaction and a step of the allophanate-forming reaction separately.

It is preferable that the isocyanate composition used according to the present embodiment contain: an isocyanate compound of the formula (1) and/or the formula (2); and a difunctional or more functional isocyanate compound.

In the case where the isocyanate composition contains only a monofunctional isocyanate having one isocyanate group in a molecule thereof as an isocyanate compound of the formula (1) and/or the formula (2), it is preferable that the isocyanate composition further contain difunctional (the term "difunctional" means the presence of two isocyanate groups in one molecule) or more functional isocyanate because the isocyanate concentration can be increased. As the difunctional or more functional isocyanate, a conventionally-known isocyanate may be used, and, for example, aliphatic isocyanates, such as, hexamethylene diisocyanate, isophorone diisocyanate, xylylene diisocyanate, hydrogenated xylylene diisocyanate, hydrogenated MDI, trimer triisocyanate or the like may be used.

In the case where the isocyanate composition contain trifunctional isocyanate having three isocyanate groups in a molecule thereof as an isocyanate compound of the formula (1) and/or the formula (2), a step of collecting unreacted monomer components may be omitted. A mixture liquid (polymer liquid) composed of the monomer of the isocyanate compound according to the present embodiment and the polymer is preferably used. The polymer liquid is industrially advantageous, because the vapor pressure at normal temperature is low (the loss on heating is small) and a distillation procedure is not required. Although the amount of the monomer component may vary depending on the component, the amount, relative to the amount of monomers used in preparation of the polymer, is preferably 1% by mass to 98% by mass, and more preferably 20% by mass to 95% by mass, in view of the viscosity or the like.

<Use of Isocyanate Polymer>

A block isocyanate polymer may be manufactured by using a composition including various isocyanate polymers obtained by the above-described method and blocking a part or all of the isocyanate groups of the isocyanate polymers by a blocking agent.

Moreover, for the purpose of improving water dispersibility, a composition of a hydrophilic group-modified isocyanate polymer, in which a part of the isocyanate groups of various isocyanate polymers obtained by the above-described method is modified by an active hydrogen-containing hydrophilic compound by a conventionally-known method, may also be obtained.

In addition, the isocyanate polymer obtained in the present embodiment may be reacted with a blocking agent and an active hydrogen-containing hydrophilic compound, respectively, when being used as a one-liquid coating material or a cross-linking agent of a coating agent.

<Use of Isocyanate Composition>

As described above, the isocyanate composition according to the present embodiment exhibits effects of improving the stability when being stored. In addition, an isocyanate polymer may be prepared using the isocyanate composition according to the present embodiment. The isocyanate composition according to the present embodiment or the isocyanate polymer may be appropriately used as a raw material of a coating material, adhesive agent, or the like.

It is surprising that, also in the case where a block isocyanate or an active hydrogen-containing hydrophilic compound is made to addition-react using the isocyanate composition obtained according to the present embodiment, the reaction rate is high and coloration of a product after the reaction is suppressed, and a block isocyanate, an oligomer, an adduct, or a polymer-base product (such as, a raw material of a coating material, a reactive diluent, a modifier of a raw material of a coating material, a curing accelerator, a fiber, a film, a sheet, a medical polymer, a composite polymer, a surfactant, or a water-based urethane dispersion) is provided in one embodiment according to the present invention.

<Method for Storing Isocyanate Composition>

In the present embodiment, a method for storing the isocyanate composition is provided. The storing method is a method in which an isocyanate composition containing: an isocyanate compound having at least one of the structure (A) and the structure (B); and 0.002 ppm by mass to 10% by mass, relative to the isocyanate compound, of at least one compound selected from the group consisting of compound A to compound G and carbon dioxide, the compound being different from the isocyanate, is stored for 30 days or more, 60 days or more, 90 days or more, 120 days or more, 150 days or more, 300 days or more, or 600 days or more, for example.

In the storing method, an ISO tank container, a drum, a pail, a storage tank connected with a manufacturing line, a bottle or the like may be appropriately used as a storage container. As a material thereof, stainless steel, polyethylene, polypropylene, thermoplastics resin such as fluorine resin, or glass may be appropriately used. In addition, even if a storage container is made of a material different from the above-described materials, the surface in contact with the isocyanate composition may be coated with, for example, polyethylene, polypropylene, thermoplastics resin such as fluorine resin, glass, phenol resin, epoxy resin, or the like to be used.

It is preferable that the storage temperature be approximately −20° C. to 60° C., more preferably approximately −10° C. to 50° C., and even more preferably 0° C. to 40° C.

By using the storing method, denaturation and chromaticity increase after storage can be prevented.

EXAMPLES

Although the present invention will be described in more detail below by Examples, the present invention is not limited to the following Examples. The terms "part", "%"

and "ppm" mean "parts by mass", "% by mass" and "ppm by mass", respectively, unless otherwise is indicated.

<NCO Amount (NCO %)>

The NCO amount (% by mass) was determined by neutralizing the isocyanate group in the test portion with an excessive amount of 2 N amine and then carrying out back titration with 1 N hydrochloric acid.

<Number Average Molecular Weight>

The number average molecular weight of the test portion was measured by gel permeation chromatography (GPC).

The following method was used in the measurement by GPC.

Apparatus used: HLC-8120 (manufactured by Tosoh Corporation)

Column used: TSK GEL Super H1000, TSK GEL Super H2000, TSK GEL Super H3000 (all of these are manufactured by Tosoh Corporation.)

Concentration of test portion: 5 wt/vol % (50 mg of a test portion was dissolved in 1 mL tetrahydrofuran (THF.))

Carrier: THF,
Detection method: Differential refractometer,
Outflow: 0.6 mL/min,
Column temperature: 30° C.

In producing the calibration curve, polystyrene having a molecular weight of 1,000 to 20,000 was used.

<Liquid Chromatography (LC)>

The measurement method of LC is described below.

Apparatus used: HLC-8120 (manufactured by Tosoh Corporation)

Column used: TSK GEL ODS-5 (manufactured by Tosoh Corporation.)

Carrier: acetonitrile/water=50/50 (vol)
Detection method: UV
Outflow: 1.0 mL/min
Column temperature: 40° C.

<Measurement of Mass Concentration of Isocyanate Monomer in Polyisocyanate Composition>

A 20 mL sample bottle was placed on a digital balance, and an accurately weighted 1 g of a sample was added. Next, an accurately weighted 0.03 to 0.04 g of nitrobenzene (an internal standard solution) was added to the sample bottle. Finally, 9 mL of ethyl acetate was added to the sample bottle and the lid was closed. The mixture was sufficiently stirred and used as the test portion. The test portion was subjected to gas chromatography analysis under the following conditions and the amount of the hexamethylene diisocyanate monomer was analyzed.

Apparatus: "GC-8A" (manufactured by Shimadzu Corporation)
Column: "Silicone OV-17" (manufactured by Shinwa Chemical Industries Ltd.)
Column oven temperature: 120° C.
Injection/detector temperature: 160° C.

<NMR Analyzing Method>

Apparatus: JNM-A400 FT-NMR system (manufactured by JEOL LTD.)

Analysis sample: Approximately 0.3 g of a sample solution was accurately weighted, and approximately 0.7 g of deuterochloroform it or deuterodimethyl sulfoxide and approximately 0.05 g of tetramethyltin, as an internal standard substance, were added thereto and mixed uniformly to obtain an NMR analysis sample.

<Hazen Color Number>

Numerical values obtained by measurement by a Hazen meter are described as the Hazen color number.

<Metal Atom Amount>

The amount of metal atom was analyzed by an inductively coupled plasma mass spectrometry method.

Apparatus: SPQ-8000, manufactured by Seiko Epson Corp., Japan (1) Inductively Coupled Plasma Mass Spectrometry Sample About 0.15 g of sample were ashed with dilute sulfuric acid followed by dissolving the resultant in dilute nitric acid.

(2) Quantitative Analysis Method

Analyses were performed for each standard substance and quantitative analyses were performed on the analysis sample solutions based on the resulting calibration curve.

<General Method: Example of Distillation Purification using Distillation Column>

A sample was supplied into a multi-stage distillation column (selected from structured packing distillation column, random packing distillation column, and plate distillation column). The pressure was controlled at the top portion of the distillation column (absolute pressure), and the heat quantity required for distillation was supplied by a reboiler. After the temperature distribution in the column became stable, a fraction of distillate was removed from a side cut line equipped below the top portion of the column in a height direction. The resultant fraction was analyzed.

<General Method: Example of Distillation Purification Using Thin Film Distillation Apparatus>

An isocyanate liquid to be purified was supplied to a falling thin-film-type molecular distillation device (such as MS-300 type manufactured by SHIBATA SCIENTIFIC TECHNOLOGY LTD.), and a vaporized composition component was caught at the surface of a cooling device and then extracted to a collecting device.

<General Method: Example of Distillation Purification Using a Falling Thin-Film Type Evaporator>

The heat quantity required for distillation was supplied to a falling thin-film type evaporator by a heat medium jacket or a heater, an isocyanate composition to be purified was supplied from an upper portion of the falling thin-film type evaporator, and a vapor phase gas was extracted by countercurrent flow or concurrent flow.

<Quantitative Determination of Denaturation Amount>

100 g of a sample was subjected to pressure filtration using a membrane filter having a pore diameter of 1 μm, and the amount of the residue was determined from the weight values of filter before and after filtration as the denaturation amount (% by mass, relative to 100 g of the sample to be filtrated).

Example 1

A crude lysine isocyanate β-isocyanate ethyl ester (LTI) (with a purity of 80%) was obtained from a L-lysine hydrochloride (with an amino acid purity of 97%) using, as a raw material, a L-lysine hydrochloride synthesized by fermentation (described in International Patent Application Publication No. WO 2008/078448 and Japanese Unexamined Patent Application Publication No. 2012-223092) using sodium oleate as a carbon source. Specifically, 235 g of L-lysine monohydrochloride and 251 g of ethanolamine were mixed, hydrogen chloride gas was circulated at 0.3 L/minute, and heating and stirring was conducted at 100° C. and 40 kPa for 10 hours. After the completion of the reaction, crystallization was conducted in a mixture solvent composed of methanol and n-butanol. The resultant was filtered, and dried at 60° C. under reduced pressure at 50 Pa, to obtain 230 g of lysine β-aminoethyl ester trihydrochloride. 230 g of the obtained lysine β-aminoethyl ester trihydrochloride was mixed with 1150 g of o-dichlorobenzene, and a phosgene gas was blown thereinto for 12 hours while heating the mixture at 130° C. In addition, a nitrogen gas was further blown into the resultant to remove phosgene, and o-dichlorobenzene was distilled away at 1 kPa and 120° C. to obtain 230 g of a crude LTI (with a purity of 80%). 10 g of activated carbon (SHIRASAGI P manufactured by Takeda Pharmaceutical Company Limited., from which moisture was removed) was added to 200 g of the crude LTI, and then heated and stirred. Thereafter, the activated carbon was removed by filtration, distillation was conducted using a falling thin-film-type molecular distillation device (MS 300 type manufactured by SHIBATA SCIENTIFIC TECHNOLOGY LTD.) at 6.6 Pa and at a jacket temperature of 140° C., and then diphenyl ether was added to the resultant such that the amount thereof became 1000 ppm to obtain a purified LTI liquid. The metal atom amount was detection limit or less, and an iron ion was added to the resultant such that the amount thereof became 0.002 ppm. The LTI amount in the purified LTI liquid was 97% by mass, and the hue (APHA) immediately after preparation was 18. 100 g of the purified LTI was put into a 200 mL screw bottle, and then stored under a nitrogen atmosphere for 300 days at 25° C. After the storage, the hue (APHA) was 20. 100 g of the stored sample was filtered under an increased pressure using a PTFE filter having a pore diameter of 1 μm, and the denaturation amount determined from the weight values of filter before and after filtration was 0.5% by mass.

Example 2

DURANATE (TKA-100 manufactured by Asahi Kasei Corporation), which is a mixture of uretdione and isocyanurate of hexamethylene diisocyanate, was added to the purified LTI liquid obtained by the same way as Example 1, such that the amount thereof became 20 ppm. The prepared isocyanate composition was evaluated in the same manner as that of Example 1. The results are shown in Table 1.

Synthesis Example A1

Compound Having UV Absorption in the Area of Decamer or Higher Isocyanates 15.3 mg of 2,2,2-trifluoroethoxy titanium (IV) trichloride ($6.0 \times 10^{-2}$ mmol) and 0.5 ml of lysine triisocyanate (LTI) were reacted under a nitrogen atmosphere for 1 hour at 25° C. The reaction product was a compound having an UV absorption in an area of decamer or higher isocyanates in a measurement spectrum of gel permeation chromatography.

In FIG. 1, horizontal axis indicates the retention time in the gel permeation chromatography, and the vertical axis indicates the absorption measured by the UV detector (at the wavelength of 254 nm). The retention time indicated as LTI decamer shows the retention time of the molecular weight corresponding to LTI decamer, and the retention time indicated as LTI shows the retention time of the molecular weight corresponding to LTI. The compound having an UV absorption in an area of decamer or higher isocyanates in a measurement spectrum of gel permeation chromatography obtained in Synthesis Example A1 was a compound having a peak at the retention time of 8.598 minutes in the gel permeation chromatograp in FIG. 1.

Example 3

Preparation of Isocyanate Composition

The purified LTI liquid obtained in Example 1 and the compound obtained in Synthesis Example A1 were mixed to prepare an isocyanate composition. The concentration of the compound having an UV absorption in the area of decamer or higher isocyanates, relative to the isocyanate compound, was 3 ppm. The prepared isocyanate composition was evaluated by the same way as that of Example 1. The results are shown in Table 1.

Synthesis Example A2

100 g of LTI (374 mmol) and 70.4 g of phenol (750 mmol) were reacted by conducting heating under a nitrogen atmosphere at 100° C. When the reaction product was analyzed by liquid chromatography to confirm the amount of the remaining phenol, the amount thereof was the detection limit or less. The reaction product was used as a carbamate group-containing compound according to the present embodiment.

Synthesis Example A3

100 g (677 mmol) of L-lysine, 300 g of phenol, and 100 g of toluene were mixed in a four-necked flask made of glass, having an internal volume of 1 L, and being equipped with a Dean-Stark tube, a distillation tube, and a receiver, the vapor phase in the reactor was replaced with nitrogen, and the mixture was heated at 100° C. to obtain a uniform solution. 10 g of a sulfuric acid was added to the resultant, the pressure in the system was reduced, and produced water was distilled away while refluxing toluene. It was confirmed that approximately 12 g of water was removed, and then the system was further decompressed such that a redundant phenol was distilled away. As a result of $^1$H-NMR analysis, the residue was lysine phenyl ester. The residue containing the lysine phenyl ester was dissolved in 1300 g of o-dichlorobenzene, and a phosgene gas was blown thereinto for 12 hours while conducting heating at 130° C. Nitrogen gas was further blown into the resultant to remove phosgene, o-dichlorobenzene was distilled away at 1 kPa and 120° C., and the resultant mixture was subjected to distillation purification to obtain 2,6-diisocyanatohexanoate phenyl.

Examples 4-52, Comparative Examples 1-11

In the examples and comparative examples described below, isocyanates were obtained by the same way as that of Example 1 except that the amounts of raw amino acids and stabilizers were changed as shown in the tables. The crude isocyanate compound was purified by any of the purification methods (1) to (4) described in the present specification, and the amount of at least one of a compound having an UV absorption at an area of decamer or more, compounds of the formula (3), compounds having at least one bond selected from the group consisting of an ether bond and a thioether bond, carbamate group-containing compounds, carbonic acid esters, basic amino compounds, halogen ions, hydrolyzable halogen compounds, saturated and/or unsaturated hydrocarbon compounds having a linear-chain, branched-chain, or cyclic structure, phosphoric acids, phosphoric acid esters, sulfuric acids, sulfuric acid esters, difunctional isocyanates, metal atoms, and carbon dioxide was adjusted, during preparation, before purification, or after purification. Addition was conducted during preparation in Examples 35 to 39, and before purification in Examples 31 to 34, and each amount was measured after purification. Addition was conducted after purification to adjust the amount in Examples 1 to 30 and 40 to 52 and Comparative Examples.

An iron oxide, cobalt oxide, copper oxide, nickel oxide, lead monoxide, titanium oxide, or palladium on carbon was respectively used as the "metal atoms" of iron, cobalt, copper, nickel, lead, titanium, palladium (Pd), or sodium (Na).

In the case where a compound obtained by reaction of an isocyanate and a phenol was used as a carbamate group-containing compound according to the present embodiment as in Synthesis Example A2, the compound was indicated as a "reaction product of isocyanate and phenol".

In the synthesis of the "reaction product of isocyanate and phenol", an isocyanate contained in the isocyanate composition was used as the isocyanate, and a two equivalent amount of a hydroxy compound (aromatic hydroxy compound or alcohol), relative to isocyanate groups of the isocyanate, was used.

A compound synthesized by the same way as that of Synthesis Example A1 except that an isocyanate contained in the isocyanate composition was used instead of LTI was used as the "compound having an UV absorption in the area of decamer or higher isocyanates".

DURANATE TPA-100, TKA-100, and TLA-100, manufactured by Asahi Kasei Corporation, were used as compounds containing an isocyanurate group and/or a biuret group.

In the tables, the amount of a compound contained in the composition was indicated by the amount, relative to the isocyanate compound.

Results are shown in the following tables.

In the tables, "-" indicates the detection limit or less (in the case of metal atom, <0.001 ppm is indicated), and the amount of carbon dioxide was indicated by a value calculated from weight increase from before to after introduction of carbon dioxide.

Regarding optical isomers, although D- or L-may be indicated at the name of raw material, the configuration is not indicated in the formula of isocyanate. It is presumed that the configuration of raw material was maintained. Although there was a case where the kind and the amount of metal contained in raw amino acid were the same as those of metal contained in the isocyanate composition, the value was indicated after adjusting the amount decreased during preparation.

TABLE 1

| Example | Isocyante raw material Fermentation/ Synthesis | Isocyante raw material Raw amino acid | Purity of amino acid after purification (%) | Amount of each components in isocyanate composition (% by mass or ppm by mass) Isocyanate structure | Isocyanate compound (% by mass) |
|---|---|---|---|---|---|
| 1 | Fermentation | L-Lysine | 98 | 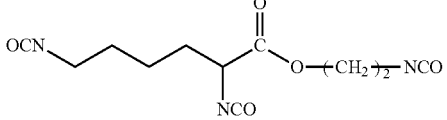 | 97 |
| 2 | Fermentation | L-Lysine | 98 | 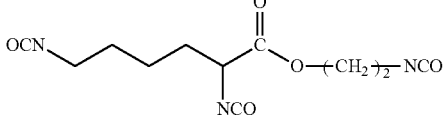 | 96 |
| 3 | Fermentation | L-Lysine | 98 | 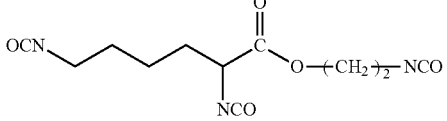 | 96 |
| 4 | Fermentation | L-glutamic acid | 97 | 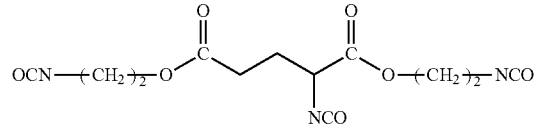 | 97 |
| 5 | Fermentation | L-Lysine | 98 | 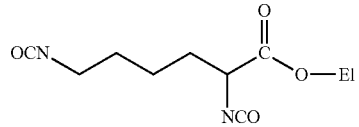 | 99 |

TABLE 1-continued

| | | | | | |
|---|---|---|---|---|---|
| 6 | Synthesis optical resolution | D-glutamic acid | 97 | 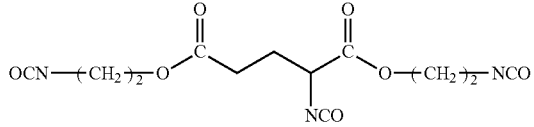 OCN—(CH₂)₂—O—C(=O)—...—C(=O)—O—(CH₂)₂—NCO (with NCO) | 98 |

| | | Amount of each components in isocyanate composition (% by mass or ppm by mass) | | | APHA | | Stability denaturation |
|---|---|---|---|---|---|---|---|
| | Metal atom | | | | | Hue value after storing for a long time. | amount: % by mass Value in |
| | Kind of | | | | Hue value | Value in | parenthesis |
| Example | metal in composition | Amount in composition (ppm) | Compound | Amount (ppm) | immediately after preparation | parenthesis indicates storage period at 25° C. | indicates storage period at 25° C. |
| 1 | Iron | 0.002 | 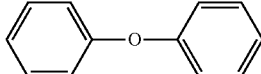 diphenyl ether | 1000 | 18 | 20 (300) | 0.08 (300) |
| 2 | — | — | TKA-100 | 20 | 17 | 19 (300) | 0.06 (300) |
| 3 | — | — | Isocyanate compound having UV absorption at an area of decamere or higher | 3 | 17 | 19 (300) | 0.07 (300) |
| 4 | Nickel | 0.002 | 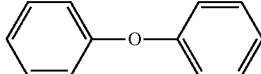 diphenyl ether | 1000 | 18 | 20 (300) | 0.05 (300) |
| 5 | Cobalt Nickel | 0.002 0.003 | 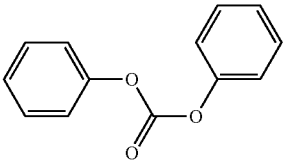 [SMILES: O=C(Oc1ccccc1)Oc1ccccc1] diphenyl carbonate | 100 | 15 | 20 (300) | 0.08 (300) |
| 6 | Iron Nickel | 0.003 0.002 | 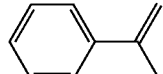 α-methylstyrene | 70 | 20 | 30 (300) | 0.1 (300) |

TABLE 2

| | Isocyante raw material | | Purity of amino acid after purification (%) | Amount of each components in isocyanate composition (% by mass or ppm by mass) | |
|---|---|---|---|---|---|
| | Fermentation/ Synthesis | Raw amino acid | | Isocyanate structure | Metal Atom Isocyanate compound (% by mass) |
| Example 7 | Fermentation | L-Lysine HCl | 98 | 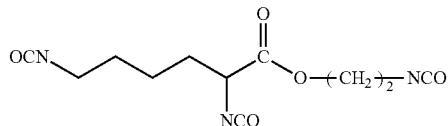 | 98 |

TABLE 2-continued

| | | | | Structure | |
|---|---|---|---|---|---|
| Example 8 | Fermentation | L-Lysine HCl / L-Lysine HCl | 90 / 90 | OCN–(CH₂)₄–CH(NCO)–C(=O)–O–(CH₂)₂–NCO ; OCN–(CH₂)₄–CH(NCO)–C(=O)–O–(p-tolyl) | 99 / 10 |
| Example 9 | Fermentation | L-Lysine HCl | 97 | OCN–(CH₂)₄–CH(NCO)–C(=O)–O–(CH₂)₂–NCO | 97 |
| Example 10 | Fermentation | L-Lysine HCl | 98 | OCN–(CH₂)₄–CH(NCO)–C(=O)–O–(CH₂)₂–NCO | 98 |

| | Amount of each components in isocyanate composition (% by mass or ppm by mass) | | | | APHA | | Stability |
|---|---|---|---|---|---|---|---|
| | Metal atom | | Compound | | Hue value immediately after preparation | Hue value after storing for a long time. Value in parenthesis indicates storage day period at 25° C. | Denaturation amount: % by mass Value in parenthesis indicates storage day period at 25° C. |
| | Kind of metal in composition | Amount in composition (ppm by mass) | Compound | Amount (ppm by mass) | | | |
| Example 7 | Titanium | 3 | OCN–(CH₂)₄–CH(NCO)–C(=O)–O–(CH₂)₂–NH–C(=O)–O–phenyl ; diphenyl carbonate | 2000 / 500 | 18 | 20 (300) | 0.1 (300) |
| Example 8 | — | — | Et–O–C(=O)–O–Et ; Compound having UV absorption at an area of decamere or higher isocyanate | 800 / 500 | 20 | 23 (300) | 0.04 (300) |
| Example 9 | Iron / Nickel | 0.001 / 0.002 | 1-Octene | 1000 | 18 | 20 (300) | 0.06 (300) |
| Example 10 | Iron | 0.01 | OCN–(CH₂)₄–CH(NCO)–C(=O)–O–(CH₂)₂–NH–C(=O)–O–phenyl | 2 | 18 | 35 (300) | 0.06 (300) |

TABLE 3

| | Isocyante raw material | | Purity of amino acid | Amount of each components in isocyanate composition (% by mass or ppm by mass) | |
|---|---|---|---|---|---|
| | Fermentation/ Synthesis | Raw amino acid | after purification (%) | Isocyanate structure | Metal Atom Isocyanate compound (% by mass) |
| Example 11 | Synthesis | DL-glutamic acid | 99 | 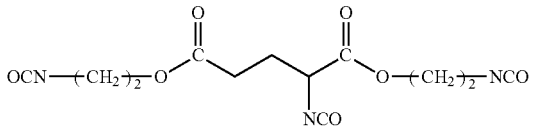 OCN—(CH₂)₂—O—C(=O)—CH₂—CH₂—CH(NCO)—C(=O)—O—(CH₂)₂—NCO | 99 |
| Example 12 | Fermentation | L-α-alanine | 97 | 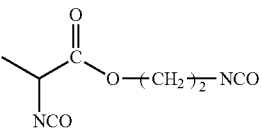 CH₃—CH(NCO)—C(=O)—O—(CH₂)₂—NCO | 99 |
| Example 13 | Fermentation | glycine | 98 | 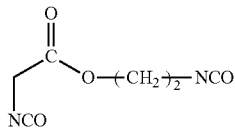 OCN—CH₂—C(=O)—O—(CH₂)₂—NCO | 99 |
| Example 14 | Fermentation | β-alanine | 95 | 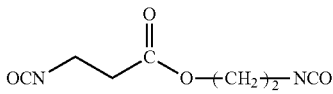 OCN—CH₂—CH₂—C(=O)—O—(CH₂)₂—NCO | 98 |

| | Amount of each components in isocyanate composition (% by mass or ppm by mass) | | | | Hue value immediately after preparation | APHA Hue value after storing for a long time. Value in parenthesis indicates storage day period at 25° C. | Stability Denaturation amount: % by mass Value in parenthesis indicates storage day period at 25° C. |
|---|---|---|---|---|---|---|---|
| | Metal atom | | Compound | | | | |
| | Kind of metal in composition | Amount in composition | Compound | Amount (ppm by mass) | | | |
| Example 11 | Zinc | 0.002 | imidazole | 50 | 18 | 30 (300) | 0.06 (150) |
| Example 12 | Cobalt | 0.005 | Benzyl butyl phthalate Carbon dioxide | 50 50 | 19 | 30 (300) | 0.8 (300) |
| Example 13 | Copper Iron | 3 7 | Chloride ion Reaction product of isocyanate and methanol | 8 30 | 30 | 40 (30) | 0.18 (30) |
| Example 14 | Pd Copper | 0.001 9 | methyl carbonate | 2 | 40 | 60 (30) | 1.8 (30) |

TABLE 4

| Example | Isocyante raw material - Fermentation/Synthesis | Isocyante raw material - Raw amino acid | Purity of amino acid after purification (%) | Isocyanate structure | Isocyanate compound (% by mass) |
|---|---|---|---|---|---|
| 15 | Fermentation | L-aspartic acid | 97 | 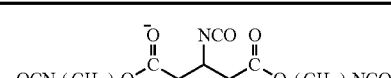 | 97 |
| 16 | Fermentation | L-Lysine HCl | 98 | 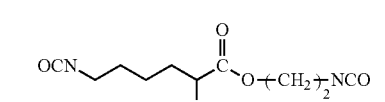 | 90 |
| 17 | Fermentation | L-Lysine HCl | 98.5 | 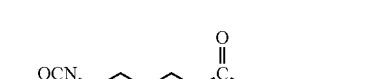 | 97 |
| 18 | Fermentation | 2,6-diamino-heptane-dioic acid | 90 |  | 90 |

| Example | Metal atom - Kind of metal in composition | Metal atom - Amount in composition (ppm) | Compound | Amount (ppm) | Hue value immediately after preparation | APHA Hue value after storing for a long time. Value in parenthesis indicates storage period at 25° C. | Stability Denaturation amount: % by mass Value in parenthesis indicates storage period at 25° C. |
|---|---|---|---|---|---|---|---|
| 15 | Iron | 3 | Benzyl-Toluene | 1000 | 20 | 30 (150) | 0.1 (150) |
| 16 | Iron | 0.002 |  | 100 | 18 | 20 (150) | 0.09 (150) |
|  |  |  | 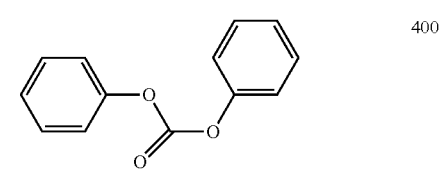 | 400 |  |  |  |
|  |  |  | MTBT | 100 |  |  |  |

TABLE 4-continued

| | | | | | | | | |
|---|---|---|---|---|---|---|---|---|
| 17 | Iron | 0.15 | Benzyl-Toluene | 700 | 18 | 19 (300) | 0.08 (300) | |
| | | | 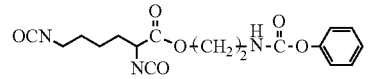 | 100 | | | | |
| | | | 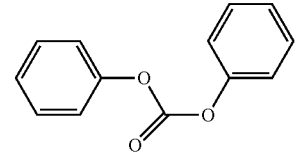 [SMILES: O=C(Oc1ccccc1)Oc1ccccc1] | 100 | | | | |
| 18 | Nickel<br>Iron<br>Na | 2<br>2<br>1 | Decane<br>propane-22-diyldibenzene<br>Diethylene glycol dimethyl ether | 1000<br>1000<br>1000 | 45 | 50 (30) | 0.18 (30) | |

TABLE 5

| | Isocyante raw material | | Purity of amino acid after purification (%) | Amount of each components in isocyanate composition (% by mass or ppm by mass) | Isocyanate compound (% by mass) |
|---|---|---|---|---|---|
| Example | Fermentation/ Synthesis | Raw amino acid | | Isocyanate structure | |
| 19 | Fermentation | L-glutamic acid | 97 | 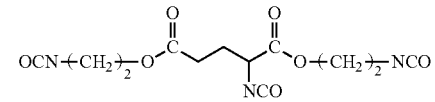 | 97 |
| 20 | Fermentation | glycine | 98 | 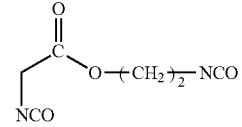 | 98 |
| 21 | Fermentation | L-Lysine HCl | 98.5 | 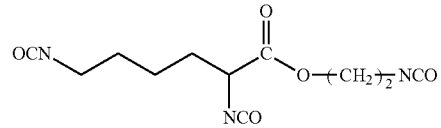 | 97 |

| | Amount of each components in isocyanate composition (% by mass or ppm by mass) | | | | Hue value immediately after preparation | APHA Hue value after storing for a long time. Value in parenthesis indicates storage period at 25° C. | Stability Denaturation amount: % by mass Value in parenthesis indicates storage period at 25° C. |
|---|---|---|---|---|---|---|---|
| | Metal atom | | | | | | |
| Example | Kind of metal in composition | Amount in composition (ppm) | Compound | Amount (ppm) | | | |
| 19 | Iron<br>Nickel | 1<br>0.05 | 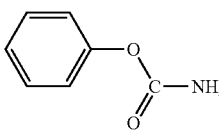 | 400 | 19 | 20 (150) | 0.09 (150) |
| | | | DBU<br>Carbon dioxide | 50<br>100 | | | |

TABLE 5-continued

| 20 | Copper | 0.11 | THF | 10 | 18 | 20 (150) | 0.09 (150) |

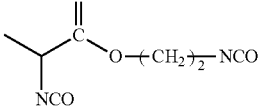

20

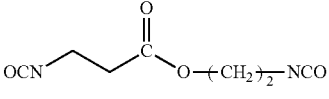

200

| 21 | Tin | 0.205 | Bromide ion | 50 | 18 | 20 (150) | 0.09 (150) |

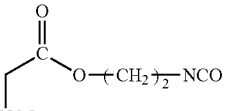

200

TABLE 6

| | Isocyante raw material | | | Amount of each components in isocyanate composition (% by mass or ppm by mass) | |
|---|---|---|---|---|---|
| Example | Fermentation/ Synthesis | Raw amino acid | Purity of amino acid after purification (%) | Isocyanate structure | Isocyanate compound (% by mass) |
| Example 22 | Fermentation | L-α-alanine | 97 | 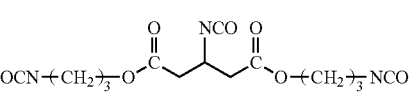 | 99 |
| Example 23 | Fermentation | β-alanine | 97 | OCN-CH₂CH₂-C(O)-O-(CH₂)₂-NCO | 99 |
| Example 24 | Fermentation | glycine | 98 | NCO-CH₂-C(O)-O-(CH₂)₂-NCO | 99 |
| Example 25 | Fermentation | L-aspartic acid | 97 | OCN-(CH₂)₃-O-C(O)-CH₂-CH(NCO)-C(O)-O-(CH₂)₃-NCO | 97 |

TABLE 6-continued

| | Amount of each components in isocyanate composition (% by mass or ppm by mass) | | | | APHA | | Stability Denaturation amount: % by mass Value in parenthesis indicates storage period at 25° C. |
|---|---|---|---|---|---|---|---|
| | Metal atom | | Compound | | Hue value immediately after preparation | Hue value after storing for a long time. Value in parenthesis indicates storage period at 25° C. | |
| Example | Kind of metal in composition | Amount in composition (ppm by mass) | Compound | Amount (ppm by mass) | | | |
| Example 22 | Iron | 7 | Choride ion<br>Bu—O—C(=O)—O—Bu | 1000<br>1000 | 80 | 85 (300) | 1.5 (30) |
| Example 23 | Cobalt | 0.005 | Hexadecane<br>Imidazole | 10<br>1 | 20 | 25 (300) | 1.0 (300) |
| Example 24 | Cooper<br>Iron | 7<br>3 | Reaction product of isocyanante and 1-butanol | 200 | 40 | 45 (30) | 2 (30) |
| Example 25 | Iron<br>Nickel | 1<br>0.05 | di-p-tolylmethane<br>Dibenzyl ether<br>(diphenyl carbonate) | 300<br>200<br>500 | 18 | 20 (300) | 0.06 (300) |

TABLE 7

| | Isocyante raw material | | | Amount of each components in isocyanate composition (% by mass or ppm by mass) | |
|---|---|---|---|---|---|
| Example | Fermentation/ Synthesis | Raw amino acid | Purity of amino acid after purification (%) | Isocyanate structure | Isocyanate compound (% by mass) |
| Example 26 | Fermentation | β-alanine | 97 | OCN–CH₂CH₂–C(=O)–O–(CH₂)₂–NCO | 99 |
| Example 27 | Fermentation | L-methionine | 97 | CH₃–S–CH₂CH₂–CH(NCO)–C(=O)–O–(CH₂)₂–NCO | 99 |
| Example 28 | Fermentation | L-Lysine | 98 | OCN–(CH₂)₄–CH(NCO)–C(=O)–O–Et | 99 |

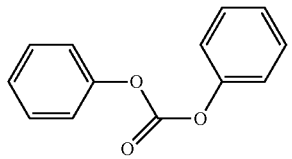 [SMILES: O=C(Oc1ccccc1)Oc1ccccc1]

TABLE 7-continued

| Example | Fermentation/Synthesis | Raw amino acid | Purity | Isocyanate structure | Isocyanate compound (% by mass) |
|---|---|---|---|---|---|
| Example 29 | Fermentation | L-Lysine | 98 | OCN—(CH₂)₄—CH(NCO)—C(=O)—O—(CH₂)₂—NCO | 97 |

| | Amount of each components in isocyanate composition (% by mass or ppm by mass) | | | | APHA | Stability |
|---|---|---|---|---|---|---|
| | Metal atom | | Compound | | Hue value immediately after preparation | Hue value after storing for a long time. Value in parenthesis indicates storage period at 25° C. | Denaturation amount: % by mass Value in parenthesis indicates storage period at 25° C. |
| Example | Kind of metal in composition | Amount in composition (ppm by mass) | Compound | Amount (ppm by mass) | | | |
| Example 26 | Cobalt | 0.002 | Reaction porduct of isocyante and ethanol Benzyl butyl phthalate | 5 / 5 | 30 | 45 (300) | 0.2 (300) |
| Example 27 | Lead | 0.5 | Diphenyl ether (structure) | 5000 | 90 | 100 (300) | 0.5 (30) |
| Example 28 | Titanium | 2 | Dioctadecyl phthalate | 30 | 19 | 30 (300) | 1.1 (300) |
| Example 29 | Iron | 0.1 | Dibutylphosphoric acid / DURANATE TLA-100 (manufactured by Asahi Kasei Corporation) / Compound having UV absorpotion at an area of decamere or higher isocyante. | 30 / 400 / 400 | 19 | 20 (300) | 0.9 (300) |

TABLE 8

| | Amount of each components in isocyanate composition (% by mass or ppm by mass) | | | | | | |
|---|---|---|---|---|---|---|---|
| | Isocyante raw material | | Purity of amino acid after purification (%) | | Isocyanate compound (% by mass) | Metal atom | |
| Example | Fermentation/Synthesis | Raw amino acid | | Isocyanate structure | | Kind of metal in composition | Amount in composition (ppm) |
| 30 | Fermentation | L-α-alanine | 97 | (CH₃)₂CH(NCO)—C(=O)—O—(CH₂)₂—NCO | 99 | Iron | 7 |
| 31 | Fermentation | L-Lysine | 98 | OCN—(CH₂)₄—CH(NCO)—C(=O)—O—Et | 99 | Titanium | 3 |

TABLE 8-continued

| | | | | APHA | Stability |
|---|---|---|---|---|---|
| | | Compound | | Hue value immediately | Hue value after storing for a long time. Value in parenthesis | Denaturation amount: % by mass Value in parenthesis |
| Example | Compound | Amount (ppm) | after preparation | indicates storage period at 25° C. | indicates storage period at 25° C. |
| 30 | — | — | 100 | 130 (30) | 1.2 (30) |
| 30 | — | — | 19 | 30 (300) | 1.1 (300) |

TABLE 9

| | Isocyante raw material | | | Amount of each components in isocyanate composition (% by mass or ppm by mass) | |
|---|---|---|---|---|---|
| Example | Fermentation/ Synthesis | Raw amino acid | Purity of amino acid after purification (%) | Isocyanate structure | Isocyanate compound (% by mass) |
| Example 32 | Fermentation | L-Lysine | 98 | OCN–(CH₂)₄–CH(NCO)–C(=O)–O–(CH₂)₂–NCO | 99 |
| Example 33 | Fermentation | glycine | 98 | OCN–CH₂–C(=O)–O–(CH₂)₂–NCO | 99 |
| Example 34 | Enzyme reaction | γ-aminobutyric acid | 99 | OCN–(CH₂)₃–C(=O)–O–(CH₂)₂–NCO | 92 |
| | | | 99 | OCN–(CH₂)₃–C(=O)–O–C₆H₅ | 8 |
| Example 35 | Synthesis optical resolution | D-glutamic acid | 97 | OCN–(CH₂)₂–O–C(=O)–CH₂–CH(NCO)–C(=O)–O–(CH₂)₂–NCO | 99 |

| | Amount of each components in isocyanate composition (% by mass or ppm by mass) | | | | APHA | Stability |
|---|---|---|---|---|---|---|
| | Metal atom | | Compound | | Hue value immediately after preparation | Hue value after storing for a long time. Value in parenthesis indicates storage period at 25° C. | Denaturation amount: % by mass Value in parenthesis indicates storage period at 25° C. |
| Example | Kind of metal in composition | Amount in composition (ppm by mass) | Compound | Amount (ppm by mass) | | | |
| Example 32 | — | — | Imidazole | 10 | 15 | 21 (150) | 0.8 (150) |
| Example 33 | — | — | DURANATE TKA-100 (manufactured by Asahi Kasei Corporation) Compound having UV absorpotion at an area of decamere or higher isocyante. | 100  20 | 21 | 22 (300) | 0.21 (300) |

TABLE 9-continued

| | | | | | | | |
|---|---|---|---|---|---|---|---|
| Example 34 | — | — | Di(2-ethylhexyl) Sebacate<br>Sulfuric acid<br>Dibenzyl ether | 1000<br>5<br>500 | 22 | 23 (300) | 0.12 (300) |
| Example 35 | — | — | 2-ethylhexlphosphoric acid | 40 | 18 | 20 (300) | 0.08 (300) |

TABLE 10

| | Isocyante raw material | | | Amount of each components in isocyanate composition (% by mass or ppm by mass) | | | |
|---|---|---|---|---|---|---|---|
| | Fermentation/ Synthesis | Raw amino acid | Purity of amino acid after purification (%) | Isocyanate structure | Isocyanate compound (% by mass) | Kind of metal in composition | Metal atom Amount in composition (ppm by mass) |
| Example 36 | Fermentation | L-Lysine | 98 | 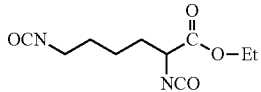 | 99 | — | — |
| Example 37 | Enzyme reaction | γ-aminobutyric acid | 99 | 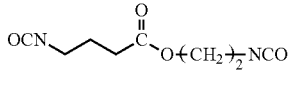 | 99 | — | — |
| Example 38 | Fermentation | L-Lysine | 98 | 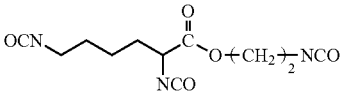 | 97 | — | — |
| Example 39 | Fermentation | β-alanine | 95 | 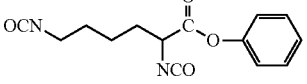 | 97 | — | — |

| | Compound | | APHA | | Stability |
|---|---|---|---|---|---|
| | Compound | Amount (ppm by mass) | Hue value immediately after preparation | Hue value after storing for a long time. Value in parenthesis indicates storage period at 25° C. | Denaturation amount: % by mass Value in parenthesis indicates storage period at 25° C. |
| Example 36 | Di(2-ethyl-hexyl) Sebacate | 800 | 18 | 20 (300) | 0.10 (300) |
| Example 37 | Benzyltoluene<br>Trimethylolpropane trilaurate | 80<br>500 | 18 | 20 (300) | 0.09 (300) |
| Example 38 | Butylnaphthalene<br>Di(2-ethyl-hexyl) Sebacate | 400<br>500<br>240 | 17 | 17 (300) | 0.06 (300) |
| Example 39 | 2-ethylhexl- phosphoric acid<br>Compound having UV absorpotion at an area of decamere or higher isocyante<br>Lauryl Phosphate | 60<br>25<br>10 | 18 | 20 (300) | 0.08 (300) |

TABLE 11

| Isocyanate raw material | | | | Amount of each components in isocyanate composition (% by mass or ppm by mass) | | | |
|---|---|---|---|---|---|---|---|
| Fermentation/ Synthesis | Raw amino acid | Purity of amino acid after purification (%) | Isocyanate structure | Isocyanate compound (% by mass) | Metal atom | | |
| | | | | | Kind of metal in composition | Amount in composition (ppm by mass) | |
| Example 40 | Synthesis | D-methionine | 97 | 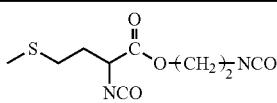 | 97 | — | — |
| Example 41 | Fermentation | β-alanine | 95 | 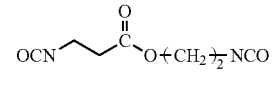 | 98 | Na | 1 |
| Example 42 | Fermentation | L-Lysine | 98 | 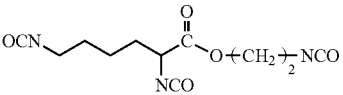 | 99 | — | — |
| Example 43 | Fermentation | L-Lysine | 98 | 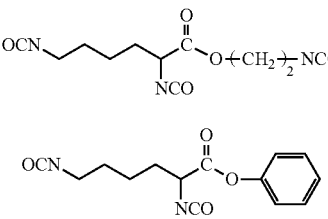 | 96 | — | — |
| | | | 98 | 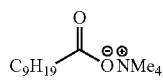 | 3 | | |

| | Compound | Amount (ppm by mass) | Hue value immediately after preparation | APHA Hue value after storing for a long time. Value in parenthesis indicates storage period at 25° C. | Stability Denaturation amount: % by mass Value in parenthesis indicates storage period at 25° C. |
|---|---|---|---|---|---|
| Example 40 | C₉H₁₉-C(=O)-O⁻ NMe₄⁺ Phosphoric acid | 10 30 | 19 | 20 (300) | 0.09 (300) |
| Example 41 | Indecyl phosphoric acid | 150 | 18 | 20 (300) | 0.08 (300) |
| Example 42 | Dibutylphosphoric acid DURANATE TLA-100 (manufactured by Asahi Kasei Corporation) Compound having UV absorpotion at an area of decamere or higher isocyante. | 35 650 10 | 15 | 18 (300) | 0.03 (300) |
| Example 43 | Dibutylphosphoric acid DURANATE TLA-100 (manufactured by Asahi Kasei Corporation) Reaction product of isocyante and phenol Benzyltoluene Diphenyl carbonate | 50 800 100 50 50 | 20 18 | 18 (300) 20 (300) | 0.03 (300) 0.08 (300) |

TABLE 12

| Example | Isocyante raw material | | Purity of amino acid after purification (%) | Amount of each components in isocyanate composition (% by mass or ppm by mass) | |
|---|---|---|---|---|---|
| | Fermentation/ Synthesis | Raw amino acid | | Isocyanate structure | Isocyanate compound (% by mass) |
| Example 44 | Fermentation | D-glutamic acid | 97 | OCN—(CH$_2$)$_2$—O—C(=O)—CH$_2$—CH(NCO)—C(=O)—O—(CH$_2$)$_2$—NCO | 96 |
| | | glycine | 99 | OCN—CH$_2$—C(=O)—O—(CH$_2$)$_2$—NCO | 4 |
| Example 45 | Fermentation | L-aspartic acid | 97 | OCN—(CH$_2$)$_3$—O—C(=O)—CH(NCO)—C(=O)—O—(CH$_2$)$_3$—NCO | 97 |
| | | γ-aminobutyric acid | 98 | OCN—CH$_2$CH$_2$—C(=O)—O—(CH$_2$)$_2$—NCO | 2 |

| Example | Amount of each components in isocyanate composition (% by mass or ppm by mass) | | | | Hue value immediately after preparation | APHA Hue value after storing for a long time. Value in parenthesis indicates storage period at 25° C. | Stability Denaturation amount: % by mass Value in parenthesis indicates storage period at 25° C. |
|---|---|---|---|---|---|---|---|
| | Metal atom | | Compound | Amount (ppm by mass) | | | |
| | Kind of metal in composition | Amount in composition (ppm by mass) | Compound | | | | |
| Example 44 | Iron | 5 | Phenylphosphonic Acid | 30 | 20 | 20 (300) | 0.08 (300) |
| | | | Compound having UV absorpotion at an area of decamere or higher isocyante | 200 | | | |
| | | | Ortho-dichlorobenzene | 550 | | | |
| | | | Chlorine | 5 | | | |
| | | | Reaction product of isocyante and 1-butanol. | 500 | | | |
| Example 45 | | | 2-Ethylhexyl phosphate | 50 | 20 | 20 (300) | 0.08 (300) |
| | | | Compound having UV absorpotion at an area of decamere or higher isocyante | 100 | | | |
| | | | Hexadecane | 200 | | | |
| | | | Diazabicycloundecene | 50 | | | |
| | | | Dimethyl carbonate | 500 | | | |

TABLE 13

| Example | Isocyante raw material Fermentation/ Synthesis | Raw amino acid | Purity of amino acid after purification (%) | Amount of each components in isocyanate composition (% by mass or ppm by mass) Isocyanate structure | Isocyanate compound (% by mass) |
|---|---|---|---|---|---|
| Example 46 | Fermentation | L-Lysine | 98 | 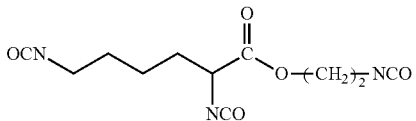 OCN~~~C(=O)O-(CH₂)₂-NCO with NCO branch | 96 |
|  |  |  | 98 | 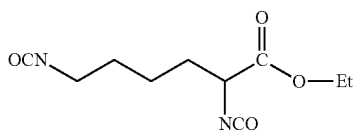 OCN~~~C(=O)O-Et with NCO branch | 3 |
| Example 47 | Fermentation | L-Lysine | 98 | 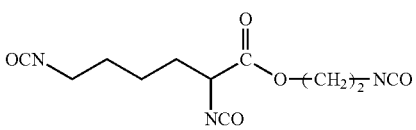 OCN~~~C(=O)O-(CH₂)₂-NCO with NCO branch | 98 |
|  |  |  | 98 | 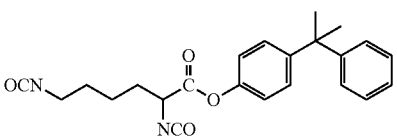 OCN~~~C(=O)O-cumylphenyl with NCO branch | 2 |

| Example | Metal atom Kind of metal in composition | Amount in composition (ppm by mass) | Compound | Amount (ppm by mass) | Hue value immediately after preparation | APHA Hue value after storing for a long time. Value in parenthesis indicates storage period at 25° C. | Stability Denaturation amount: % by mass Value in parenthesis indicates storage period at 25° C. |
|---|---|---|---|---|---|---|---|
| Example 46 | — | — | Dibutylphosphoric acid | 50 | 25 | 25 (300) | 0.03 (300) |
|  |  |  | DURANATE TPA-100 (manufactured by Asahi Kasei Corporation) | 200 |  |  |  |
|  |  |  | Compound having UV absorpotion at an area of decamere or higher isocyante. | 100 |  |  |  |
|  |  |  | α-Methylstyrene | 50 |  |  |  |
|  |  |  | Reaction product of isocyante and ethanol | 50 |  |  |  |
| Example 47 | — | — | p-toluenesulfonic acid | 50 | 25 | 25 (300) | 0.03 (300) |
|  |  |  | Phenyl benzoate | 200 |  |  |  |
|  |  |  | α-Methylstyrene | 100 |  |  |  |
|  |  |  | Reaction product of isocyante and 4-cumylphenol | 50 |  |  |  |
|  |  |  | Di(p-cumylphenol) carbonate | 50 |  |  |  |

TABLE 14

| | Isocyante raw material | | Purity of amino acid after purification (%) | Amount of each components in isocyanate composition (% by mass or ppm by mass) | | Metal atom | |
|---|---|---|---|---|---|---|---|
| | Fermentation/ Synthesis | Raw amino acid | | Isocyanate structure | Isocyanate compound (% by mass) | Kind of metal in composition | Amount in composition (ppm by mass) |
| Example 48 | Fermentation | L-aspartic acid | 97 | 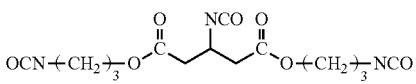 | 97 | — | — |
| Example 49 | Fermentation | L-Lysine | 98 | 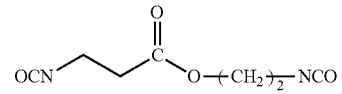 | 98 | — | — |
| | | | 98 | 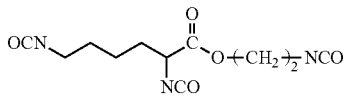 | 2 | | |

| | | Compound | | APHA | | Stability Denaturation amount: % by mass Value in parenthesis indicates storage period at 25° C. |
|---|---|---|---|---|---|---|
| | | Compound | Amount (ppm by mass) | Hue value immediately after preparation | Hue value after storing for a long time. Value in parenthesis indicates storage period at 25° C. | |
| | Example 48 | 2-ethylhexylphosphoric acid | 20 | 25 | 25 (300) | 0.03 (300) |
| | | DURANATE TLA-100 (manufactured by Asahi Kasei Corporation) | 300 | | | |
| | | 1,4-Diazabicyclo[2,2,2]octane | 20 | | | |
| | | Reaction product of isocyanate and 4-cumylphenol | 100 | | | |
| | | Di(p- cumylphenol) carbonate | 620 | | | |
| | Example 49 | Bromobenzene | 250 | 25 | 25 (300) | 0.03 (300) |
| | | Benzene sulfonate | 50 | | | |
| | | Butyl caprate | 850 | | | |
| | | Reaction product of isocyante and phenol | 100 | | | |
| | | Phenoxyphenyl carbamate | 130 | | | |

TABLE 15

| | Isocyante raw material | | | Amount of each components in isocyanate composition (% by mass or ppm by mass) | | | |
|---|---|---|---|---|---|---|---|
| | Fermentation/ Synthesis | Raw amino acid | Purity of amino acid after purification (%) | Isocyanate structure | Isocyanate compound (% by mass) | Metal atom Kind of metal in composition | Amount in composition (ppm by mass) |
| Example 50 | Fermentation | L-Lysine | 98 | 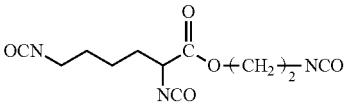 | 99 | — | — |
| Example 51 | Fermentation | L-Lysine | 98 | 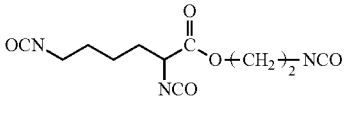 | 99 | — | — |
| Example 52 | Fermentation | L-Lysine | 98 | 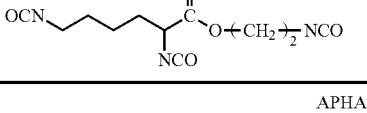 | 99 | — | — |

| | Compound | | | APHA | | |
|---|---|---|---|---|---|---|
| | Compound | Amount (ppm by mass) | Hue value immediately after preparation | Hue value after storing for a long time. Value in parenthesis indicates storage period at 25° C. | Stability Denaturation amount: % by mass Value in parenthesis indicates storage period at 25° C. | |
| Example 50 | DURANATE TKA-100 (manufactured by Asahi Kasei Corporation) | 3 | 17 | 35 (300) | 0.06 (300) | |
| Example 51 | DURANATE TKA-100 (manufactured by Asahi Kasei Corporation) | 20000 | 17 | 38 (300) | 0.06 (300) | |
| Example 52 | Compound having UV absorption at an area of decamere or higher isocyante. | 5 | 17 | 30 (300) | 0.07 (300) | |

TABLE 16

| | Isocyante raw material | | Purity of amino acid after purification (%) | Amount of each components in isocyanate composition (% by mass or ppm by mass) | |
|---|---|---|---|---|---|
| Example | Fermentation/ Synthesis | Raw amino acid | | Isocyanate structure | Isocyanate compound (% by mass) |
| 1 | Enzyme reaction | γ-aminobutyric acid | 99 | 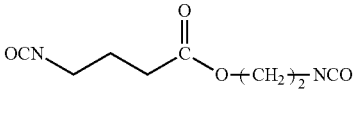 | 90 |
| 2 | Fermentation | L-α-alanine | 97 | 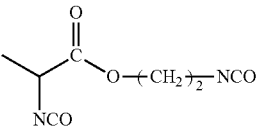 | 99 |

TABLE 16-continued

| | | Raw amino acid | Purity of amino acid after purification (%) | Isocyanate structure | |
|---|---|---|---|---|---|
| 3 | Fermentation | 2,6-diamino-heptanedioic acid | 90 | OCN-CH(COOMe)-(CH2)3-CH(COOMe)-NCO (dimethyl ester diisocyanate structure) | 90 |
| 4 | Fermentation | glycine | 98 | O=C(CH2NCO)-O-(CH2)2-NCO | 97 |

| | Amount of each components in isocyanate composition (% by mass or ppm by mass) | | | | APHA | | Stability |
|---|---|---|---|---|---|---|---|
| | Metal atom | | | | | Hue value after storing for a long time. Value in parenthesis indicates storage period at 25° C. | Denaturation amount: % by mass Value in parenthesis indicates storage period at 25° C.+ |
| Example | Kind of metal in composition | Amount in composition (ppm) | Compound | Amount (ppm) | Hue value immediately after preparation | | |
| | Cobalt | 1 | Dibenzyl ether | 200 | 120 | 150 (300) | 12 (300) |
| | | | Diphenyl carbonate | 500 | | | |
| | — | — | — | — | 19 | 130 (300) | 20 (300) |
| | — | — | — | — | 40 | 130 (300) | 15 (300) |
| | — | — | — | — | 19 | 125 (300) | 13 (300) |

TABLE 17

| | Isocyanate raw material | | | Amount of each components in isocyanate composition (% by mass or ppm by mass) |
|---|---|---|---|---|
| | Fermentation/Synthesis | Raw amino acid | Purity of amino acid after purification (%) | Isocyanate structure |
| Comparative Example 5 | Synthesis optical resolution | D-glutamic acid | 97 | OCN-(CH2)2-O-C(=O)-(CH2)2-CH(NCO)-C(=O)-O-(CH2)2-NCO |
| Comparative Example 6 | Fermentation | L-Lysine | 98 | OCN-(CH2)4-CH(NCO)-C(=O)-O-(CH2)2-NCO |

TABLE 17-continued

| | Fermentation/Synthesis | Raw amino acid | Purity of amino acid after purification (%) | Isocyanate structure |
|---|---|---|---|---|
| Comparative Example 7 | Fermentation | L-Lysine | 98 | OCN-(CH₂)₄-CH(NCO)-C(=O)-O-(CH₂)₂-NCO |
| Comparative Example 8 | Fermentation | L-Lysine | 98 | OCN-(CH₂)₄-CH(NCO)-C(=O)-O-(CH₂)₂-NCO |

| | Amount of each components in isocyanate composition (% by mass or ppm by mass) | | | | APHA Hue value | Stability Denaturation amount: |
|---|---|---|---|---|---|---|
| | | Metal atom | | | Hue value immediately after preparation | Hue value after storing for a long time. Value in parenthesis indicates storage period at 25° C. | % by mass Value in parenthesis indicates storage period at 25° C. |
| | Isocyanate compound (% by mass) | Kind of metal in composition | Amount in composition (ppm by mass) | Compound | Amount (ppm by mass) | | | |
| Comparative Example 5 | 98 | — | — | — | — | 30 | 125 (300) | 13 (300) |
| Comparative Example 6 | 88 | — | — | DURANATE TKA-100 (manufactured by Asahi Kasei Corporation) | 120000 | 20 | 130 (300) | 15 (300) |
| Comparative Example 7 | 99 | — | — | DURANATE TKA-100 (manufactured by Asahi Kasei Corporation) | 0.5 | 20 | 140 (300) | 15 (300) |
| Comparative Example 8 | 87 | — | — | Compound having UV absorption at an area of decamere or higher isocyanate. | 130000 | 20 | 130 (300) | 15 (300) |

TABLE 18

| | Isocyanate raw material | | | Amount of each components in isocyanate composition (% by mass or ppm by mass) |
|---|---|---|---|---|
| | Fermentation/Synthesis | Raw amino acid | Purity of amino acid after purification (%) | Isocyanate structure |
| Comparative Example 9 | Fermentation | L-Lysine | 98 | OCN-(CH₂)₄-CH(NCO)-C(=O)-O-(CH₂)₂-NCO |

TABLE 18-continued

| | | | | |
|---|---|---|---|---|
| Comparative Example 10 | Fermentation | glycine | 98 | (structure: OCN-CH₂-C(=O)-O-(CH₂)₂-NCO) |
| Comparative Example 11 | Synthesis optical resolution | D-glutamic acid | 97 | (structure: OCN-(CH₂)₂-O-C(=O)-CH₂-CH₂-CH(NCO)-C(=O)-O-(CH₂)₂-NCO) |

| | Amount of each components in isocyanate composition (% by mass or ppm by mass) | | | | APHA | | |
|---|---|---|---|---|---|---|---|
| | | Metal atom | | | | Hue value after storing for a long time. | Stability Denaturation amount: |
| | Isocyanate compound (% by mass) | Kind of metal in composition | Amount in composition (ppm by mass) | Compound | Amount (ppm by mass) | Hue value immediately after preparation | Value in parenthesis indicates storage period at 25° C. | Value in parenthesis indicates storage period at 25° C. % by mass |
| Comparative Example 9 | 99 | — | — | Compound having UV absorption at an area of decamere or higher isocyanate. | 0.3 | 20 | 130 (300) | 15 (300) |
| Comparative Example 10 | 97 | — | — | — | — | 19 | 125 (300) | 13 (300) |
| Comparative Example 11 | 98 | Iron | 0.001 | — | — | 30 | 125 (300) | 13 (300) |

Example B1

An isocyanate composition containing: 98.5% by mass of LTI as an isocyanate compound; 0.01 ppm of iron ion as a stabilizer; and 22 ppm by mass of benzyltoluene (mixture of isomers) was prepared.

1000 g of the prepared isocyanate composition was put into a four-necked flask made of glass and equipped with a thermometer, a stirrer and a nitrogen sealed tube, the air in the flask was replaced with nitrogen, and the composition was heated at 70° C. while conducting stirring. The refractive index of the reaction liquid was measured to gradually add a catalyst (tetramethylammoniumhydroxide) to the composition until the conversion rate of LTI became 20%, and, when the conversion rate became 20%, 0.5 g of a 85% phosphoric acid aqueous solution was added thereto to terminate the reaction. The amount of the catalyst required to achieve the conversion rate of 20% was 220 ppm by mass, relative to the isocyanate composition used in the reaction.

In the refractive index measurement of the reaction liquid, the change in the refractive index of the reaction liquid as a sample at 30° C. was measured using a refractometer (trade name of RA-520 manufactured by KYOTO ELECTRONICS MANUFACTURING CO., LTD).

After the reaction, the reaction liquid was subjected to filtration to obtain an isocyanate compound that is a LTI polymer containing LTI.

Examples B2 to B12, Comparative Examples B1 to B4

An isocyanurate-forming reaction was performed in the same way as that of Example B1, except that the amounts of an isocyanate composition and a stabilizer were changed as described in the following tables.

<Evaluation of Weather Resistance>

Evaluation of the weather resistance of the isocyanurate compound was conducted by the following procedure.

The isocyanurate compound and the polyester polyol (manufactured by Nuplex Resin under the trade name of Setal 166) were formulated such that the equivalent ratio of isocyanate groups/hydroxy groups became 1.0, and then a mixture composed of ethyl acetate/toluene/butyl acetate/xylene/propylene glycol monomethyl ether acetate (mass ratio of 30/30/20/15/5) was added thereto such that the mass of the solid contents including the isocyanurate compound and the polyol became 50% to obtain a coating material solution. The coating material solution was applied on a white enamel coated plate by conducting applicator coating such that the thickness after drying became 40 μm, and then the coated film was cured at a temperature of 20° C. and at a humidity of 63% for 1 week, followed by evaluating the weather resistance of the coated plate. The weather resistance was evaluated using a dew panel weather meter (manufactured by Suga Test Instruments Co., Ltd.). The evaluation was performed in accordance with JIS D 0205 under the conditions in which the irradiance was 30 W/m², and the panel temperature was 60° C., and the irradiation time and the condensation time were repeated at a cycle operation every 4 hours.

When the exposure time reached 1200 hours, the coated plate having a gloss retention rate of 80% or more was evaluated as "A", and the coated plate having a gloss retention rate of less than 80% was evaluated as "B". Results thereof are indicated in the following tables.

The amount of the catalyst required to obtain the composition and the conversion rate of 20% in the isocyanate composition is shown in the following tables. In the tables, "required amount of catalyst" was indicated by the ratio of the amount of the catalyst required to obtain the conversion rate of 20% (relative to the total mass of the isocyanate composition, ppm by mass).

TABLE 19

| Example | Isocyanate raw material Fermentation/ Synthesis | Raw amino acid | Purity of amino acid after purification (%) | Metal atom in raw amino acid or isocyanate precursor Kind of metal | Amount (ppm) | Amount of each components in isocyanate composition (% by mass or ppm by mass) Isocyanate structure |
|---|---|---|---|---|---|---|
| B1 | Fermentation | L-Lysine | 98 | Cobalt | 0 | 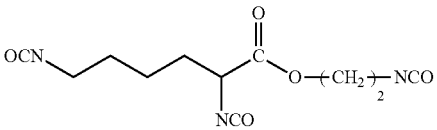 |
| B2 | Fermentation | L-glutamic acid | 97 | Nickel / Lead | 0.01 / 0.02 | 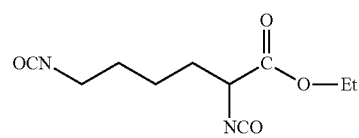 |
| B3 | Fermentation | L-Lysine | 98 | Cobalt | 0 | 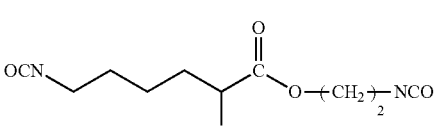 |
| B4 | Synthesis optical resolution | D-glutamic acid | 97 | — | 0.11 | 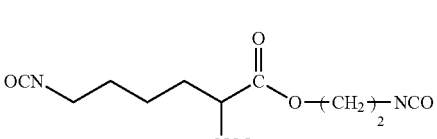 |

| Example | Isocyanate compound (% by mass) | Metal atom Kind of metal in composition | Amount in composition (ppm) | Compound | Amount (ppm) | Required amount of catalyst (ppm) | Evaluation result of weather resistance |
|---|---|---|---|---|---|---|---|
| B1 | 98.5 | Iron | 0.01 | Benzyltoluene | 22 | 300 | A |
| B2 | 97 | Nickel | 0.002 | 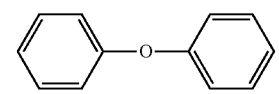 [SMILES: c1ccc(Oc2ccccc2)cc1] | 300 | 200 | A |

TABLE 19-continued

| | | | | | | | |
|---|---|---|---|---|---|---|---|
| B3 | 99 | — | — | diphenyl carbonate structure | 100 | 400 | A |
| B4 | 98 | — | — | α-methylstyrene structure | 70 | 300 | A |

TABLE 20

| | Isocyanate raw material | | Purity of amino acid after purifi- cation (%) | Metal atom in raw amino acid or isocyanate precursor | | Amount of each components in isocyanate composition |
|---|---|---|---|---|---|---|
| Ex- am- ple | Fer- men- ta- tion/ Syn- thesis | Raw amino acid | | Kind of metal | Amount (ppm) | (% by mass or ppm by mass) Isocyanate structure |
| B5 | Fer- men- ta- tion | L- Lysine HCl | 98 | Na | 1 | OCN–(CH2)4–CH(NCO)–C(=O)–O–(CH2)2–NCO |
| B6 | Fer- men- ta- tion | L- Lysine HCl | 99 | — | — | OCN–CH2CH2–C(=O)–O–(CH2)2–NCO |
| B7 | Fer- men- ta- tion | L- Lysine HCl | 97 | Iron | 5 | OCN–(CH2)4–CH(NCO)–C(=O)–O–(CH2)2–NCO |

| | Amount of each components in isocyanate composition (% by mass or ppm by mass) | | | |
|---|---|---|---|---|
| | Isocy- anate com- pound (% by mass) | Metal atom | | |
| Ex- am- ple | | Kind of metal in compo- sition | Amount in compo- sition (ppm) | Compound Compound |
| B5 | 98 | Titanium | 3 | OCN–(CH2)4–CH(NCO)–C(=O)–O–(CH2)2–NH–C(=O)–O–phenyl 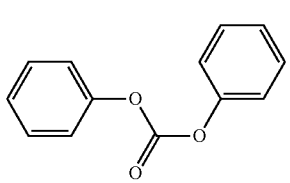 [SMILES: O=C(Oc1ccccc1)Oc1ccccc1] |

TABLE 20-continued

| | | | | | |
|---|---|---|---|---|---|
| B6 | 98 | Copper | 0.002 | | Carbon dioxide |
| B7 | 97 | Tin | 0.01 | | 1-Octene |

| Example | Amount of each components in isocyanate composition (% by mass or ppm by mass) Compound Amount (ppm) | Required amount of catalyst (ppm) | Evaluation result of weather resistance |
|---|---|---|---|
| B5 | 500 500 | 220 | A |
| B6 | 1000 | 300 | A |
| B7 | 700 | 300 | A |

TABLE 21

| Example | Isocyanate raw material Fermentation/ Synthesis | Raw amino acid | Purity of amino acid after purification (%) | Metal atom in raw amino acid or isocyanate precursor Kind of metal | Amount (ppm) | Isocyanate structure |
|---|---|---|---|---|---|---|
| B8 | Fermentation | L-Lysine HCl | 99 | — | — | OCN~~~~~C(=O)O-(CH₂)₂-NCO with NCO branch |
| B9 | Fermentation | L-Lysine HCl | 99 | — | — | OCN~~~~~C(=O)O-(CH₂)₂-NCO with NCO branch |
| B10 | Fermentation | L-Lysine HCl | 99 | — | — | OCN~~~~~C(=O)O-(CH₂)₂-NCO with NCO branch |
| B11 | Fermentation | L-Lysine HCl | 99 | — | — | OCN~~~~~C(=O)O-(CH₂)₂-NCO with NCO branch |
| B12 | Fermentation | L-Lysine HCl | 99 | — | — | OCN~~~~~C(=O)O-(CH₂)₂-NCO with NCO branch |

TABLE 21-continued

| Example | Isocyanate compound (% by mass) | Kind of metal in composition | Amount in composition (ppm) | Compound | Amount (ppm) | Required amount of catalyst | Evaluation result of weather resistance |
|---|---|---|---|---|---|---|---|
| B8 | 98 | — | — | Phenylphosphonic acid | 40 | 350 | A |
| B9 | 98 | — | — | Benzyl phthalate | 800 | 300 | A |
| B10 | 98 | — | — | Compound having UV absorption at an area of decamere or higher isocyanate | 25 | 300 | A |
|  |  |  |  | Lauryl Phosphate | 10 |  |  |
| B11 | 98 | — | — | DURANATE TKA-100 (manufactured by Asahi Kasei Corporation) | 20 | 300 | A |
| B12 | 98 | — | — | Dibutyl phosphate | 35 | 300 | A |
|  |  |  |  | DURANATE TLA-100 (manufactured by Asahi Kasei Corporation) | 650 |  |  |
|  |  |  |  | Compound having UV absorption at an area of decamere or higher isocyanate | 10 |  |  |

TABLE 22

| Comparative Example | Isocyanate raw material | | Purity of amino acid after purification (%) | Metal atom in raw amino acid or isocyanate precursor | | Amount of each components in isocyanate composition (% by mass or ppm by mass) Isocyanate structure |
|---|---|---|---|---|---|---|
|  | Fermentation/ Synthesis | Raw amino acid |  | Kind of metal | Amount (ppm) |  |
| B1 | Fermentation | L-Lysine HCl | 98 | Iron | 3 | 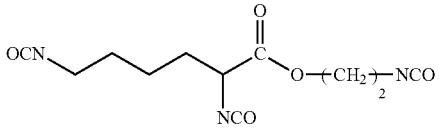 |
| B2 | Synthesis | DL-glutamic acid | 99 | Zinc | 2 | 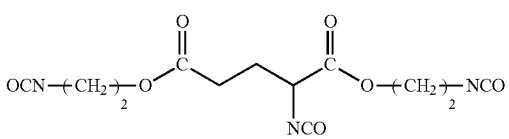 |
| B3 | Fermentation | L-α-alanine | 97 | Cobalt | 0.01 | 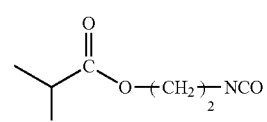 |
| B4 | Fermentation | glycine | 98 | Arsenic | 1 | 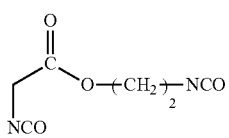 |

TABLE 22-continued

| Comparative Example | Isocyanate compound (% by mass) | Metal atom Kind of metal in composition | Amount in composition (ppm) | Compound | Amount (ppm) | Required amount of catalyst (ppm) | Evaluation result of weather resistance |
|---|---|---|---|---|---|---|---|
| B1 | 98 | — | — | Thiophenol | 100 | 300 | B |
| B2 | 97 | Lead<br>Arsenic | 1<br>5 |  | 2000 | 150 | B |
| B3 | 99 | Iron | 0.05 | 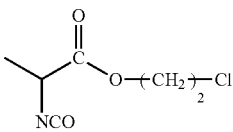 | 1100 | 200 | B |
|  |  |  |  | 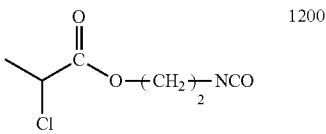 | 1200 |  |  |
| B4 | 99 | Copper<br>Iron | 5<br>70 | Chloride ion | 300 | 200 | B |

Example D1

An isocyanate composition containing: 98.5% by mass of LTI as an isocyanate compound; and 22 ppm by mass of benzyltoluene (mixture of isomers) was prepared.

700 g of the prepared isocyanate composition, 150 g of trimethyl phosphate, 150 g of methyl cellosolve acetate, and 15 g of water (mole ratio of HMDI/water=5) were put into a four-necked flask made of glass and equipped with a stirrer, a thermometer, a reflux condenser tube, and a nitrogen induction tube, under a nitrogen atmosphere, and the liquid temperature was maintained at 160° C. for 1 hour. A composition of a biuret-type polyisocyanate polymer having a hazen color number (APHA) of 35 was obtained.

Example D2 to D7, Comparative Examples D1 to D4

A biuret-forming reaction was performed by the same way as that of Example D1, except that the amounts of an isocyanate compound and a stabilizer in an isocyanate composition was changed in the following tables. The Hazen color numbers (APHA) of the obtained isocyanate polymers are shown in the following tables.

TABLE 23

| Example | Isocyanate raw material Fermentation/ Synthesis | Raw amino acid | Purity of amino acid after purification (%) | Metal atom in raw amino acid or isocyanate precursor Kind of metal | Amount (ppm) | Amount of each components in isocyanate composition (% by mass or ppm by mass) Isocyanate structure |
|---|---|---|---|---|---|---|
| D1 | Fermentation | L-Lysine | 98 | Cobalt | 0 | 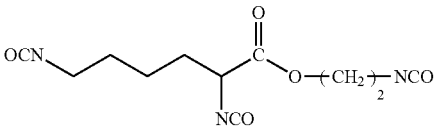 |

TABLE 23-continued

| | | | | | | | Structure |
|---|---|---|---|---|---|---|---|
| D2 | Fermentation | L-glutamic acid | 97 | Nickel<br>Lead | 0.01<br>0.02 | | 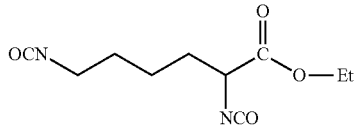 |
| D3 | Fermentation | L-Lysine | 98 | Cobalt | 0 | | 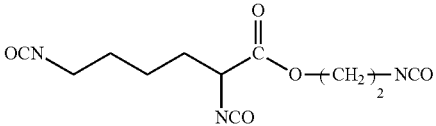 |
| D4 | Synthesis optical resolution | D-glutamic acid | 97 | — | 0.11 | | 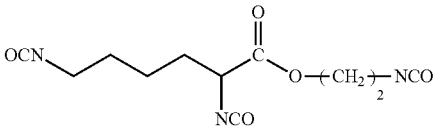 |

| | Amount of each components in isocyanate composition (% by mass or ppm by mass) | | | | | |
|---|---|---|---|---|---|---|
| | Isocyanate compound | Metal atom | | Compound | | Required amount of catalyst (ppm) |
| Example | (% by mass) | Kind of metal in composition | Amount in composition (ppm) | Compound | Amount (ppm) | |
| D1 | 98.5 | — | — | Benzyltoluene | 22 | 35 |
| D2 | 97 | Nickel | 0.002 | 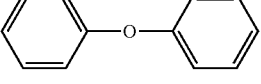 | 300 | 25 |
| D3 | 99 | Iron | 0.01 | 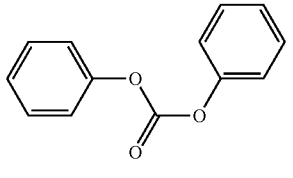 [SMILES: O=C(Oc1ccccc1)Oc1ccccc1] | 100 | 23 |
| D4 | 98 | — | — | 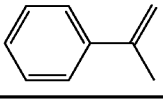 | 70 | 31 |

TABLE 24

| | Isocyanate raw material | | Purity of amino acid after purification (%) | Metal atom in raw amino acid or isocyanate precursor | | Amount of each components in isocyanate composition (% by mass or ppm by mass) |
|---|---|---|---|---|---|---|
| Example | Fermentation/ Synthesis | Raw amino acid | | Kind of metal | Amount (ppm) | Isocyanate structure |
| D5 | Fermentation | L-Lysine HCl | 98 | Na | 1 | 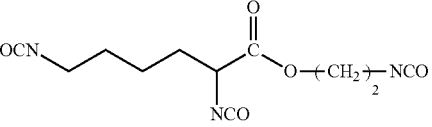 |

TABLE 24-continued

| | | | | | | Compound |
|---|---|---|---|---|---|---|
| D6 | Fermentation | L-Lysine HCl | 99 | — | — | 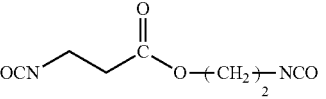 |
| D7 | Fermentation | L-Lysine HCl | 97 | Iron | 5 | 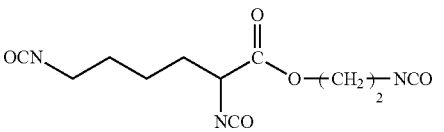 |

Amount of each components in isocyanate composition (% by mass or ppm by mass)

| Example | Isocyanate compound (% by mass) | Metal atom Kind of metal in composition | Amount in composition (ppm) | Compound Compound |
|---|---|---|---|---|
| D5 | 98 | Titanium | 3 | 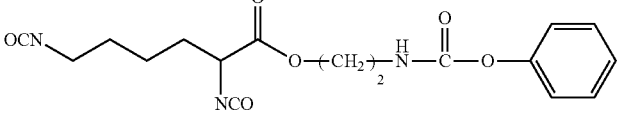 |
| D6 | 98 | Copper | 0.002 | Carbon dioxide |
| D7 | 97 | Tin | 0.01 | 1-Octene |

| Example | Amount of each components in isocyanate composition (% by mass or ppm by mass) Compound Amount (ppm) | Required amount of catalyst (ppm) |
|---|---|---|
| D5 | 500 | 39 |
| | 500 | |
| D6 | 1000 | 33 |
| D7 | 700 | 25 |

TABLE 25

| Comparative Example | Isocyanate raw material Fermentation/ Synthesis | Raw amino acid | Purity of amino acid after purification (%) | Metal atom in raw amino acid or isocyanate precursor Kind of metal | Amount (ppm) | Amount of each components in isocyanate composition (% by mass or ppm by mass) Isocyanate structure |
|---|---|---|---|---|---|---|
| D1 | Fermentation | L-Lysine HCl | 98 | Iron | 3 | 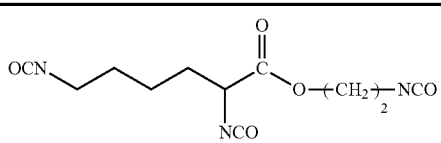 |
| D2 | Synthesis | DL-glutamic acid | 99 | Zinc | 2 | 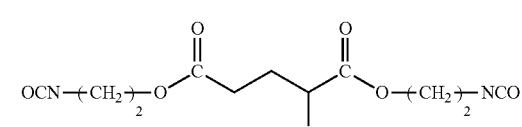 |
| D3 | Fermentation | L-α-alanine | 97 | Cobalt | 0.01 | 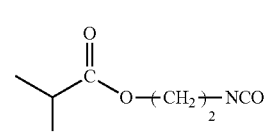 |
| D4 | Fermentation | glycine | 98 | Arsenic | 1 | 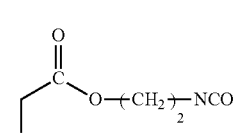 |

| Comparative Example | Isocyanate compound (% by mass) | Metal atom Kind of metal in composition | Amount in composition (ppm) | Compound | Amount (ppm) | Required amount of catalyst (ppm) |
|---|---|---|---|---|---|---|
| D1 | 98 | — | — | Thiophenol | 100 | 120 |
| D2 | 97 | Lead<br>Arsenic | 1<br>5 |  | 2000 | 150 |
| D3 | 99 | Iron | 0.05 | 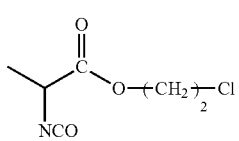 | 1100 | 50 |
|  |  |  |  | 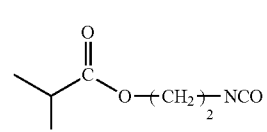 | 1200 |  |
| D4 | 99 | Copper<br>Iron | 5<br>70 | Chloride ion | 300 | 150 |

Example E1

Ethyl 2,6-diisocyanatohexanoate was synthesized by the same way as that of Synthesis Example 3 except that ethanol was used instead of phenol. 95.0% by mass of LTI and 5.0% by mass of ethyl 2,6-diisocyanatohexanoate were mixed under a nitrogen atmosphere to obtain an isocyanate composition composed of a trifunctional isocyanate and a difunctional isocyanate.

(Coating Film Performance: Test of Chemical Resistance of Coating Film)

A coating material composition was prepared by formulating an acrylic polyol (Setalux 1767 manufactured by Nuplex Resins) in the isocyanate composition such that the amount of hydroxy groups of the acrylic polyol, relative to 1 mole of an isocyanate group of the isocyanate composition, became 1.05 moles, and then diluting the mixture with a butyl acetate such that the amount of the solid content became 50%. The coating material composition was coated on a glass plate such that the thickness of the dried coating film became 15 to 20 μm, and then left still at room temperature for 20 minutes, followed by conducting baking at 120° C. for 20 minute to obtain a urethane coating film. An absorbent cotton impregnated with methyl ethyl ketone was placed on the obtained urethane coating film, and left still for 30 minutes, followed by removing the absorbent cotton therefrom, and then placing the glass plate on a back plate to evaluate a change in an external appearance (white turbidity, low gloss, presence or absence of tack occurrence, presence or absence of swelling) of the coating film visually or by touch. The urethan coated film using the isocyanate composition was evaluated as ○ in accordance with the criteria in which a case where no change was confirmed was evaluated as ○, a case where a slight change was confirmed was evaluated as Δ, and a case where an apparent change was continued was evaluated as x.

(Increase in Viscosity when Stored)

An acceleration test in which the isocyanate composition was stored at 80° C. for 100 days was conducted to evaluate effects of suppressing the viscosity increase when the isocyanate composition was stored. The isocyanate composition was evaluated as ○, in accordance with the criteria in which a case where almost no viscosity increase was confirmed after storage was evaluated as ○, a case where a slight viscosity increase was confirmed was evaluated as Δ, and a case where an apparent viscosity increase was confirmed was evaluated as x.

Examples E2 to E16, Comparative Examples E1 to E2

Isocyanate compositions composed of trifunctional isocyanates and difunctional isocyanates were prepared by the same way as that of Example E1, and then evaluated in terms of the coating film performance and the viscosity increase when stored. Results are shown in the following tables.

Among isocyanates constituting the isocyanate compositions, difunctional isocyanates in Examples E2, E6 to E9, E11 to E12, and E14, and Comparative Examples E1 to E2 were prepared in a similar way to that of Synthesis Example A3, and other isocyanates were prepared in a similar way to that of Example 1.

TABLE 26

| | Raw amino acid | Isocyanate structure | Isocyanate compound (% by mass) | Coating film performance | Viscosity increase when stored at 80° C. for 100 days |
|---|---|---|---|---|---|
| Example E1 | L-Lysine | OCN~~~~C(=O)-O-(CH₂)₂-NCO, NCO | 95.0 | ○ | ○ |
| | L-Lysine | OCN~~~~CH(NCO)-C(=O)-O-Et | 5.0 | | |
| Example E2 | L-glutamic acid | OCN-(CH₂)₂-O-C(=O)~~~CH(NCO)~~~C(=O)-O-(CH₂)₂-NCO | 98.1 | ○ | ○ |
| | Ornithine | OCN~~~CH(NCO)-C(=O)-O-Et | 1.9 | | |

TABLE 26-continued

| | Raw amino acid | Isocyanate structure | Isocyanate compound (% by mass) | Coating film performance | Viscosity increase when stored at 80° C. for 100 days |
|---|---|---|---|---|---|
| Example E3 | L-glutamic acid | 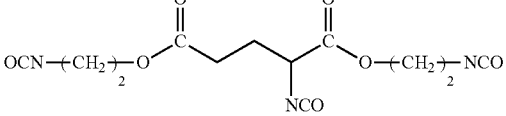 | 99.7 | ○ | ○ |
| | glycine | 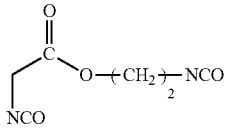 | 0.3 | | |
| Example E4 | L-Lysine | 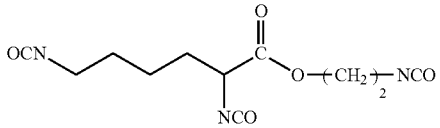 | 96.0 | ○ | ○ |
| | L-α-alanine | 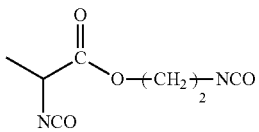 | 4.0 | | |

TABLE 27

| | Raw amino acid | Isocyanate structure | Isocyanate compound (% by mass) | Coating film performance | Viscosity increase when stored at 80° C. for 100 days |
|---|---|---|---|---|---|
| Example E5 | L-Lysine | 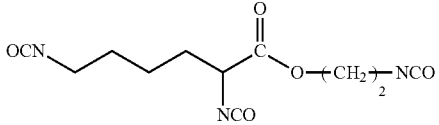 | 99.8 | ○ | ○ |
| | β-alanine | 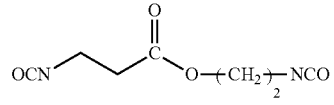 | 0.2 | | |
| Example E6 | L-glutamic acid | 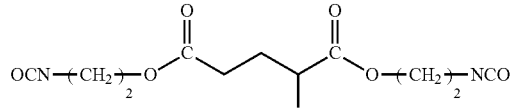 | 98.3 | ○ | ○ |
| | L-Lysine | 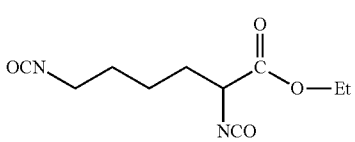 | 1.7 | | |

TABLE 27-continued

| | Raw amino acid | Isocyanate structure | Isocyanate compound (% by mass) | Coating film performance | Viscosity increase when stored at 80° C. for 100 days |
|---|---|---|---|---|---|
| Example E7 | L-Lysine HCl | OCN–...–C(=O)–O–(CH$_2$)$_2$–NCO, with NCO branch | 99.0 | ○ | ○ |
| | L-Lysine | OCN–...(NCO)–C(=O)–O–phenyl | 1.0 | | |
| Example E8 | L-Lysine HCl | OCN–...(NCO)–C(=O)–O–(CH$_2$)$_2$–NCO | 96.8 | ○ | ○ |
| | L-Lysine | OCN–...(NCO)–C(=O)–O–(p-tolyl) | 3.2 | | |
| Example E9 | L-Lysine HCl | OCN–...(NCO)–C(=O)–O–(CH$_2$)$_2$–NCO | 98.5 | ○ | ○ |
| | 2,6-diaminoheptanedioic acid | OCN–...(NCO)–...(NCO)–C(=O)–O–Me ; Me–O–C(=O)– | 1.5 | | |
| Example E10 | DL-glutamic acid | OCN–(CH$_2$)$_2$–O–C(=O)–...(NCO)–C(=O)–O–(CH$_2$)$_2$–NCO | 97.3 | ○ | ○ |
| | Methionine | MeS–...–(NCO)–C(=O)–O–(CH$_2$)$_2$–NCO | 2.7 | | |

TABLE 28

| | Raw amino acid | Isocyanate structure | Isocyanate compound (% by mass) | Coating film performance | Viscosity increase when stored at 80° C. for 100 days |
|---|---|---|---|---|---|
| Example E11 | L-Lysine HCl | OCN-(CH₂)₄-CH(NCO)-C(=O)-O-(CH₂)₂-NCO | 95.8 | ○ | ○ |
| | L-Lysine | OCN-(CH₂)₄-CH(NCO)-C(=O)-O-C₆H₄-C(CH₃)₂-C₆H₅ | 3.2 | | |
| Example E12 | L-Lysine HCl | OCN-(CH₂)₄-CH(NCO)-C(=O)-O-(CH₂)₂-NCO | 98.4 | ○ | ○ |
| | L-Lysine | OCN-(CH₂)₄-CH(NCO)-C(=O)-O-C₆H₄-C(CH₃)₂-CH₂-C(CH₃)₃ | 1.6 | | |
| Example E13 | DL-glutamic acid | OCN-(CH₂)₂-O-C(=O)-CH₂-CH₂-CH(NCO)-C(=O)-O-(CH₂)₂-NCO | 99 | ○ | Δ |
| | Methionine | CH₃-S-CH₂-CH₂-CH(NCO)-C(=O)-O-(CH₂)₂-NCO | 150 (ppm by mass) | | |
| Example E14 | L-glutamic acid | OCN-(CH₂)₂-O-C(=O)-CH₂-CH₂-CH(NCO)-C(=O)-O-(CH₂)₂-NCO | 75.5 | Δ | ○ |
| | Ornithine | OCN-(CH₂)₃-CH(NCO)-C(=O)-O-CH₂-CH₃ | 24.5 | | |
| Example E15 | L-Lysine | OCN-(CH₂)₄-CH(NCO)-C(=O)-O-(CH₂)₂-NCO | 88.0 | Δ | ○ |

TABLE 28-continued

| | | Amount of each components in isocyanate composition (% by mass when unit is not indicated.) | | Coating film performance | Viscosity increase when stored at 80° C. for 100 days |
|---|---|---|---|---|---|
| | Raw amino acid | Isocyanate structure | Isocyanate compound (% by mass) | | |
| | β-alanine | 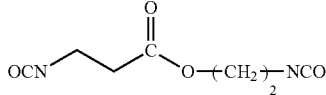 | 12.0 | | |

TABLE 29

| | | Amount of each components in isocyanate composition (% by mass when unit is not indicated.) | | Coating film performance | Viscosity increase when stored at 80° C. for 100 days |
|---|---|---|---|---|---|
| | Raw amino acid | Isocyanate structure | Isocyanate compound (% by mass) | | |
| Example E16 | L-glutamic acid | OCN—(CH₂)₂—O—C(=O)—CH₂CH₂—CH(NCO)—C(=O)—O—(CH₂)₂—NCO | 99.9 | ○ | Δ |
| | glycine | CH₂(NCO)—C(=O)—O—(CH₂)₂—NCO | 450 (ppm by mass) | | |
| Comparative Example E1 | L-Lysine | OCN—(CH₂)₄—CH(NCO)—C(=O)—O—(CH₂)₂—NCO | 63.0 | X | ○ |
| | L-Lysine | OCN—(CH₂)₄—CH(NCO)—C(=O)—O—C₆H₄—C(CH₃)₂—C₆H₅ | 37.0 | | |
| Comparative Example E2 | L-Lysine | OCN—(CH₂)₄—CH(NCO)—C(=O)—O—(CH₂)₂—NCO | 99.9 | ○ | X |
| | L-Lysine | OCN—(CH₂)₄—CH(NCO)—C(=O)—O—C₆H₄—C(CH₃)₂—CH₂—C(CH₃)₃ | 80 (ppm by mass) | | |

INDUSTRIAL APPLICABILITY

According to the present invention, an isocyanate composition containing a specific isocyanate compound, which is excellent in coloring suppressibility and stability when stored for a long time, is provided.

The invention claimed is:

1. An isocyanate composition comprising: an isocyanate compound of formula (1) and/or formula (2); and further comprising:
   a compound of formula (3), which is different from the isocyanate compound, in an amount of 1.0 ppm by mass to 10% by mass, relative to a total mass of the isocyanate compound in the composition; and/or
   a compound having an UV absorption in an area of decamer or higher isocyanates in a measurement spectrum of gel permeation chromatography, in an amount of 1.0 ppm by mass to 10% by mass, relative to the total mass of the isocyanate compound in the composition;

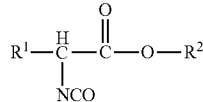
(1)

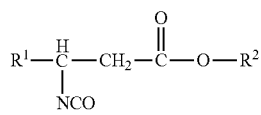
(2)

wherein $R^1$ represents a hydrogen or a monovalent organic group, and $R^2$ represents a monovalent organic group, and,

(3)

wherein $R^{13}$ represents an organic group with a valence of a, $R^{14}$ represents a monovalent organic group, and a represents an integer of 1 or 2.

2. The isocyanate composition according to claim 1, further comprising, relative to the total mass of the isocyanate compound in the composition,
   1.0 ppm by mass to 10% by mass of saturated and/or unsaturated hydrocarbon compounds having a linear-chain structure, a branched-chain structure, or a cyclic structure, and/or,
   1.0 ppm by mass to 10% by mass of a compound having at least one bond selected from the group consisting an ether bond and a thioether bond.

3. The isocyanate composition according to claim 1, further comprising 1.0 ppm by mass to 10% by mass, relative to the total mass of the isocyanate compound in the composition, of a carbamate group-containing compound and/or a carbonic acid ester.

4. The isocyanate composition according to claim 1, further comprising:
   1.0 ppm by mass to 10% by mass, relative to the total mass of the isocyanate compound in the composition, of a basic amino compound, and/or,
   a halogen ion, and/or, a hydrolyzable halogen compound.

5. The isocyanate composition according to claim 1, further comprising, relative to the total mass of the isocyanate compound in the composition,
   1.0 ppm by mass to $1.0\times10^3$ ppm by mass of a phosphoric acid and/or a phosphoric acid ester, and/or,
   1.0 ppm by mass to $1.0\times10^3$ ppm by mass of a sulfuric acid and/or a sulfuric acid ester.

6. The isocyanate composition according to claim 1, comprising, as the isocyanate compound, a trifunctional isocyanate compound having three isocyanate groups in a molecule thereof, and a difunctional isocyanate compound having two isocyanate groups in a molecule thereof.

7. An isocyanate composition comprising an isocyanate compound of formula (1) and/or formula (2), comprising, relative to a total mass of the isocyanate compound in the composition, 1.0 ppm by mass to $1.0\times10^3$ ppm by mass of a phosphoric acid and/or a phosphoric acid ester, and/or, 1.0 ppm by mass to $1.0\times10^3$ ppm by mass of a sulfuric acid and/or a sulfuric acid ester,

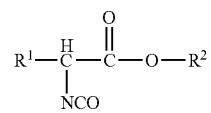
(1)

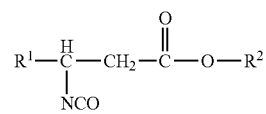
(2)

wherein, $R^1$ represents a hydrogen or a monovalent organic group, Fe represents a monovalent organic group, and.

8. The isocyanate composition according to claim 1, wherein an amount of the isocyanate compound, relative to the total mass of the isocyanate composition, is 90% by mass or more.

9. The isocyanate composition according to claim 1, comprising the isocyanate compound of formula (1), and the isocyanate compound has a structure derived from an α-amino acid.

10. The isocyanate composition according to claim 1, comprising the isocyanate compound of formula (2), and the isocyanate compound has a structure derived from a β-amino acid.

11. A method for producing an isocyanate composition of claim 9, comprising: preparing the isocyanate compound of formula (1) using a corresponding α-amino acid by fermentation; and mixing the isocyanate compound with a compound of formula (3) and/or a compound having an UV absorption in an area of decamer or higher isocyanates in a measurement spectrum of gel permeation chromatography, wherein the α-amino acid is an amino acid having a purity of 90% or more,

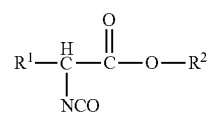
(1)

wherein $R^1$ represents a hydrogen or a monovalent organic group, and $R^2$ represents a monovalent organic group,

(3)

wherein $R^{13}$ represents an organic group with a valence of a, $R^{14}$ represents a monovalent organic group, and a represents an integer of 1 or 2.

12. The method for producing an isocyanate composition according to claim 11, further comprising a step in which the isocyanate compound is subjected to distillation purification.

13. A method for producing an isocyanate polymer comprising a step in which an isocyanate compound contained in an isocyanate composition of claim 1 is reacted, wherein
the isocyanate polymer comprises a unit of formula (4) and at least one unit selected from the group consisting of units of formulae (5), (6), (7), (8), (9), (10), (11) and (12), and
a nitrogen atom constituting the isocyanate polymer is bonded with a carbon atom,

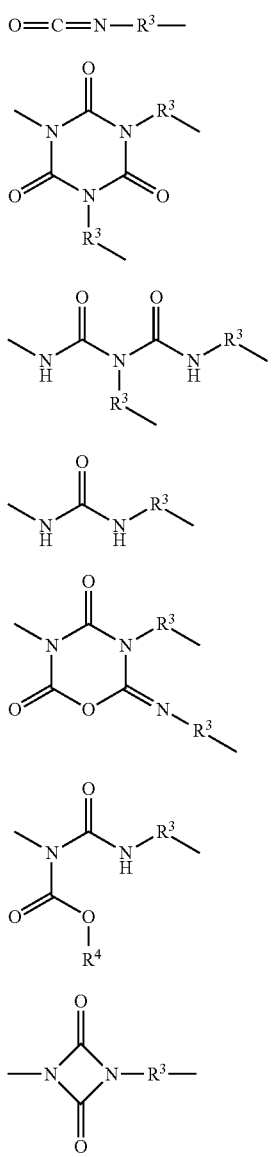

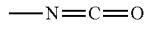

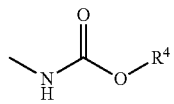

wherein each $R^3$ independently represents a divalent hydrocarbon group and each $R^4$ independently represents a monovalent organic group.

14. The isocyanate composition according to claim 1, comprising the compound of formula (3), which is different from the isocyanate compound, in an amount of 1.0 ppm by mass to 10% by mass, relative to a total mass of the isocyanate compound in the composition.

15. The isocyanate composition according to claim 1, comprising the compound having an UV absorption in an area of decamer or higher isocyanates in a measurement spectrum of gel permeation chromatography, in an amount of 1.0 ppm by mass to 10% by mass, relative to the total mass of the isocyanate compound in the composition.

16. The isocyanate composition according to claim 1, comprising the compound of formula (3), which is different from the isocyanate compound, in an amount of 3.0 ppm by mass to $1.0 \times 10^3$ ppm by mass, relative to a total mass of the isocyanate compound in the composition.

17. The isocyanate composition according to claim 1, comprising the compound of formula (3), which is different from the isocyanate compound, in an amount of 5.0 ppm by mass to $3.0 \times 10^3$ ppm by mass, relative to a total mass of the isocyanate compound in the composition.

18. The isocyanate composition according to claim 1, comprising the compound having an UV absorption in an area of decamer or higher isocyanates in a measurement spectrum of gel permeation chromatography, in an amount of 3.0 ppm by mass to $3.0 \times 10^3$ ppm by mass, relative to the total mass of the isocyanate compound in the composition.

19. The isocyanate composition according to claim 1, comprising the compound having an UV absorption in an area of decamer or higher isocyanates in a measurement spectrum of gel permeation chromatography, in an amount of 10 ppm by mass to $1.0 \times 10^3$ ppm by mass, relative to the total mass of the isocyanate compound in the composition.

20. The isocyanate composition according to claim 1, wherein the monovalent organic group of $R^1$ represents a group represented by —C(=O)OR$^2$ or —CH$_2$—C(=O)O—R$^2$.

21. An isocyanate composition according to claim 7, wherein the monovalent organic group of $R^1$ represents a group represented by —C(=O)OR$^2$ or —CH$_2$—C(=O)O—R$^2$.

22. The method according to claim 11, wherein the monovalent organic group of $R^1$ represents a group represented by —C(=O)OR$^2$ or —CH$_2$—C(=O)O—R$^2$.

* * * * *